US009913706B2

(12) United States Patent
Lashinski et al.

(10) Patent No.: US 9,913,706 B2
(45) Date of Patent: Mar. 13, 2018

(54) ADJUSTABLE ENDOLUMENAL IMPLANT FOR RESHAPING THE MITRAL VALVE ANNULUS

(71) Applicant: MILLIPEDE, INC., Santa Rosa, CA (US)

(72) Inventors: Randall Lashinski, Windsor, CA (US); Matthew Rust, Windsor, CA (US); Patrick Macaulay, Windsor, CA (US); Terry Wayne Daniels, Occidental, CA (US); Kris Kristoffersen, Redding, CA (US)

(73) Assignee: Millipede, Inc., Santa Rosa, CA (US)

( * ) Notice: Subject to any disclaimer, the term of this patent is extended or adjusted under 35 U.S.C. 154(b) by 0 days.

(21) Appl. No.: 15/689,467

(22) Filed: Aug. 29, 2017

(65) Prior Publication Data
US 2017/0360549 A1 Dec. 21, 2017

Related U.S. Application Data

(63) Continuation of application No. 15/482,479, filed on Apr. 7, 2017, which is a continuation of application (Continued)

(51) Int. Cl.
A61F 2/02 (2006.01)
A61F 2/24 (2006.01)

(52) U.S. Cl.
CPC ............ A61F 2/02 (2013.01); A61F 2/24 (2013.01); A61F 2/2409 (2013.01);
(Continued)

(58) Field of Classification Search
CPC .... A61F 2/2445; A61F 2/2442; A61F 2/2418; A61F 2/2409; A61F 2/2466; A61F 2/02
See application file for complete search history.

(56) References Cited

U.S. PATENT DOCUMENTS 3,143,742 A 8/1964 Cromie
4,602,911 A 7/1986 Ahmadi et al.
(Continued)

FOREIGN PATENT DOCUMENTS

EP 2 047 824 5/2012
EP 2 656 816 10/2013
(Continued)

OTHER PUBLICATIONS

B. Braun Medical Inc., "Pulmonary Embolism: IVC Filters." Retrieved from the Internet: http://www.bbraunusa.com/pe/pe05a.html, 2004, 2 pages.
(Continued)

Primary Examiner — Thomas McEvoy
(74) Attorney, Agent, or Firm — Knobbe Martens Olson & Bear LLP

(57) ABSTRACT

Excessive dilation of the annulus of a mitral valve may lead to regurgitation of blood during ventricular contraction. This regurgitation may lead to a reduction in cardiac output. Disclosed are systems and methods relating to an implant configured for reshaping a mitral valve. The implant comprises a plurality of struts with anchors for tissue engagement. The implant is compressible to a first, reduced diameter for transluminal navigation and delivery to the left atrium of a heart. The implant may then expand to a second, enlarged diameter to embed its anchors to the tissue surrounding and/or including the mitral valve. The implant may then contract to a third, intermediate diameter, pulling the tissue radially inwardly, thereby reducing the mitral valve and lessening any of the associated symptoms including mitral regurgitation.

16 Claims, 52 Drawing Sheets

Related U.S. Application Data

No. 14/861,877, filed on Sep. 22, 2015, now Pat. No. 9,615,926, which is a continuation of application No. 14/562,554, filed on Dec. 5, 2014, now Pat. No. 9,180,005.

(60) Provisional application No. 62/025,967, filed on Jul. 17, 2014, provisional application No. 62/038,032, filed on Aug. 15, 2014.

(52) U.S. Cl.
CPC .......... *A61F 2/2412* (2013.01); *A61F 2/2442* (2013.01); *A61F 2/2445* (2013.01); *A61F 2/2463* (2013.01)

(56) References Cited

U.S. PATENT DOCUMENTS

| | | |
|---|---|---|
| 4,820,299 A | 4/1989 | Philippe et al. |
| 5,254,127 A | 10/1993 | Wholey et al. |
| 5,370,685 A | 12/1994 | Stevens |
| 5,674,280 A | 10/1997 | Davidson et al. |
| 5,769,816 A | 6/1998 | Barbut et al. |
| 5,772,590 A | 6/1998 | Webster, Jr. |
| 5,810,882 A | 9/1998 | Bolduc et al. |
| 5,824,066 A | 10/1998 | Gross |
| 5,968,053 A | 10/1999 | Revelas |
| 5,984,959 A | 11/1999 | Robertson et al. |
| 6,001,127 A | 12/1999 | Schoon et al. |
| 6,210,432 B1 | 4/2001 | Soleme et al. |
| 6,254,642 B1 | 7/2001 | Taylor |
| 6,355,030 B1 | 3/2002 | Aldrich et al. |
| 6,582,460 B1 | 6/2003 | Cryer |
| 6,652,537 B2 | 11/2003 | Mercereau et al. |
| 6,676,692 B2 | 1/2004 | Rabkin et al. |
| 6,695,878 B2 | 2/2004 | McGuckin et al. |
| 6,702,826 B2 | 3/2004 | Liddicoat et al. |
| 6,726,716 B2 | 4/2004 | Marquez |
| 6,730,121 B2 | 5/2004 | Ortiz et al. |
| 6,776,791 B1 | 8/2004 | Stallings et al. |
| 6,790,231 B2 | 9/2004 | Liddicoat et al. |
| 6,805,710 B2 | 10/2004 | Bolling et al. |
| 6,824,562 B2 | 11/2004 | Mathis et al. |
| 6,875,231 B2 | 4/2005 | Anduiza et al. |
| 6,913,608 B2 | 7/2005 | Liddicoat et al. |
| 6,942,641 B2 | 9/2005 | Seddon |
| 6,942,694 B2 | 9/2005 | Liddicoat et al. |
| 6,951,571 B1 | 10/2005 | Srivastava |
| 6,964,684 B2 | 11/2005 | Ortiz et al. |
| 6,986,775 B2 | 1/2006 | Morales et al. |
| 7,007,698 B2 | 3/2006 | Thornton |
| 7,041,120 B2 | 5/2006 | Li et al. |
| 7,063,722 B2 | 6/2006 | Marquez |
| 7,081,131 B2 | 7/2006 | Thornton |
| 7,087,064 B1 | 8/2006 | Hyde |
| 7,112,219 B2 | 9/2006 | Vidlund et al. |
| 7,160,322 B2 | 1/2007 | Gabbay |
| 7,166,127 B2 | 1/2007 | Spence et al. |
| 7,247,134 B2 | 7/2007 | Vidlund et al. |
| 7,297,150 B2 | 11/2007 | Cartledge et al. |
| 7,323,004 B2 | 1/2008 | Parihar |
| 7,329,278 B2 | 2/2008 | Seguin et al. |
| 7,329,280 B2 | 2/2008 | Bolling et al. |
| 7,357,815 B2 | 4/2008 | Shaoulian et al. |
| 7,361,190 B2 | 4/2008 | Shaoulian et al. |
| 7,381,218 B2 | 6/2008 | Schreck |
| 7,404,824 B1 | 7/2008 | Webler et al. |
| 7,455,690 B2 | 11/2008 | Cartledge et al. |
| 7,482,936 B2 | 1/2009 | Bolling |
| 7,485,142 B2 | 2/2009 | Milo |
| 7,507,252 B2 | 3/2009 | Lashinski et al. |
| 7,527,646 B2 | 5/2009 | Rahdert et al. |
| 7,556,647 B2 | 7/2009 | Drews et al. |
| 7,611,534 B2 | 11/2009 | Kapadia et al. |
| 7,637,946 B2 | 12/2009 | Solem et al. |
| 7,655,040 B2 | 2/2010 | Douk et al. |
| 7,674,222 B2 | 3/2010 | Nikolic et al. |
| 7,691,144 B2 | 4/2010 | Chang et al. |
| 7,695,510 B2 | 4/2010 | Bloom et al. |
| 7,731,649 B2 | 6/2010 | Ferrazzi |
| 7,740,638 B2 | 6/2010 | Hyde |
| D627,245 S | 11/2010 | Corn |
| 7,850,709 B2 | 12/2010 | Cummins et al. |
| 7,887,582 B2 | 2/2011 | Mathis et al. |
| 7,896,913 B2 | 3/2011 | Damm et al. |
| 7,914,576 B2 | 3/2011 | Navia et al. |
| 7,914,577 B2 | 3/2011 | Cox |
| 7,927,371 B2 | 4/2011 | Navia et al. |
| 7,935,145 B2 | 5/2011 | Alfieri et al. |
| 7,959,673 B2 | 6/2011 | Carpentier et al. |
| 7,972,378 B2 | 7/2011 | Tabor et al. |
| 7,988,725 B2 | 8/2011 | Gross et al. |
| 7,993,395 B2 | 8/2011 | Vanermen et al. |
| 8,012,202 B2 | 9/2011 | Alameddine |
| 8,016,877 B2 | 9/2011 | Seguin et al. |
| 8,052,751 B2 | 11/2011 | Aklog et al. |
| 8,128,641 B2 | 3/2012 | Wardle |
| 8,142,494 B2 | 3/2012 | Rahdert et al. |
| 8,142,496 B2 | 3/2012 | Berreklouw |
| 8,157,853 B2 | 4/2012 | Laske et al. |
| 8,163,013 B2 | 4/2012 | Machold et al. |
| 8,182,528 B2 | 5/2012 | Salahieh et al. |
| 8,187,207 B2 | 5/2012 | Machold et al. |
| 8,211,171 B2 | 7/2012 | Kim et al. |
| 8,226,707 B2 | 7/2012 | White |
| 8,277,502 B2 | 10/2012 | Miller et al. |
| 8,287,555 B2 | 10/2012 | Starksen et al. |
| 8,287,591 B2 | 10/2012 | Keidar et al. |
| 8,333,777 B2 | 12/2012 | Schaller et al. |
| 8,357,195 B2 | 1/2013 | Kuehn |
| 8,366,766 B2 | 2/2013 | Berreklouw |
| 8,430,926 B2 | 4/2013 | Kirson |
| 8,449,604 B2 | 5/2013 | Moaddeb et al. |
| 8,454,683 B2 | 6/2013 | Rafiee et al. |
| 8,480,733 B2 | 7/2013 | Navia et al. |
| 8,512,403 B2 | 8/2013 | Navia et al. |
| 8,551,161 B2 | 10/2013 | Dolan |
| 8,551,162 B2 | 10/2013 | Fogarty et al. |
| 8,560,009 B2 | 10/2013 | Etemad |
| 8,579,964 B2 | 11/2013 | Lane et al. |
| 8,603,159 B2 | 12/2013 | Seguin et al. |
| 8,608,797 B2 | 12/2013 | Gross et al. |
| 8,668,713 B2 | 3/2014 | Horan et al. |
| 8,673,001 B2 | 3/2014 | Cartledge et al. |
| 8,685,080 B2 | 4/2014 | White |
| 8,690,858 B2 | 4/2014 | Machold et al. |
| 8,690,939 B2 | 4/2014 | Miller et al. |
| 8,715,342 B2 | 5/2014 | Zipory et al. |
| 8,721,681 B2 | 5/2014 | Leung et al. |
| 8,721,718 B2 | 5/2014 | Kassab |
| 8,758,372 B2 | 6/2014 | Cartledge et al. |
| 8,778,021 B2 | 7/2014 | Cartledge |
| 8,784,482 B2 | 7/2014 | Rahdert et al. |
| 8,808,371 B2 | 8/2014 | Cartledge |
| 8,858,622 B2 | 10/2014 | Machold et al. |
| 8,864,823 B2 | 10/2014 | Cartledge et al. |
| 8,882,830 B2 | 11/2014 | Cartledge et al. |
| 8,906,046 B2 | 12/2014 | Anderson |
| 8,926,696 B2 | 1/2015 | Cabiri et al. |
| 8,940,042 B2 | 1/2015 | Miller et al. |
| 8,945,210 B2 | 2/2015 | Cartledge et al. |
| 8,956,407 B2 | 2/2015 | Macoviak et al. |
| 8,979,923 B2 | 3/2015 | Spence et al. |
| 8,979,925 B2 | 3/2015 | Chang et al. |
| 8,992,604 B2 | 3/2015 | Gross et al. |
| 8,998,979 B2 | 4/2015 | Seguin |
| 9,011,520 B2 | 4/2015 | Miller et al. |
| 9,023,065 B2 | 5/2015 | Bolduc et al. |
| 9,040,092 B2 | 5/2015 | Edelman et al. |
| 9,107,749 B2 | 8/2015 | Bobo et al. |
| 9,119,718 B2 | 9/2015 | Keranen |
| 9,138,315 B2 | 9/2015 | Straubinger et al. |
| 9,180,005 B1 | 11/2015 | Lashinski et al. |
| 9,192,471 B2 | 11/2015 | Bolling |

(56) References Cited

U.S. PATENT DOCUMENTS

| | | |
|---|---|---|
| 9,204,956 B2 | 12/2015 | Chanduszko et al. |
| 9,204,964 B2 | 12/2015 | Dahlgren et al. |
| 9,301,756 B2 | 4/2016 | Wardle |
| 9,301,860 B2 | 4/2016 | White |
| 9,326,859 B2 | 5/2016 | Cartledge et al. |
| 9,339,379 B2 | 5/2016 | Quadri et al. |
| 9,351,830 B2 | 5/2016 | Gross et al. |
| RE46,126 E | 8/2016 | Kirson |
| RE46,127 E | 8/2016 | Kirson |
| 9,421,099 B2 | 8/2016 | Dolan |
| 9,427,215 B2 | 8/2016 | Cartledge et al. |
| 9,439,763 B2 | 9/2016 | Geist et al. |
| 9,474,606 B2 | 10/2016 | Zipory et al. |
| 9,504,572 B2 | 11/2016 | Mauch et al. |
| 9,566,178 B2 | 2/2017 | Cartledge et al. |
| 9,585,747 B2 | 3/2017 | Quadri et al. |
| 9,592,122 B2 | 3/2017 | Zipory et al. |
| 9,610,156 B2 | 4/2017 | Lashinski |
| 9,615,926 B2 | 4/2017 | Lashinski et al. |
| 9,622,862 B2 | 4/2017 | Lashinski et al. |
| 9,730,790 B2 | 8/2017 | Quadri et al. |
| 9,744,038 B2 | 8/2017 | Dahlgren et al. |
| 9,788,941 B2 | 10/2017 | Hacohen |
| 9,801,714 B2 | 10/2017 | White |
| 9,827,093 B2 | 11/2017 | Cartledge et al. |
| 2002/0002401 A1 | 1/2002 | McGuckin et al. |
| 2002/0042621 A1 | 4/2002 | Liddicoat et al. |
| 2002/0151961 A1 | 10/2002 | Lashinski et al. |
| 2002/0161377 A1 | 10/2002 | Rabkin |
| 2002/0173841 A1 | 11/2002 | Ortiz et al. |
| 2002/0183837 A1 | 12/2002 | Streeter et al. |
| 2003/0040793 A1 | 2/2003 | Marquez |
| 2003/0093148 A1 | 5/2003 | Bolling |
| 2003/0158570 A1 | 8/2003 | Ferrazzi |
| 2003/0199975 A1 | 10/2003 | Gabbay |
| 2003/0199987 A1 | 10/2003 | Berg et al. |
| 2003/0212453 A1 | 11/2003 | Mathis et al. |
| 2003/0225420 A1 | 12/2003 | Wardle |
| 2003/0233142 A1 | 12/2003 | Morales et al. |
| 2004/0010275 A1 | 1/2004 | Jacobs et al. |
| 2004/0049266 A1 | 3/2004 | Anduiza et al. |
| 2004/0067544 A1 | 4/2004 | Vogel et al. |
| 2004/0092965 A1 | 5/2004 | Parihar |
| 2004/0122516 A1 | 6/2004 | Fogarty et al. |
| 2004/0127982 A1 | 7/2004 | Machold et al. |
| 2004/0148019 A1 | 7/2004 | Vidlund et al. |
| 2004/0148020 A1 | 7/2004 | Vidlund et al. |
| 2004/0148021 A1 | 7/2004 | Cartledge et al. |
| 2004/0167620 A1 | 8/2004 | Ortiz et al. |
| 2004/0172063 A1 | 9/2004 | Li et al. |
| 2004/0186565 A1 | 9/2004 | Schreck |
| 2004/0193191 A1 | 9/2004 | Starksen et al. |
| 2004/0193261 A1 | 9/2004 | Berreklouw |
| 2004/0236419 A1 | 11/2004 | Milo |
| 2004/0243104 A1 | 12/2004 | Seddon |
| 2004/0243227 A1 | 12/2004 | Starksen et al. |
| 2004/0243230 A1 | 12/2004 | Navia et al. |
| 2004/0249400 A1 | 12/2004 | Vargas et al. |
| 2004/0249453 A1 | 12/2004 | Cartledge et al. |
| 2004/0260394 A1 | 12/2004 | Douk et al. |
| 2005/0004665 A1 | 1/2005 | Aklog |
| 2005/0004668 A1 | 1/2005 | Aklog et al. |
| 2005/0038508 A1 | 2/2005 | Gabbay |
| 2005/0049692 A1 | 3/2005 | Numamoto |
| 2005/0075713 A1 | 4/2005 | Biancucci et al. |
| 2005/0080454 A1 | 4/2005 | Drews et al. |
| 2005/0131533 A1 | 6/2005 | Alfieri et al. |
| 2005/0137701 A1 | 6/2005 | Salahieh et al. |
| 2005/0177180 A1 | 8/2005 | Kaganov et al. |
| 2005/0182290 A1 | 8/2005 | Lau et al. |
| 2005/0182486 A1 | 8/2005 | Gabbay |
| 2005/0192629 A1 | 9/2005 | Saadat et al. |
| 2005/0234508 A1 | 10/2005 | Cummins et al. |
| 2005/0267560 A1 | 12/2005 | Bates |
| 2005/0288776 A1 | 12/2005 | Shaoulian et al. |
| 2005/0288783 A1 | 12/2005 | Shaoulian et al. |
| 2006/0015178 A1 | 1/2006 | Moaddeb et al. |
| 2006/0025855 A1 | 2/2006 | Lashinski et al. |
| 2006/0025858 A1 | 2/2006 | Alameddine |
| 2006/0100699 A1 | 5/2006 | Vidlund et al. |
| 2006/0106305 A1 | 5/2006 | Lau |
| 2006/0106456 A9 | 5/2006 | Machold et al. |
| 2006/0129235 A1 | 6/2006 | Seguin et al. |
| 2006/0149349 A1 | 7/2006 | Garbe |
| 2006/0149368 A1 | 7/2006 | Spence |
| 2006/0178733 A1 | 8/2006 | Pinchuk et al. |
| 2006/0184240 A1 | 8/2006 | Jimenez et al. |
| 2006/0184241 A1 | 8/2006 | Marquez |
| 2006/0195012 A1 | 8/2006 | Mortier et al. |
| 2006/0206203 A1 | 9/2006 | Yang et al. |
| 2006/0229708 A1 | 10/2006 | Powell et al. |
| 2006/0241746 A1 | 10/2006 | Shaoulian et al. |
| 2006/0241747 A1 | 10/2006 | Shaoulian et al. |
| 2006/0282161 A1 | 12/2006 | Huynh et al. |
| 2007/0005129 A1 | 1/2007 | Damm et al. |
| 2007/0016287 A1 | 1/2007 | Cartledge et al. |
| 2007/0027533 A1 | 2/2007 | Douk |
| 2007/0050019 A1 | 3/2007 | Hyde |
| 2007/0055368 A1 | 3/2007 | Rhee et al. |
| 2007/0112423 A1 | 5/2007 | Chu |
| 2007/0112425 A1 | 5/2007 | Schaller et al. |
| 2007/0142907 A1 | 6/2007 | Moaddeb et al. |
| 2007/0156233 A1 | 7/2007 | Kapadia et al. |
| 2007/0161846 A1 | 7/2007 | Nikolic et al. |
| 2007/0239272 A1 | 10/2007 | Navia et al. |
| 2007/0244553 A1 | 10/2007 | Rafiee et al. |
| 2007/0244556 A1 | 10/2007 | Rafiee et al. |
| 2007/0250161 A1 | 10/2007 | Dolan |
| 2007/0276478 A1 | 11/2007 | Marmureanu et al. |
| 2007/0282436 A1 | 12/2007 | Pinchuk |
| 2007/0293942 A1 | 12/2007 | Mirzaee |
| 2007/0299543 A1 | 12/2007 | Cartledge et al. |
| 2008/0027483 A1 | 1/2008 | Cartledge et al. |
| 2008/0067713 A1 | 3/2008 | Bordener |
| 2008/0077235 A1 | 3/2008 | Kirson |
| 2008/0177380 A1 | 7/2008 | Starksen et al. |
| 2008/0255661 A1 | 10/2008 | Straubinger et al. |
| 2008/0288060 A1 | 11/2008 | Kaye et al. |
| 2009/0082857 A1 | 3/2009 | Lashinski et al. |
| 2009/0087414 A1 | 4/2009 | Edelman et al. |
| 2009/0149872 A1 | 6/2009 | Gross et al. |
| 2009/0177276 A1 | 7/2009 | Carpentier et al. |
| 2009/0182419 A1 | 7/2009 | Bolling |
| 2009/0198316 A1 | 8/2009 | Laske et al. |
| 2009/0264996 A1 | 10/2009 | Vanermen et al. |
| 2009/0276040 A1 | 11/2009 | Rowe et al. |
| 2009/0287299 A1 | 11/2009 | Tabor et al. |
| 2009/0287304 A1 | 11/2009 | Dahlgren et al. |
| 2009/0306622 A1 | 12/2009 | Machold |
| 2010/0004740 A1 | 1/2010 | Sequin et al. |
| 2010/0049315 A1 | 2/2010 | Kirson |
| 2010/0087855 A1 | 4/2010 | Leung et al. |
| 2010/0100174 A1 | 4/2010 | Gurskis |
| 2010/0121433 A1 | 5/2010 | Bolling |
| 2010/0152838 A1 | 6/2010 | Kang et al. |
| 2010/0152840 A1 | 6/2010 | Seguin et al. |
| 2010/0152845 A1 | 6/2010 | Bloom et al. |
| 2010/0185229 A1 | 7/2010 | Horan |
| 2010/0249920 A1 | 9/2010 | Bolling |
| 2010/0298929 A1 | 11/2010 | Thornton |
| 2011/0022166 A1 | 1/2011 | Dahlgren et al. |
| 2011/0066224 A1 | 3/2011 | White |
| 2011/0066236 A1 | 3/2011 | Khalapyan |
| 2011/0106247 A1 | 5/2011 | Miller et al. |
| 2011/0172760 A1 | 7/2011 | Anderson |
| 2011/0202127 A1 | 8/2011 | Mauch et al. |
| 2011/0219603 A1* | 9/2011 | White .................. A61F 2/2412 29/428 |
| 2011/0224785 A1* | 9/2011 | Hacohen ............ A61B 17/0401 623/2.18 |
| 2011/0288632 A1 | 11/2011 | White |
| 2011/0319989 A1 | 12/2011 | Lane et al. |
| 2012/0022640 A1 | 1/2012 | Gross et al. |
| 2012/0027116 A1 | 2/2012 | Etemad |

(56) References Cited

U.S. PATENT DOCUMENTS

| | | |
|---|---|---|
| 2012/0053680 A1 | 3/2012 | Bolling et al. |
| 2012/0109288 A1 | 5/2012 | Bolling |
| 2012/0109289 A1 | 5/2012 | Bolling |
| 2012/0203330 A1 | 8/2012 | Cartledge et al. |
| 2012/0215303 A1 | 8/2012 | Quadri |
| 2012/0283757 A1 | 11/2012 | Miller et al. |
| 2012/0308610 A1 | 12/2012 | Edelman et al. |
| 2013/0006295 A1 | 1/2013 | Chanduszko |
| 2013/0046373 A1 | 2/2013 | Cartledge |
| 2013/0123910 A1 | 5/2013 | Cartledge et al. |
| 2013/0123913 A1 | 5/2013 | Kuehn |
| 2013/0138207 A1 | 5/2013 | Quadri |
| 2013/0177600 A1 | 7/2013 | Edelman et al. |
| 2013/0226289 A1 | 8/2013 | Shaolian et al. |
| 2013/0325118 A1 | 12/2013 | Cartledge |
| 2014/0039612 A1 | 2/2014 | Dolan |
| 2014/0142695 A1 | 5/2014 | Gross et al. |
| 2014/0163690 A1 | 6/2014 | White |
| 2014/0222136 A1 | 8/2014 | Geist et al. |
| 2014/0277427 A1 | 9/2014 | Ratz et al. |
| 2014/0277563 A1 | 9/2014 | White |
| 2014/0296962 A1 | 10/2014 | Cartledge et al. |
| 2014/0309731 A1 | 10/2014 | Quadri et al. |
| 2014/0336756 A1 | 11/2014 | Lee et al. |
| 2015/0112432 A1 | 4/2015 | Reich et al. |
| 2015/0127096 A1 | 5/2015 | Rowe et al. |
| 2015/0142105 A1 | 5/2015 | Bolling et al. |
| 2015/0157459 A1 | 6/2015 | Macoviak |
| 2015/0250461 A1 | 9/2015 | Berreklouw |
| 2016/0008130 A1 | 1/2016 | Hasin |
| 2016/0015515 A1 | 1/2016 | Lashinski et al. |
| 2016/0038285 A1 | 2/2016 | Glenn et al. |
| 2016/0095704 A1 | 4/2016 | Whitman |
| 2016/0120645 A1 | 5/2016 | Alon |
| 2016/0128829 A1 | 5/2016 | Oba |
| 2016/0235526 A1 | 8/2016 | Lashinski et al. |
| 2016/0256276 A1 | 9/2016 | Yaron |
| 2016/0317304 A1 | 11/2016 | Spence et al. |
| 2016/0324638 A1 | 11/2016 | Dolan et al. |
| 2017/0035564 A1 | 2/2017 | Ryan |
| 2017/0049570 A1 | 2/2017 | O'Beirne et al. |
| 2017/0086974 A1 | 3/2017 | Lashinski et al. |
| 2017/0143488 A1 | 5/2017 | Lashinski et al. |
| 2017/0143489 A1 | 5/2017 | Lashinski et al. |
| 2017/0156860 A1 | 6/2017 | Lashinski et al. |
| 2017/0209253 A1 | 7/2017 | Lashinski et al. |
| 2017/0231759 A1 | 8/2017 | Geist |

FOREIGN PATENT DOCUMENTS

| | | |
|---|---|---|
| JP | 2008-538937 | 11/2008 |
| JP | 2010-284536 | 12/2010 |
| WO | WO 90/09153 | 8/1990 |
| WO | WO 93/15690 | 8/1993 |
| WO | WO 97/12565 | 4/1997 |
| WO | WO 97/20524 | 6/1997 |
| WO | WO 98/24386 | 6/1998 |
| WO | WO 99/29269 | 6/1999 |
| WO | WO 99/49816 | 10/1999 |
| WO | WO 00/07521 | 2/2000 |
| WO | WO 00/18333 | 4/2000 |
| WO | WO 00/44311 | 8/2000 |
| WO | WO 00/62715 | 10/2000 |
| WO | WO 01/89440 | 11/2001 |
| WO | WO 02/094132 | 11/2002 |
| WO | WO 03/017874 | 3/2003 |
| WO | WO 03/053289 | 7/2003 |
| WO | WO 03/080150 | 10/2003 |
| WO | WO 03/105670 | 12/2003 |
| WO | WO 03/105730 | 12/2003 |
| WO | WO 04/014282 | 2/2004 |
| WO | WO 04/019816 | 3/2004 |
| WO | WO 04/019826 | 3/2004 |
| WO | WO 04/030569 | 4/2004 |
| WO | WO 04/031717 | 4/2004 |
| WO | WO 04/032717 | 4/2004 |
| WO | WO 04/103223 | 12/2004 |
| WO | WO 04/112657 | 12/2004 |
| WO | WO 05/002424 | 1/2005 |
| WO | WO 05/007037 | 1/2005 |
| WO | WO 05/046488 | 5/2005 |
| WO | WO 05/087139 | 9/2005 |
| WO | WO 06/011275 | 2/2006 |
| WO | WO 06/052687 | 5/2006 |
| WO | WO 06/086135 | 8/2006 |
| WO | WO 06/086434 | 8/2006 |
| WO | WO 06/105084 | 10/2006 |
| WO | WO 06/116129 | 11/2006 |
| WO | WO 06/116357 | 11/2006 |
| WO | WO 07/021834 | 2/2007 |
| WO | WO 08/15257 | 2/2008 |
| WO | WO 08/088716 | 7/2008 |
| WO | WO 09/140268 | 11/2009 |
| WO | WO 10/011699 | 1/2010 |
| WO | WO 12/027116 | 3/2012 |
| WO | WO 12/167095 | 12/2012 |
| WO | WO 13/088327 | 6/2013 |
| WO | WO 15/77599 | 5/2015 |

OTHER PUBLICATIONS

Bonow et al., "ACC/AHA 2006 Guidelines for the Management of Patients with Valvular Heart Disease," J. American College of Cardiology, 48(3):e1-148 (2006).

Boston Scientific, "Device Details." Retrieved from the Internet: http://bostonscientific.com/rned_specialty/deviceDetail.jsp [retrieved on Aug. 31, 2006], 1 page.

Braunberger et al., "Very Long-Term Results (More Than 20 years) of Valve Repair with Carpentier's Techniques in Nonrheumatic Mitral Valve Insufficiency," Circulation, 104:I8-I11 (2001).

Braunwald et al., "Conservative Management of tricuspid Regurgitation in Patients Undergoing Mitral Valve Replacement," Circulation, XXXV and XXXVI:I63-I69 (1967).

Carpentier et al., "Surgical Management of Acquired Tricuspid Valve Disease," J. Thoracic and Cardiovascular Surgery, 67(1):53-65 (1974).

Center for Devices and Radiological Health, U.S. Dept. of Health and Human Services Food and Drug Administration "Guidance for Annuloplasty Rings 510(k) Submissions; Final Guidance for Industry and FDA Staff," 1-15 (2001).

Cosgrove et al., "Mitral Valvuloplasty," Curro. Probl. Cardiol., 359-405 (1989).

Dreyfus et al., "Secondary Tricuspid Regurgitation or Dilatation: Which Should Be the Criteria for Surgical Repair?," Ann. Thorac. Surg., 79:127-32 (2005).

Google Images, Recurved Hooks. Retrieved from the Internet: www.implementology.org.pf and personal.cityu.edu.hk [retrieved on Dec. 14, 2006], 1 page.

Leung et al., "Barbed, Bi-directional Surgical Sutures: In Vivo Strength and Histopathology Evaluations," Society for Biomaterials 28th Annual Meeting Transactions, #724 (2003) 1 p.

Magovern et al., "Sutureless Artificial Heart Valves," Circulation, 27:784-788 (1963).

McCarthy et al., "Tricuspid Valve Repair: Durability and Risk Factors for Failure," J. Thoracic and Cardiovascular Surgery, 127:674-85 (2004).

Nath et al., "Impact of Tricuspid Regurgitation on Long-Term Survival," J. American College of Cardiology, 43(3):405-409 (2004).

Navia et al., "Surgical Management of Secondary Tricuspid Valve Regurgitation: Anulus, Commissure, or Leaflet Procedure?," Abstract presented at American Association for Thoracic Surgery Annual Meeting (2009).

Rogers et al., "The Tricuspid Valve: Current Perspective and Evolving Management of Tricuspid Regurgitation," Circulation, 119:2718-2725 (2009).

Sagie et al., "Determinants of Functional Tricuspid Regurgitation in Incomplete Tricuspid Valve Closure: Doppler Color Flow Study of 109 Patients," J. American College of Cardiology, 24:446-53 (1994).

(56) References Cited

OTHER PUBLICATIONS

Savage et al., "Use of Mitral Valve Repair: Analysis of Contemporary United States Experience Reported to the Society of Thoracic Surgeons National Cardiac Database," Ann. Thorac Surg., 75:820-825 (2003).
Shiran et al., "Tricuspid Regurgitation in Mitral Valve Disease," J. American College of Cardiology, 53(5):401-408 (2009).
Song et al., "Factors Associated with Development of Late Significant Tricuspid Regurgitation after Successful Left-Sided Valve Surgery," Heart, 95:931-936 (2009).
Tang et al., "Tricuspid Valve Repair with an Annuloplasty Ring Results in Improved Long-Term Outcomes," Circulation, 114:1577-1581 (2006).
Thompson, "Percutaneous Heart Valve Technology: The Mitral Challenge," Medtech Insight, 11(2):38-52 (2009).
Zlotnick et al., "A Perfectly Functioning Magovem-Cromie Sutureless Prosthetic Aortic Valve 42 Years After Implantation," Circulation, 117:e1-e2 (2008).
International Search Report and Written Opinion dated Oct. 8, 2015 in PCT/US2015/040622.
Japanese Office Action; Application No. 2009-544986; pp. 6 dated Aug. 13, 2012.
Japanese Decision to Grant; Application No. 2009-544986; pp. 3 dated Mar. 27, 2013.
Japanese Office Action with English translation; Application No. 2012-500990; pp. 8 dated Jan. 8, 2014.
European Search Report; Application No. 10754160.9-1659 / 2408400; pp. 6 dated May 3, 2013.
European Search Report; Application No. 08727364.5-1651; pp. 3 dated Oct. 8, 2013.
European Office Action; Application No. 08727364.5-1651; pp. 6 dated Jan. 2, 2014.
Partial European Search Report; Application No. 11186500.2-1659 / 2412316; pp. 7 dated Jun. 5, 2013.
European Search Report; Application No. 11186500.2-1659; pp. 5 dated Sep. 20, 2013.
European Office Action; Application No. 11186500.2-1659; pp. 6 dated Oct. 11, 2013.
International Search Report, Patent Cooperation Treaty, dated Jul. 1, 2008 for Application No. PCT/US2008/050224.
International Preliminary Report on Patentability; Application No. PCT/US08/050224; pp. 9 dated Jul. 14, 2009.
International Search Report and Written Opinion dated Jul. 13, 2010 for PCT/US2010/027943.
International Preliminary Report on Patentability; Application No. PCT/US2010/027943; pp. 12 dated Sep. 20, 2011.
International Search Report and Written Opinion dated Sep. 22, 2011 for PCT/US2011/039022.
International Search Report and Written Opinion for Application No. PCT/US2011/047345, dated Dec. 7, 2011.
International Preliminary Report on Patentability; Application No. PCT/US2011/047345; pp. 9, dated Feb. 26, 2013.
International Search Report and Written Opinion dated Dec. 11, 2013 for PCT/US2013/059751.
International Search Report and Written Opinion dated May 26, 2017 for PCT/US2017/016284.
International Search Report and Written Opinion; Application No. PCT/US2014/026333 dated Jul. 21, 2014.
International Search Report and Written Opinion dated May 5, 2016 in PCT/US2016/017866.
International Search Report and Written Opinion dated Apr. 19, 2017 in PCT/US16/062107.

\* cited by examiner

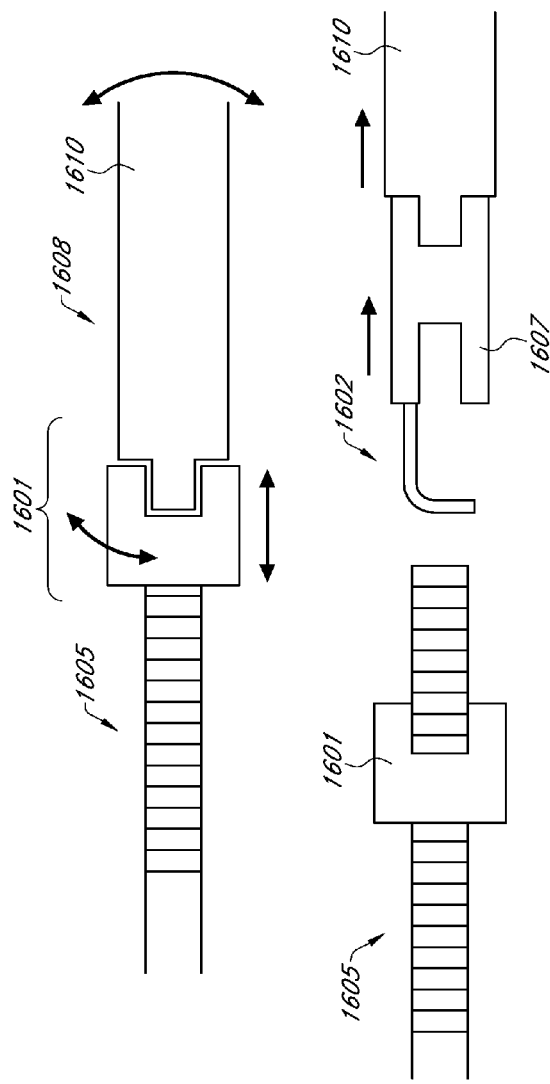
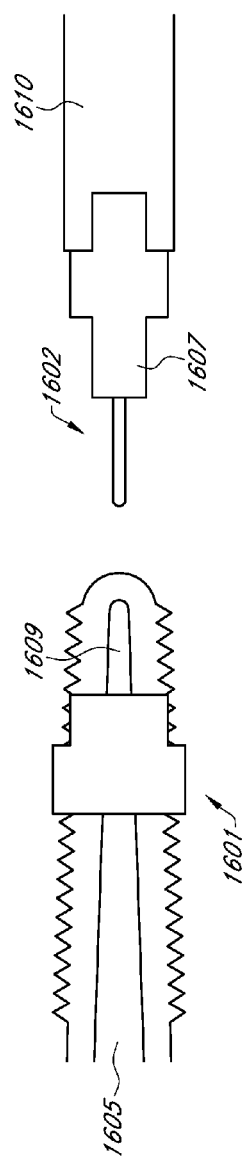
FIG. 16A
FIG. 16B

ADJUSTABLE ENDOLUMENAL IMPLANT FOR RESHAPING THE MITRAL VALVE ANNULUS

CROSS-REFERENCE TO RELATED APPLICATIONS

This application is a continuation application of U.S. patent application Ser. No. 15/482,479, filed Apr. 7, 2017, which is a continuation application of U.S. patent application Ser. No. 14/861,877, filed Sep. 22, 2015 (patented on Apr. 11, 2017, as U.S. Pat. No. 9,615,926), which is a continuation application of U.S. patent application Ser. No. 14/562,554, filed Dec. 5, 2014 (patented on Nov. 10, 2015, as U.S. Pat. No. 9,180,005), which claims the priority benefit under 35 U.S.C. § 119(e) of U.S. Provisional Application No. 62/025,967, filed Jul. 17, 2014, and of U.S. Provisional Application No. 62/038,032, filed Aug. 15, 2014, the entireties of which are hereby incorporated by reference herein.

BACKGROUND

Field

The present application relates generally to treating heart disease, and more specifically, to methods and systems for an adjustable endolumenal mitral valve ring.

Description of Related Art

Heart disease can cause the chambers of the heart to expand and/or weaken. With specific reference to the mitral valve of the heart, when the left ventricle dilates, papillary muscles become displaced. When the mitral valve is incompetent due to heart disease, the mitral annulus (e.g., the annulus of the mitral valve) dilates excessively. In this state of dilation, the valve leaflets of the mitral valve no longer effectively close, or coapt, during systolic contraction. Consequently, regurgitation of blood occurs during ventricular contraction and cardiac output decreases.

This condition is typically addressed by open-heart surgical implantation of an annuloplasty ring. Typically, a surgeon positions an annuloplasty ring proximate to the mitral annulus and sutures it in place, thereby restoring the mitral valve to approximately its native circumference. If successful, the valve leaflets can then function normally again.

However, open-heart surgery is not without its shortcomings. Open heart-surgery is highly invasive and has many associated risks, including risks of infection, heart attack and/or stroke, memory loss, blood clots, blood loss, injury to the surrounding anatomy, and/or many other pains and/or discomforts. Accordingly, there is a need in the art for less invasive systems and methods for addressing heart valve incompetency of the mitral valve.

SUMMARY

The present disclosure includes methods and systems relating to reshaping a mitral valve using a laser-cut tubular implant having a plurality of struts with barbed anchors for tissue engagement. The implant may be compressible to a first, reduced diameter for transluminal navigation and delivery to the mitral valve treatment site. It may then be expandable to a second, enlarged diameter for engaging tissue surrounding and/or including the mitral valve (as used herein, the tissue surrounding and/or including the mitral valve includes the mitral annulus). Typically, the anchors of the implant embed into the tissue while the implant is in the enlarged state. The implant may then contract to a third, intermediate diameter, pulling the tissue of the mitral valve radially inward, which reduces the mitral valve. The reduction of the mitral valve may lessen any of the symptoms associated with excessive mitral valve dilation, including mitral regurgitation. Any or all of the expanding or contracting functions can be accomplished either actively or passively.

In some embodiments, the implant may be delivered to the tissue surrounding and/or including the mitral valve using a delivery system. The delivery system may comprise of a delivery catheter connected to the implant. The delivery catheter may have a handle that can manipulate the delivery catheter and the implant. Typically, the delivery of the implant may be performed under fluoroscopic and/or echo guidance.

The delivery system may use a sheath to cover the implant for delivery and a guidewire to advance and steer the delivery catheter into position with the implant at the distal end. The implant may be exposed by pulling the sheath back. Once exposed and delivered, the anchors of the implant may be embedded into the tissue surrounding and/or including the mitral valve. In some embodiments, the anchors of the implant may be retractable and/or helical-shaped. In some cases, the anchors may engage the tissue by pushing, pulling, and/or rotating the anchors.

The implant size and/or shape may then be changed by a number of adjustment mechanisms, including mechanisms that use nuts, clips, and/or cables. Some mechanisms serve as restraints to adjustably change the distance between two or more anchors on the implant, such as through a working range, and ultimately affect the size and/or shape of a valve annulus, such as the mitral valve annulus. The adjustment of these mechanisms may be performed by using rotational drivers and/or actuators at the proximal end of the handle of the delivery catheter. The rotational drivers and/or actuators may be used to compress or expand the implant at the operator's discretion to adjust the final size and/or shape of the implant (and hence, the mitral valve) as desired. The delivery system may be disconnected and removed once the implant has been delivered and adjusted as desired, and/or once mitral regurgitation has been reduced or eliminated. The implant may be left as a permanent implant.

BRIEF DESCRIPTION OF THE DRAWINGS

The disclosed aspects will hereinafter be described in conjunction with the appended drawings, provided to illustrate and not to limit the disclosed aspects, wherein like designations denote like elements.

FIGS. 16A-B illustrate a side-view and top-view of a rotational driver that can be used to rotate a nut over a strut in an appropriate direction.

DETAILED DESCRIPTION

This disclosure encompasses all changes, substitutions, variations, alterations, and modifications to the example embodiments herein that a person having ordinary skill in the art would comprehend. Similarly, where appropriate, the appended claims encompass all changes, substitutions, variations, alterations, and modifications to the example embodiments herein that a person having ordinary skill in the art would comprehend. Moreover, reference in the appended claims to an apparatus or system or a component of an apparatus or system being adapted to, arranged to, capable of, configured to, enabled to, operable to, or operative to perform a particular function encompasses that apparatus, system, component, whether or not it or that particular function is activated, turned on, or unlocked, as long as that apparatus, system, or component is so adapted, arranged, capable, configured, enabled, operable, or operative. For example, various embodiments may perform all, some, or none of the steps described above. Various embodiments may also perform the functions described in various orders.

Although the present invention has been described herein in connection with several embodiments; changes, substitutions, variations, alterations, transformations, and modifications may be suggested to one skilled in the art, and it is intended that the present invention encompass such changes, substitutions, variations, alterations, transformations, and modifications as falling within the spirit and scope of the appended claims.

Figure 1A:
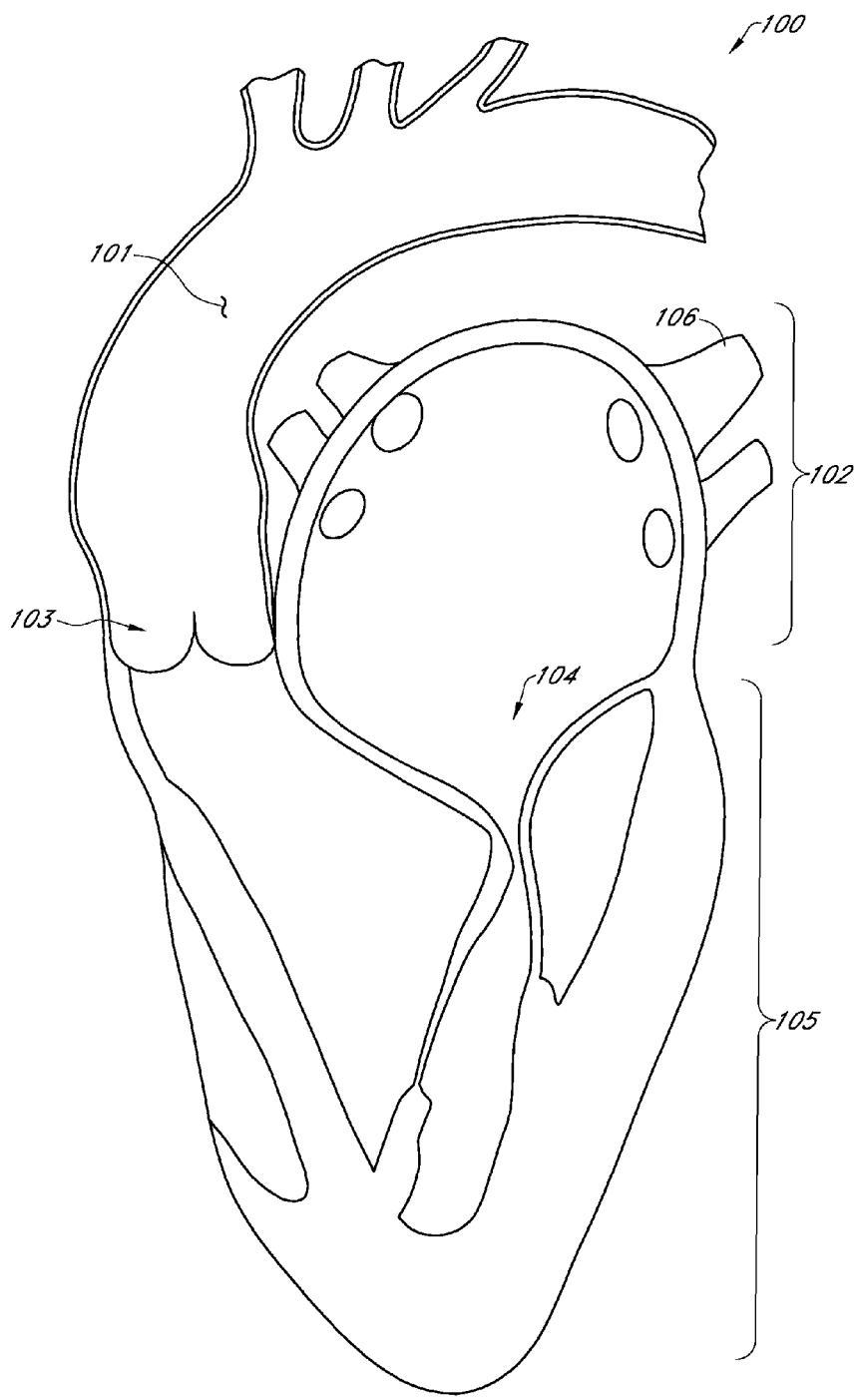
FIG. 1A illustrates an example heart showing the left ventricle and the left atrium along with associated anatomical landmarks.

FIG. 1A illustrates an example heart showing the left ventricle and the left atrium along with associated anatomical landmarks. Left atrium 102 receives oxygenated blood from the pulmonary veins (e.g., pulmonary vein 106). When left atrium 102 contracts, mitral valve 104 opens and blood leaves left atrium 102 through mitral valve 104 into left ventricle 105. When left ventricle 105 contracts, mitral valve 104 closes and aortic valve 103 opens. Blood then flows into aorta 101, which carries blood away from heart 100 to the rest of the body.

Figure 1B:
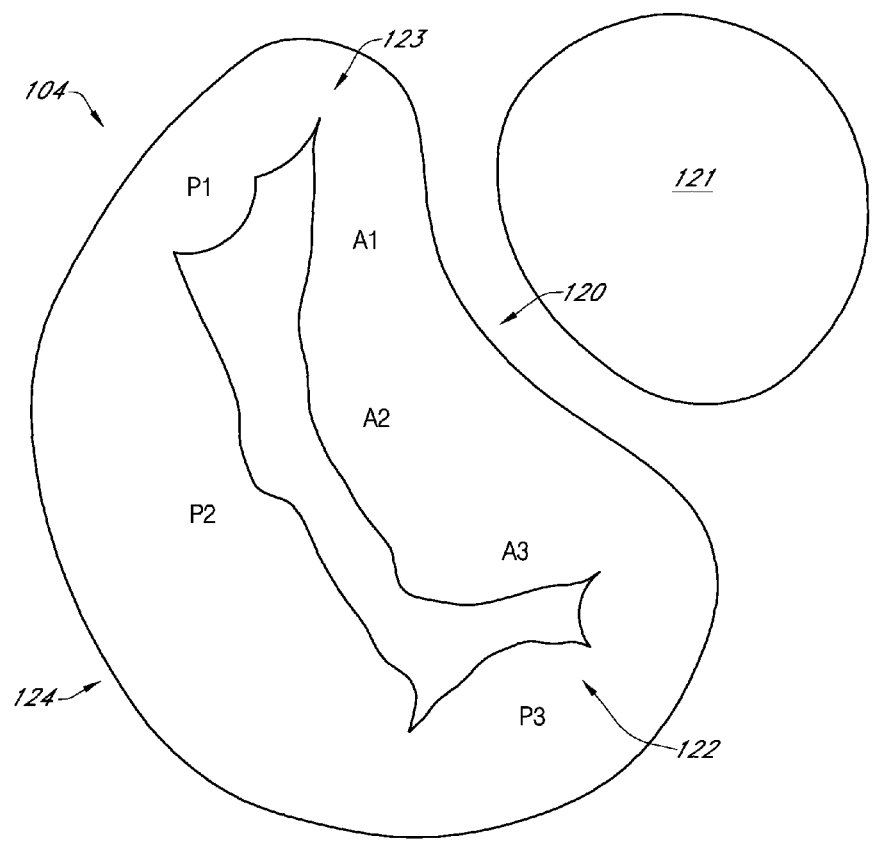
FIG. 1B illustrates a top-down view of the mitral valve of the example heart illustrated in FIG. 1A.

FIG. 1B illustrates a top-down view of the mitral valve of the example heart illustrated in FIG. 1A. Mitral valve 104 has two leaflets, anterior leaflet 120 and posterior leaflet 124. Anterior leaflet 120 is located proximal to aorta 121, and comprises of segments A1, A2, and A3. Posterior leaflet 124 is located distal to aorta 121, and comprises of scallops P1, P2, and P3. Scallops P1, P2, and P3 are extensions along the line of closure that allow the leaflets to accommodate the curved shape of the valve. Anterior leaflet 120 and posterior leaflet 124 come together at anterolateral commissure 123 and posteromedial commissure 122.

Mitral valve incompetence may occur when mitral valve 104 does not close properly when heart 100 pumps out blood. This can lead to blood regurgitating left ventricle 105 (FIG. 1A) back into left atrium 102 when left ventricle 105 contracts. The regurgitation may lead to symptoms including dyspnea, fatigue, orthopnea, and/or pulmonary edema.

Figure 2A:
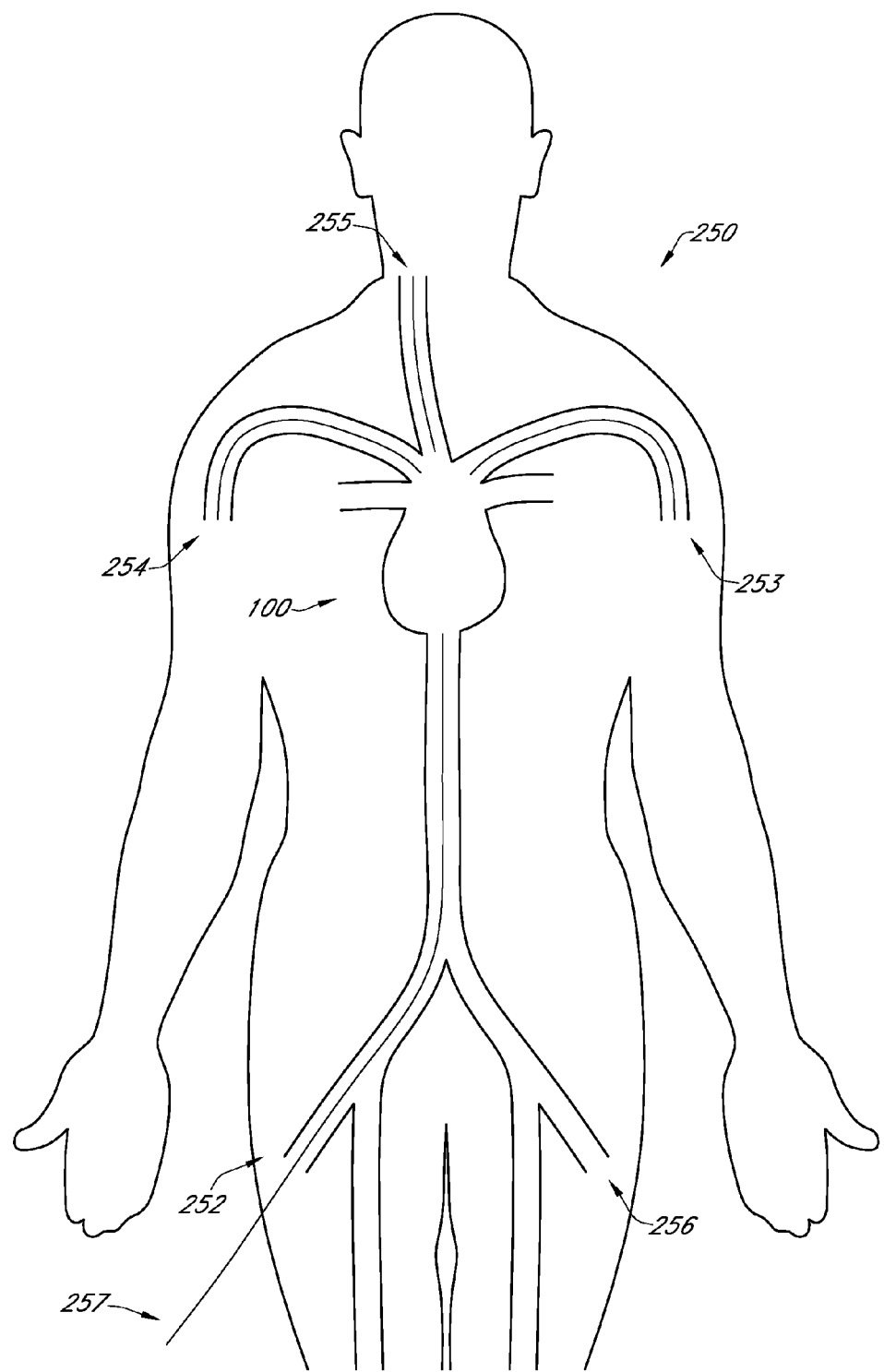
FIGS. 2A-2E illustrate example ways for introducing a delivery catheter to the mitral valve.

FIGS. 2A-2E illustrate example ways for introducing a delivery catheter to the mitral valve. FIG. 2A illustrates various common points of entry for a delivery catheter to access heart 100 of person 250. Delivery catheters may be used for delivering materials to a location of the body, including drugs, therapeutic treatments (e.g., energy for ablation), diagnostics, and/or implants. Typically, a delivery catheter has a long, flexible tubular portion that may be inserted into the lumens of arteries or veins. A person having ordinary skill in the art should appreciate that there are any number of entry points and/or ways that a delivery catheter may be inserted into the body. A few examples are described herein for illustration. A delivery catheter may be inserted into heart 100 percutaneously or through a cut-down procedure through the right or left femoral artery from point 252 or 256 in the legs and/or groin. A delivery catheter may also be inserted into heart 100 through the brachial arteries from points 254 and 253 in the arms. Another common entry point for a delivery catheter may be point 255 in the neck, which allows the catheter to be inserted into the jugular vein.

Figure 2B:
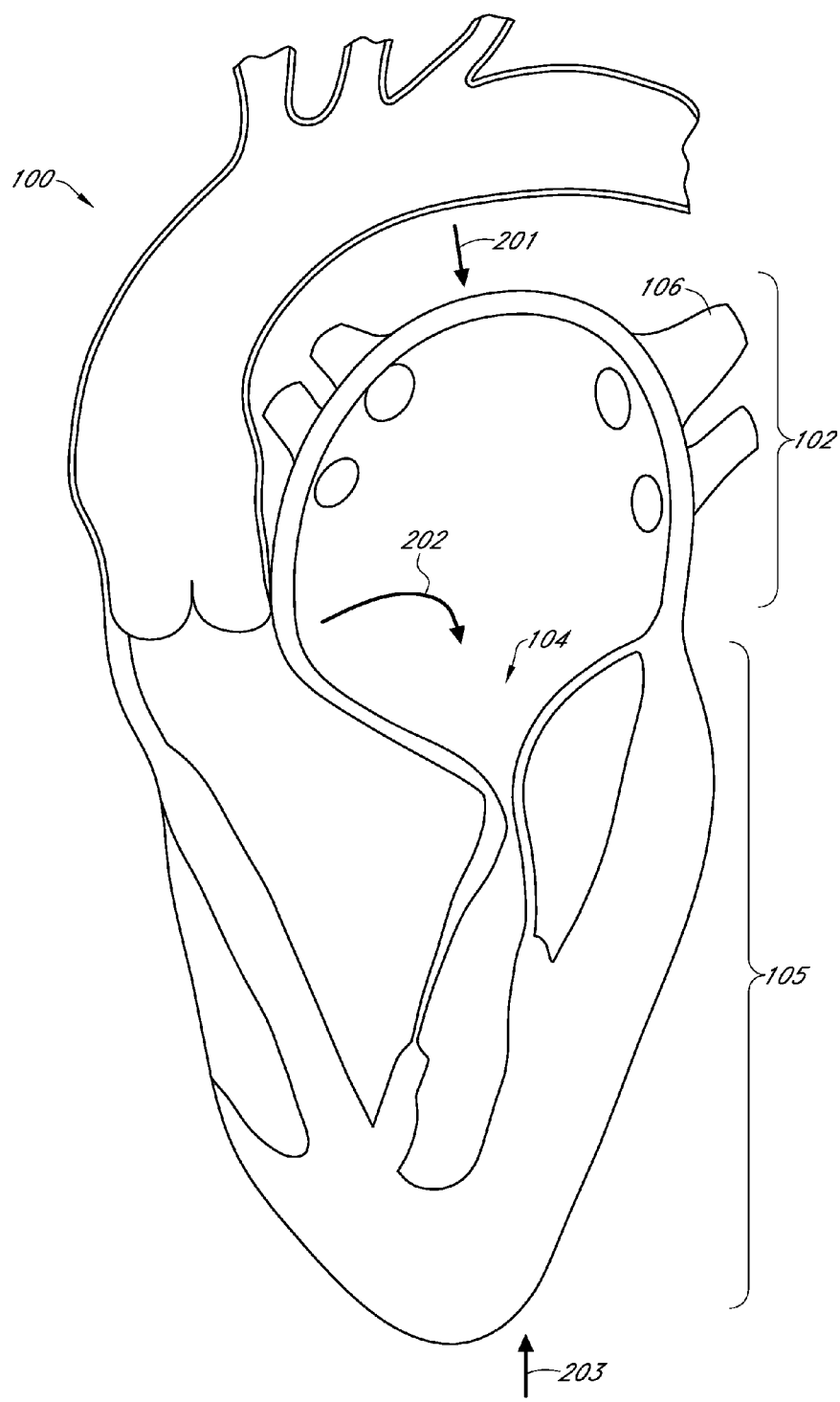

Once inserted into the body, FIG. 2B further illustrates common entry points for introducing a delivery catheter to mitral valve 104 of heart 100. Included are transseptal entry 202, transatrial entry 201, and transapical entry 203, which will be discussed in more detail.

Figure 2C:
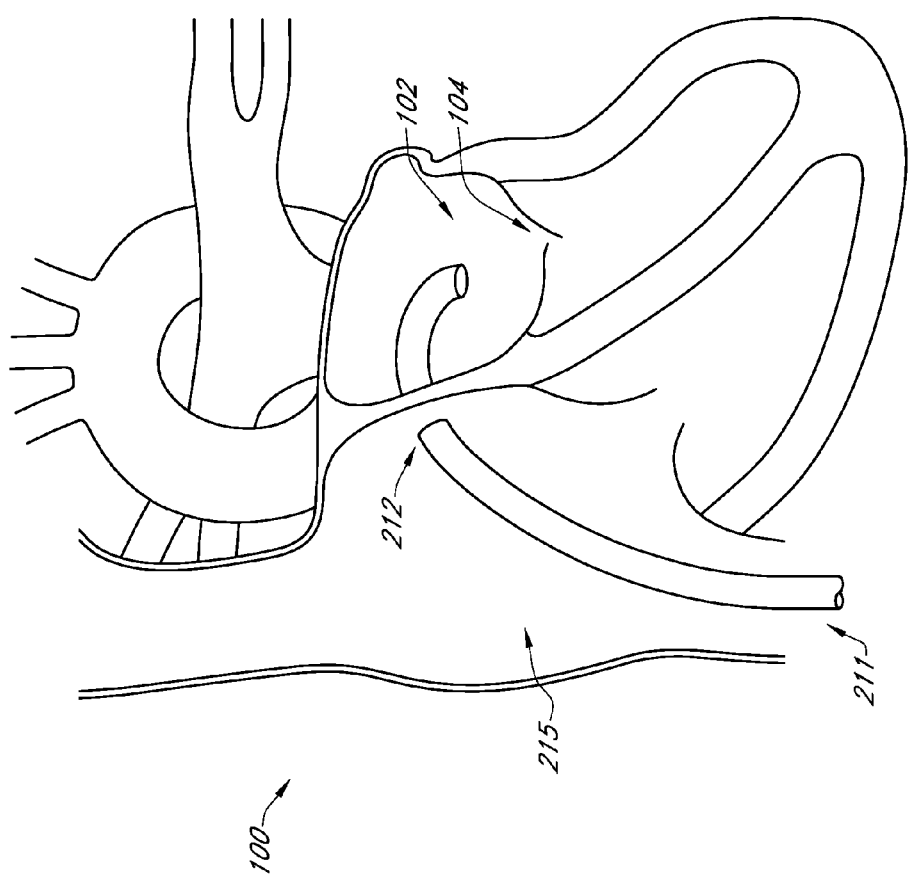

FIG. 2C illustrates an example transseptal entry. Delivery catheter 211 may be introduced to right ventricle 215 through a venous entry in the leg and/or groin. Delivery catheter 211 may then pass to left atrium 102 through transseptal puncture 212 in order to reach mitral valve 104.

Figure 2D:
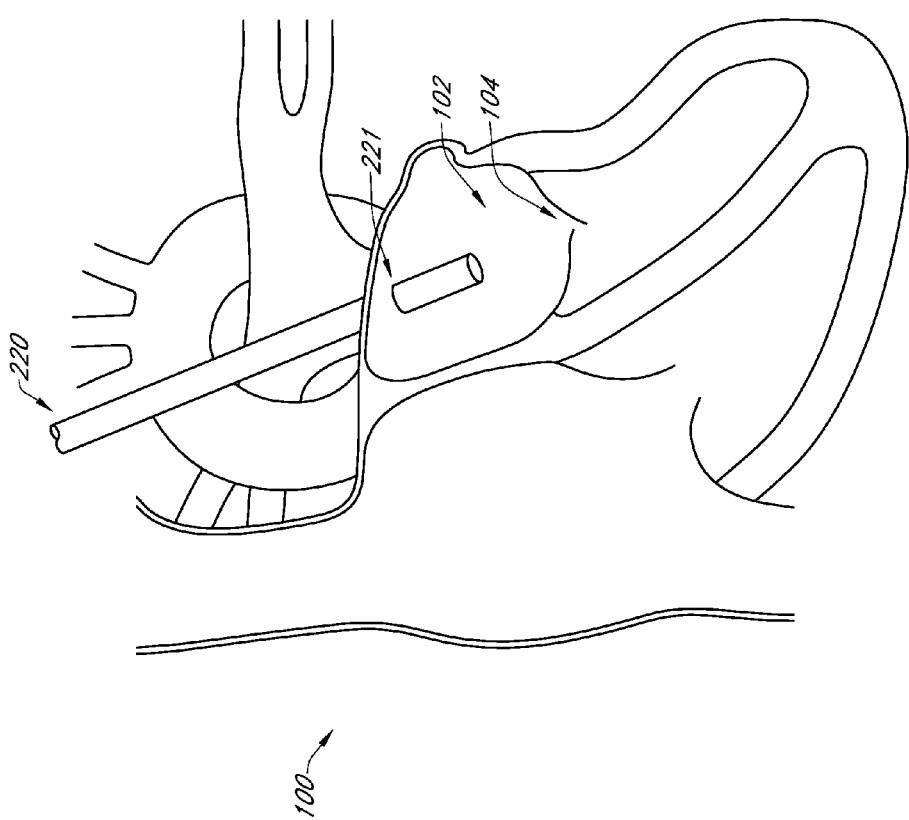

FIG. 2D illustrates an example transatrial entry. Delivery catheter 220 is introduced to heart 100 through puncture 221 in the wall of left atrium 102 to mitral valve 104. From left atrium 102, delivery catheter 220 may reach mitral valve 104.

Figure 2E:
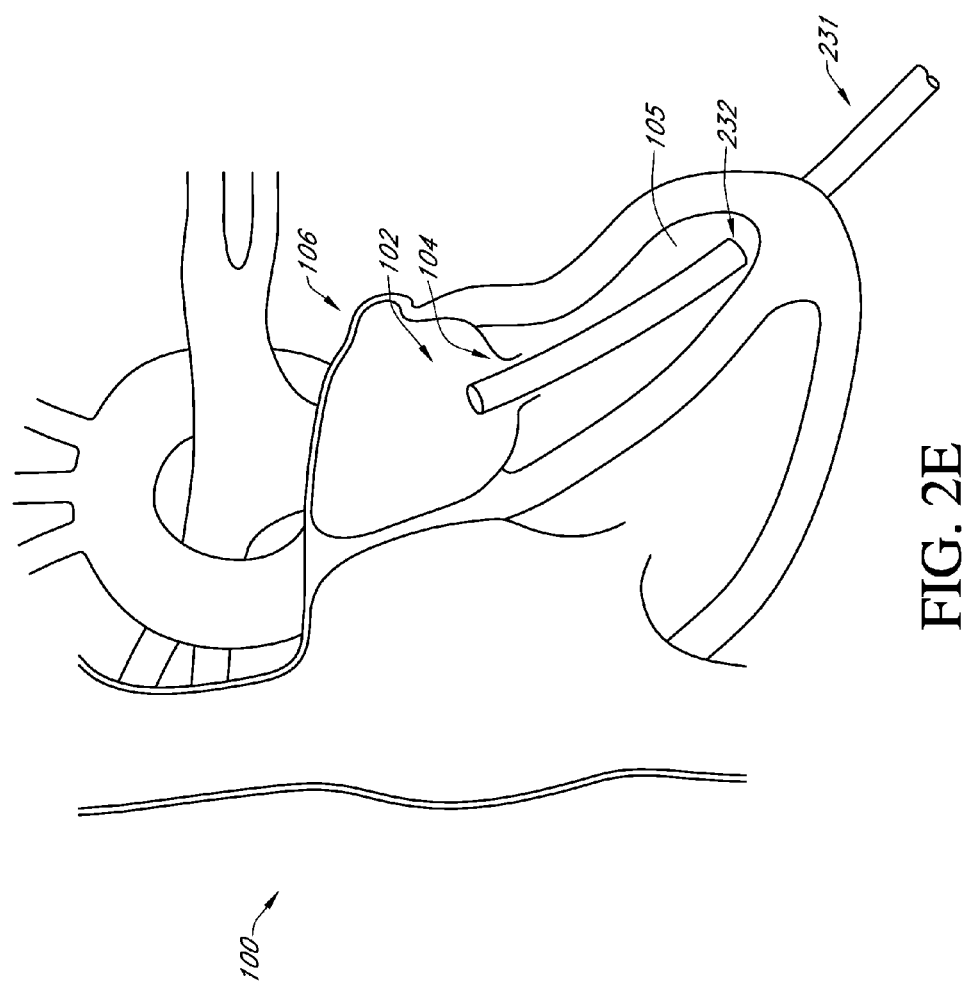

FIG. 2E illustrates an example transapical entry. Delivery catheter 231 is introduced through the apex of the heart through puncture 232 into left ventricle 105. From there, delivery catheter 231 may reach mitral valve 104 and left atrium 102.

There may be additional paths for reaching mitral valve 104. For example, a delivery catheter may reach mitral valve 104 through pulmonary vein 106. A delivery catheter may also use a transaortic entry. Embodiments of the present invention are not limited to any particular way of gaining access to the mitral valve. A person having ordinary skill in the art should appreciate that the methods and systems of this disclosure are not limited to any particular path(s) and may be readily adaptable to others not specifically described. However, the aforementioned entry points are a few illustrative examples of how embodiments of this disclosure may be introduced to mitral valve 104.

Figure 3:
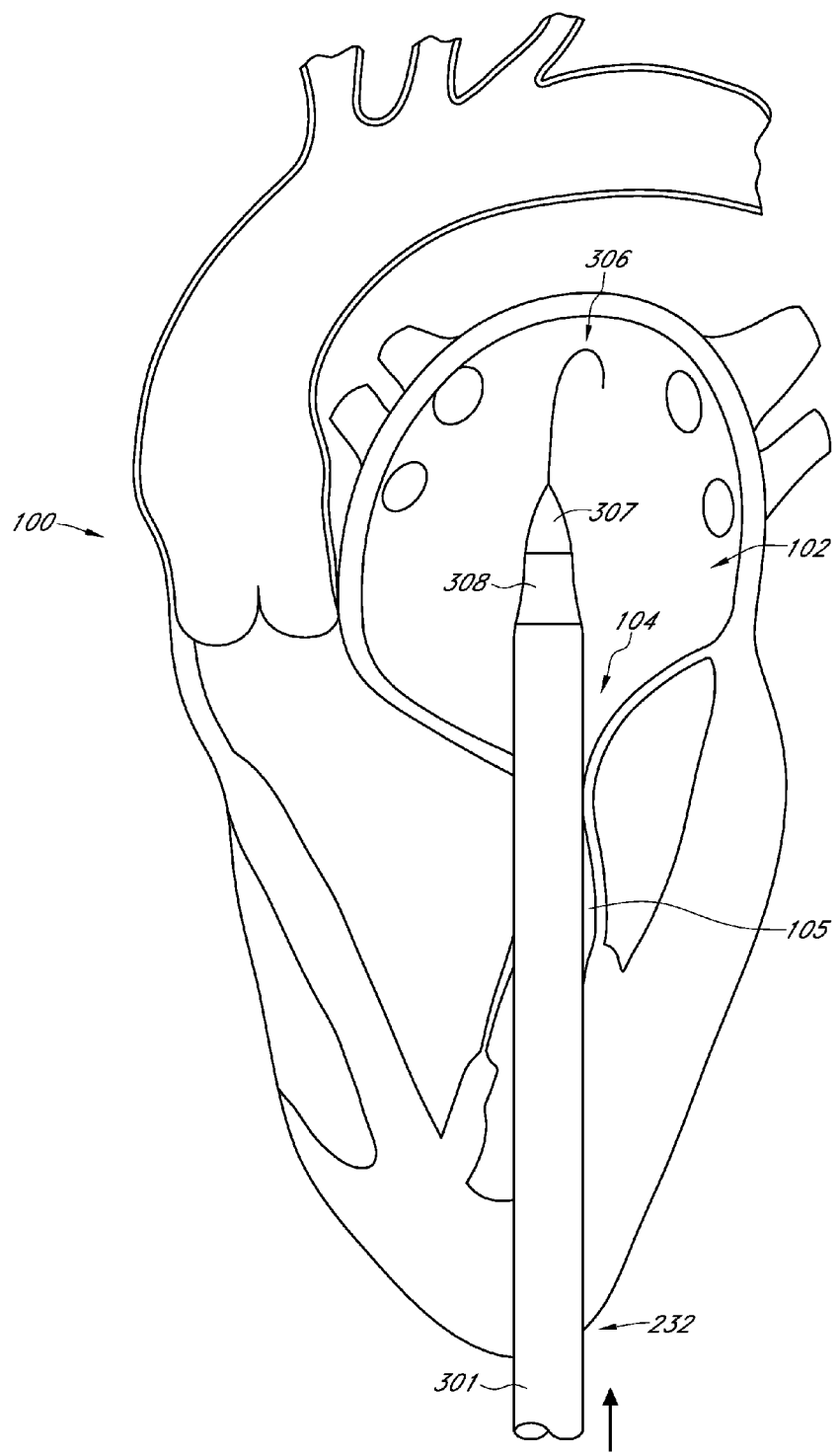
FIG. 3 illustrates a transapical entry through the left ventricle and mitral valve using a delivery catheter having a guidewire.

FIG. 3 illustrates a transapical entry through the left ventricle and mitral valve using a delivery catheter having a guidewire. Guidewire 306 may guide delivery catheter 301 into left ventricle 105 through puncture 232 at the apex of heart 100. From left ventricle 105, guidewire 306 may further guide delivery catheter 301 into left atrium 102 through mitral valve 104.

The implant (not pictured) may be carried in a compressed state at the distal end of delivery catheter 301 and housed in sheath 308, which can be an outer tubular jacket, during initial navigation. Such compression may be desirable in order to advance the implant in situ for positioning in the body via arterial or venous entry without having the implant interact with arterial or venous tissue, and/or any other tissue of the body before being delivered to left atrium 102.

The size of delivery catheter 301 may be, for example, generally within the range of about 10 to about 35 French in diameter, but may typically be about 24 French. Delivery catheter 301 may have a catheter length of about 45 to 100 centimeters in some embodiments. The proximal end of delivery catheter 301 may include a handle for operator interface and control. The handle may allow the implant, guidewire 306, and/or delivery catheter 301 to be manipulated within the body by curving tip 307 and angling the delivery catheter for accurate positioning. Alternatively, through axial, distal, and/or proximal advancement of one or more control wires or cables, tip 307 of delivery catheter 301 can be tensioned and/or deflected to alter the shape of the distal end of delivery catheter 301. Tip 307 may also be rotationally repositioned to match the anatomical needs for the target valve area or position. Guidewire 306 may pass through delivery catheter 301 and extend through tip 307. Guidewire 306 may aid in the navigation of delivery catheter 301. Guidewire 306 may measure, in some cases, from about 0.014 inches to 0.035 inches in diameter, but in some cases, the larger 0.035 inch in diameter may be preferable.

Figure 4:
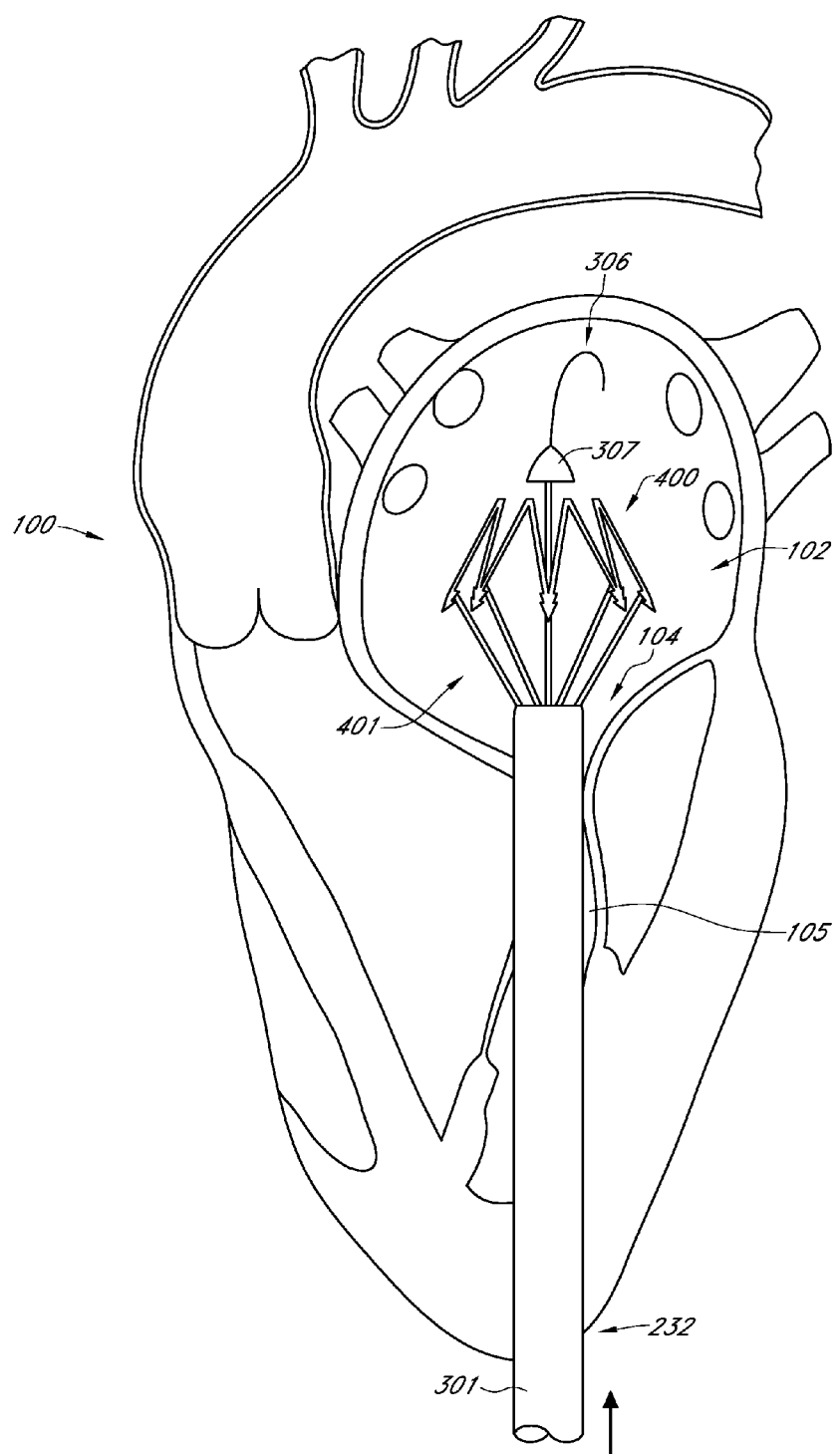
FIG. 4 illustrates an example exposed and/or unsheathed implant at the end of the delivery catheter of FIG. 3.

FIG. 4 illustrates an example exposed and/or unsheathed implant 400 at the end of the delivery catheter of FIG. 3. Implant 400 may be exposed and/or unsheathed by pulling back sheath 308 covering it, or alternatively pushing the implant distally past the sheath 308 in other embodiments. The covered state was illustrated in FIG. 3. Connection arms 401 run through delivery catheter 301 to implant 400 and allow for translation of forces for adjusting implant 400 and/or moving it around for positioning. These movements may include translational, rotational, and/or angular adjustments from the handle of delivery catheter 301. Connection arms 401 and delivery catheter 301 can be separated from implant 400, leaving the implant engaged in the heart after delivery and implantation.

Any implant of this disclosure (e.g., implant 400) may be constructed from, for example, metallic materials and/or polymers with sufficient structural integrity to reshape a mitral valve. The material may also be chosen based on biocompatibility and fatigue resistance. Implant material(s) could include stainless steel, Nickel-Titanium, Cobalt-Chromium, Pyrolytic Carbon, Nitinol, polymer materials (e.g., PEEK), and/or other suitable implant materials. In some cases, the implant may also be coated with drug-eluting material to prevent fibrosis and/or clotting.

The implant may be laser cut from a tubular member to form the basic shape. The implant may also be heat-set into a shape for further assembly, which may include the further steps of electrochemical etching and/or a secondary polishing to remove irregular and/or unwanted material. These further steps may be used to smoothen the surface of the implant. Alternatively, the implant could be formed from a wire that is fused together by a laser. The implant may generally comprise of a plurality of, for example sinusoidal strut elements joined at proximal and distal apexes to create a zigzag pattern. In some embodiments, the implant may comprise a frame comprising a plurality of struts connected to a plurality of anchors near the ends of the struts. The frame of the implant may include a central lumen therethrough. The struts may also form a diamond-shaped pattern similar to an expanded Palmaz coronary stent, or the strut arms could have a flat plateaued segment therebetween at the apex in some cases. In other words, the apices should have a sharp edge, a curved edge, or a flat top among other geometries. The implant could be configured to multiple shapes and sizes during processing, including its initial laser-cut, tubular shape and size, and a heat-set shape and size for further processing (e.g., polishing and assembling). The implant may have a central lumen therethrough.

In some embodiments, the initial tube from which the implant is cut may have an outside diameter that could vary from 4 to 10 millimeters in diameter, however, a diameter of about 8 millimeters could be used in most cases. The initial tube wall thickness may be about 0.008 to about 0.040 inches, but could typically be about 0.020 inches. The laser-cut implant with a sinusoidal shape may have an axial length of about 10 to 40 millimeters. In some cases, an axial length of about 20 millimeters may be used. The implant may have, for example, between 4 to 32 strut elements, however, typically 8 to 16 struts may be used.

The configuration of the laser-cut pattern could have a connected diamond pattern and/or a sinusoidal or other geometry with a plurality of integral or separately formed anchors comprising barbs and/or hooks to engage heart tissue for securement and/or permanent fixation. The anchors may extend distally from some and/or all of the struts and/or from the apexes of the struts. The anchors may be adapted to engage a dilated mitral annulus, and may be contractible either actively or passively with the implant, as will later be discussed. The anchors could also be internally or externally mounted to the implant allowing them to be covered or retracted during delivery and/or positioning. For tissue engagement, the anchors may utilize a single barbed element or a plurality of barbed elements.

Additionally, the barbed elements of each anchor could be of similar lengths and orientations, or various lengths and orientations depending upon the implant area tissue and surrounding sensitivity to tissue engagement. Additionally, the barbs could match the tubular shape of the as-cube tube, or be formed secondarily in and/or out of the tubular surface plane, which may angle the barb portion out of the cylindrical shape.

The implant could comprise one or more sinusoidal struts having eight curved apexes with eight anchors to engage the tissue at the distal end of the implant, where the anchors measure about 3 to 4 millimeters in length with 1, 2, 3, 4, or more barbs per anchor in some cases. The anchors may be further processed by twisting and/or rotating the anchors, their hooks, and/or their barbs after laser cutting. Such twisting and rotating may create more complex shapes (e.g., helical, tortious, and/or amorphous shapes) for improved tissue attachment in some cases.

The implant may be delivered in a first diameter and/or configuration, wherein the first diameter allows the implant to be carried within the sheath of the delivery catheter. In some cases, the implant may expand to a second diameter and/or configuration (e.g., by the retraction of the sheath and/or other mechanisms described in this disclosure), which would allow the implant to be expanded for positioning. Once desirably positioned, the implant could be attached by intimate tissue contact and/or force either longitudinally or radially outward. In some cases, such attachment would be performed by engaging the anchors of the implant to tissue surrounding and/or including the mitral valve. The implant may change size and/or shape to a third diameter and/or configuration after tissue engagement in order to change the shape of the mitral valve. The third diameter may be a reduced diameter in comparison to the second diameter, and could ease mitral regurgitation by pulling the tissue surrounding and/or including the mitral valve closer together, thereby reducing the mitral valve. Adjustments could be made to the implant by mechanisms coupled to the delivery catheter's handle located exterior to the patient.

Changes to the third diameter may be used to alter the geometry of the mitral valve area and its surrounding tissue. The natural opening of the mitral valve may not be a perfectly circular shape, but may be shaped more like a saddle with amplitude and ovality. Therefore, the final third diameter may not be perfectly circular, but may be more elliptical and/or amorphous with some customization required depending upon the patient's anatomy and the nature of the valvular incompetency. This customization can be achieved through selectively modifying the implant shape to better reduce the regurgitant flow through the patient's mitral valve. Echo imaging and/or fluoroscopy may indicate the desirable valve cooptation. The customization may include selectively and independently altering the sinusoidal element angles of the implant. For example, if the arms of one or more struts of the implant were moved closer to one another, the anchors connected to the arms of the one or more struts would also be moved closer to one another, which would move the mitral tissue attached to each anchor closer together. Numerous example mechanisms for such movements will be described in this disclosure.

As an example, the implant may be constructed from a Nitinol tubing measuring about 8 millimeters in diameter and laser-cut into a pattern allowing for expansion and heat-setting. The implant height could be about 10 to 30 millimeters and could vary around the perimeter to match the saddle shape of the mitral valve. The laser cut patterns include a sinusoidal or diamond shape allowing for the implant to be reduced to the first diameter of about 5-8 millimeters for loading into a delivery catheter. The implant may be expanded to a second diameter of about 25 to 50 millimeters for implantation into the tissue surrounding and/or including a mitral valve. The third diameter may be from about 20 to 25 millimeters to set the diameter of the mitral valve. The implant could be heat set into a round and/or cylindrical shape with tapering at the top and/or bottom to match the anatomical location. Accurate imaging by means of fluoroscopy and/or ultrasound imaging or other conventional imaging tools to view surrounding tissue and the implant delivery placement is typical and could be used for implantation and/or adjustment.

As will be described, for delivery, the implant may be connected to a delivery catheter by a plurality of receiver holes formed as part of the struts of the implant. The receiver holes may be designed to mate with a plurality of connection arms (e.g., connection arms 401) connected to the delivery catheter. The receiver holes can be an integral part of the implant structure or a secondary structure coupled to the implant that may or may not be implanted. The connection arms may have radial flexibility allowing the implant to expand to various diameters. The connection arms may join the implant to the delivery catheter and tilt the implant by lengthening and shortening the connection arms on opposing sides via handle adjustment. Such tilting may be induced for anatomical positioning and/or angular adjustments. The ability to tilt the implant before engaging the anatomy compensates for patient anatomical variability. In some embodiments, tilting can vary from minus 30 degrees to plus 30 degrees at any selected angle. Alternatively, the delivery catheter may be pre-shaped with a fixed angle to accommodate anatomical irregularities and/or variations from patient-to-patient. This angular adjustment could also occur through delivery catheter angle adjustments at the distal end through cable tensioning or bending of the distal end of the catheter to influence the angle.

Figure 5A:
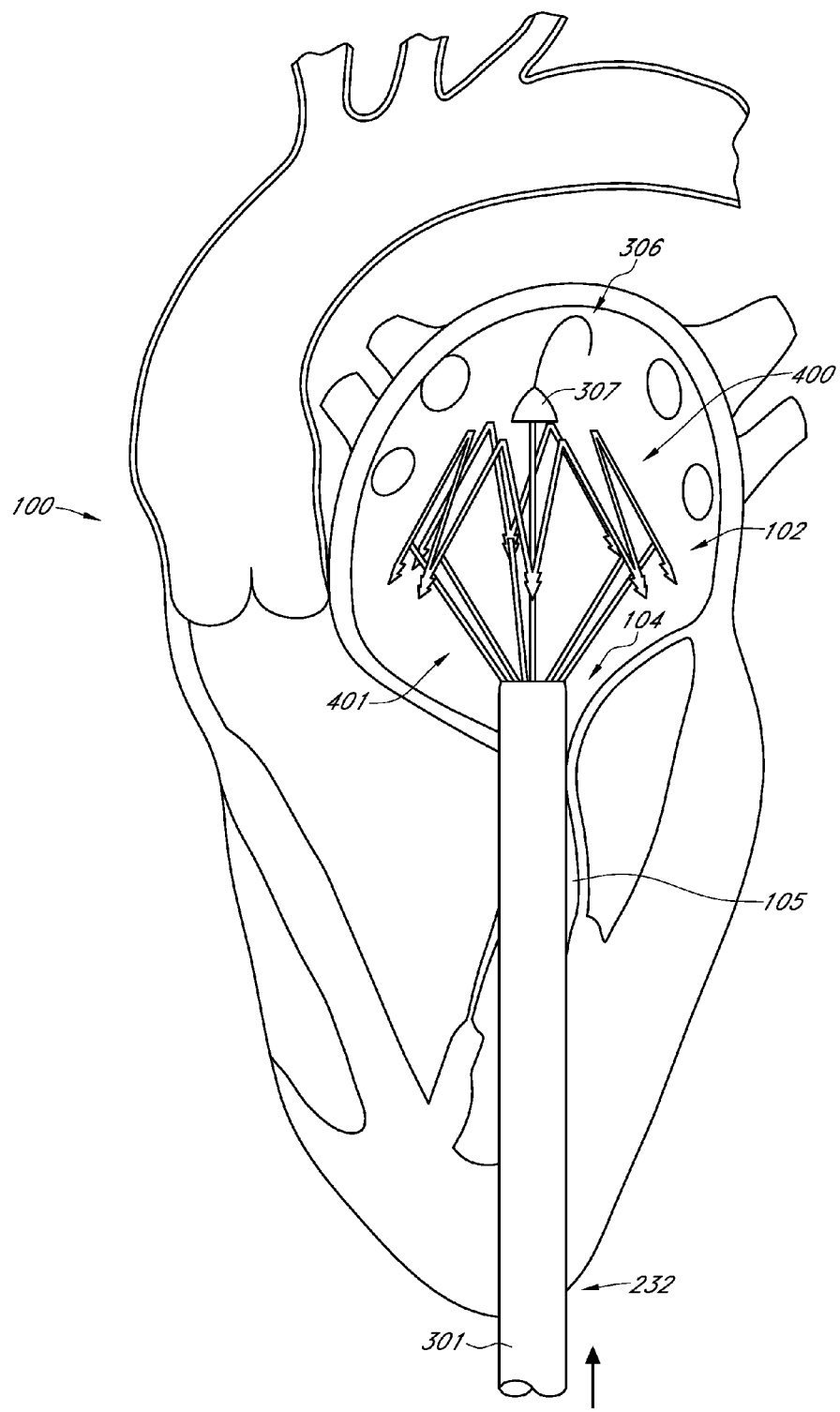
FIG. 5A illustrates the example implant of FIG. 4 in an expanded state.

FIG. 5A illustrates the example implant of FIG. 4 in an expanded state. This expansion could be activated with a force generated from the handle of delivery catheter 301 through the use of connection arms 401 and/or expandable members such as balloons (e.g., a balloon disposed within implant 400 and/or disposed within connection arms 401) to expand implant 400 to a desired diameter. The expansion could be uniform and/or circular, an elliptical shape, and/or amorphously shaped to match the anatomy of mitral valve 104. The expansion could also be tailored to match the patient's specific anatomical needs if an irregular shape were desirable. Once the implant is expanded, the protruding anchors of implant 400 may be embedded in the tissue surrounding and/or including the mitral valve by pulling or pushing implant 400, and/or any other mechanism described in this disclosure.

Figure 5B:
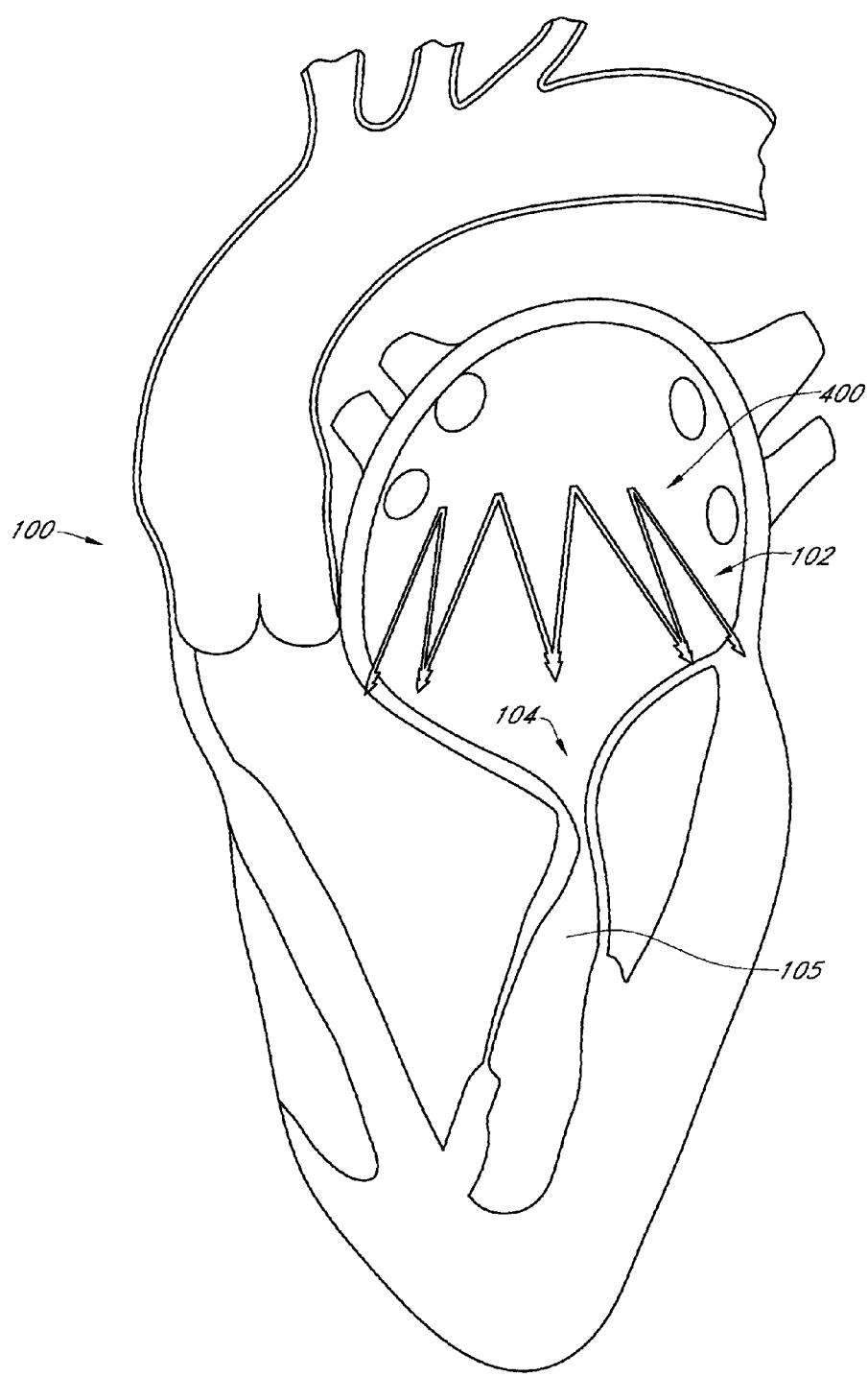
FIG. 5B illustrates the example implant of FIG. 5A embedded in the tissue surrounding and/or including the mitral valve.

FIG. 5B illustrates the example implant of FIG. 5A embedded in the tissue surrounding and/or including the mitral valve. Accordingly, implant 400 may be positioned so that it and mitral valve 104 may be reduced in diameter and/or dimension as desired. In some cases, the reduction of implant 400, and consequently mitral valve 104, could be achieved by passive forces through the hysteresis of the material of implant 400. For example, implant 400 may comprise of material(s) (e.g., Nitinol and/or any other material mentioned in this disclosure) that has an equilibrium size and/or shape that is smaller than the expanded state in which it is embedded into the tissue surrounding and/or including the mitral valve. As implant 400 returns to its equilibrium size and/or shape, a radially inward restoring force reduces both implant 400 and mitral valve 104, which in turn can reduce mitral regurgitation. In some embodiments, the mitral valve size and/or shape change can occur at the level of the proximal or distal end of the implant. In contrast to conventional annuloplasty rings which are implanted on an external cardiac surface, some embodiments as disclosed herein can operably attach to tissue on an internal (e.g., luminal surface) in the vicinity of the valve annulus.

As another example, the material of implant 400 may also be configured to react at body temperature to change its size and/or shape. The thermal expansion and retraction of the material may be used to apply the aforementioned passive forces. When the material (e.g., Nitinol or any other material mentioned in this disclosure) is heated, it expands, and when it is cooled, it retracts. In some embodiments, implant 400, or portions of implant 400, may be cooler than body temperature when implanted, and expand to a larger shape when it is warmed by body heat. At body temperature, implant 400 may then be the desired size and/or shape to attach to the tissue surrounding and/or including the mitral valve. Implant 400 may then be reduced and/or adjusted as desired by systems and methods described in this disclosure.

In the alternative, implant 400, or portions of implant 400, may be at a temperature warmer than body temperature when it is attached to the tissue surrounding and/or including the mitral valve. As implant 400, or portions of implant 400, cools to body temperature, the restoring forces may create an inward radial force that reduces both the size of implant 400 and mitral valve 104, which in turn can reduce mitral regurgitation.

In some cases, implant 400 is kept at a desired temperature (e.g., warmer or cooler than body temperature) before it is attached to delivery catheter 301. In this way, it may be warmer or cooler as it is delivered.

In some embodiments, delivery catheter 301 (FIG. 3) may also provide a microenvironment that helps hold the temperature of implant 400 before it is delivered to left atrium 102. In this way, it may allow implant 400 to be delivered at a temperature warmer or cooler than body temperature. For example, delivery catheter 301 may contain a heating coil, cooling elements, chemical heating/cooling, insulation, and/or any thermal control known in the art. In some embodiments, the implant can comprise magnetically controlled shape memory material (MSMs), including Fe—C, Fe—Pd, Fe—Mn—Si, Co—Mn, Fe—Co—Ni—Ti, Ni2MnGa, Co—Ni—Al, Ni—Mn—Ga, and the like. MSMs exhibit a paramagnetic/ferromagnetic transition besides a thermoelastic martensitic transformation. In some embodiments, the implant may be comprised of shape memory polymers (SMPs). Such SMPs may hold one shape in memory or may hold more than one shape in memory. SMPs which hold one shape in memory are generally characterized as phase segregated linear block co-polymers having a hard segment and a soft segment. The hard segment is typically crystalline, with a defined melting point, and the soft segment is typically amorphous, with a defined glass transition temperature. Sometimes, however, the hard segment is amorphous and the soft segment is crystalline. In any case, the melting point or glass transition temperature of the soft segment is substantially less than the melting point or glass transition temperature of the hard segment. Changes in temperature cause the SMP to revert between the original shape and the memory shape. Examples of polymers used to prepare hard and soft segments of SMPs include various polyethers, polyacrylates, polyamides, polysiloxanes, polyurethanes, polyether amides, polyurethane/ureas, polyether esters, and urethane/butadiene copolymers.

FIGS. 6A-L illustrate example structural details of various embodiments of the implant illustrated in FIGS. 5A-B. One or more of the structural details and variations illustrated may be used in different embodiments of the implant, and/or used in combination in a single embodiment. A person having ordinary skill in the art should also appreciate that any number of the adjustable restraints described may be used on implant embodiments to adjust the size and/or shape. The assortment of sizes and/or shapes presents a range (e.g., a working range) of configurations of the implant embodiments.

Figure 6A:
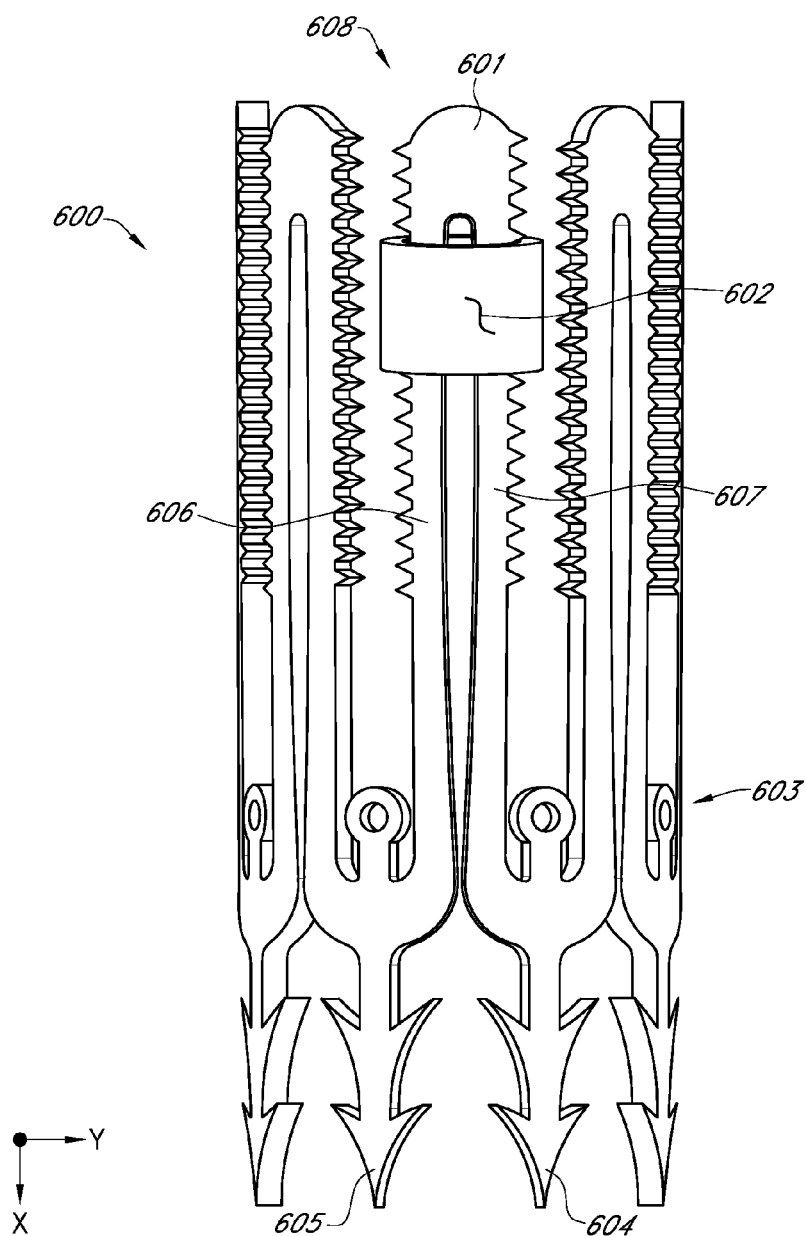
FIGS. 6A-L illustrate example structural details of various embodiments of the implant illustrated FIG. 5A-B.

FIG. 6A is a close-up view of a portion of an implant having a nut-and-thread mechanism for size and/or shape adjustment. In this embodiment, implant 600 comprises struts, such as strut 608. Strut 608 itself comprises of threaded crown 601 at its apex, and arms 606 and 607. Adjacently connected to arms 607 and 606 are anchors 604 and 605, respectively, such as at the base (e.g., the distal end) of the implant. Threaded crown 601 is encircled by nut 602, which can be used for customization of the size and/or shape of implant 600. For example, the positioning of nut 602 along threaded crown 601 may be used to adjust the relative positioning of anchors 604 and 605. When nut 602 is positioned closer to anchors 604 and 605 along strut 608, arms 606 and 607 may come closer together, which leads to anchors 604 and 605 coming closer together. Nut 602 may be positioned any number of ways, including by rotation, sliding, pushing, pulling, and/or any means of mechanically driving the nut. Other nuts like nut 602 may encircle the other threaded crowns of struts of implant 600. In this way, these nuts may independently position other anchors. In some cases, such positioning occurs after the anchors are embedded in the tissue surrounding and/or including a mitral valve. Through the manipulation of these nuts and struts, and consequently the anchors connected to those struts, implant 600 may be manipulated and/or adjusted as desired to shape mitral valve 104 as desired. It should be appreciated by one of ordinary skill in the art that the independent adjustments of these nuts permit implant 600 to be sized and/or shaped in many different ways. Such ability to shape implant 600 may be clinically desirable in patients with mitral regurgitation needing nonsymmetrical annular adjustment. It will not, however, prohibit symmetrical adjustment if desired. Rather, independent adjustments allow a physician or operator to adjust implant 600 to best suit the patient's regurgitant flow reduction. In some embodiments, the threads and/or nuts can be configured to extend a length axially along one, two, or more of the struts, such as at least about, about, or no more than about 10%, 20%, 30%, 40%, 50%, 60%, 70%, 80%, or 90% of the amplitude of the struts (e.g., the length of the device along its longitudinal axis).

Nut 602, or other nuts, may be circular, non-circular, an oval, amorphous, and/or any shape and/or size to conform to the shape of the struts. It may be constructed from material(s) including stainless steel, Nickel-Titanium, Cobalt-Chromium, Pyrolytic Carbon, Nitinol, polymer materials (e.g., PEEK), and/or other suitable implant materials.

Implant 600 may also have a plurality of receiver holes (e.g., aperatures), such as receiver hole 603, which may also be used to manipulate implant 600. Receiver holes may be in any number of orientations, including vertically positioned as in FIG. 6A, horizontal, angled, etc. with respect to the long axis of the implant. They may be located anywhere along the struts, anchors, and/or implant as desired, aligned horizontally in a ring formation, staggered and axially offset, and the like.

Figure 6B:
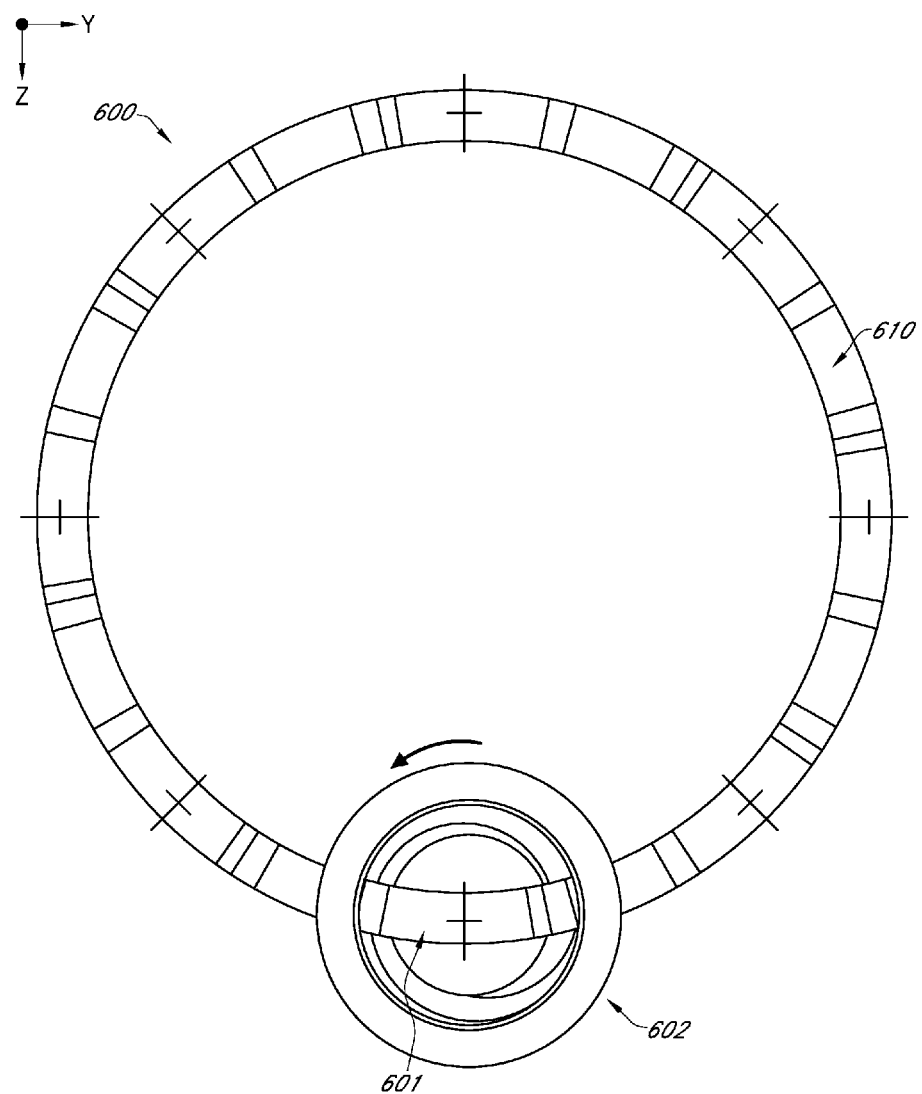

FIG. 6B is an above (top)-view of FIG. 6A and illustrates an example way of adjusting the shape of an embodiment of implant 600 through the rotation nut 602. Nut 602 is positioned on threaded crown 601 of strut 608. The threads may be configured such that the rotation of nut 602 repositions nut 602 on threaded crown 601, thus adjusting the position of arms 606 and 607, and consequently anchors 604 and 605 (FIG. 6A). For example, the threads of threaded crown 601 may be angled and/or otherwise configured to resemble the threads of a screw. The rotation of nut 602 could be driven through by the external handle of the delivery catheter and transmitted through a shaft, rod, and/or tube that connects to nut 602. Again, other nuts may be used to move other anchors, such as anchor 610.

Figure 6C:
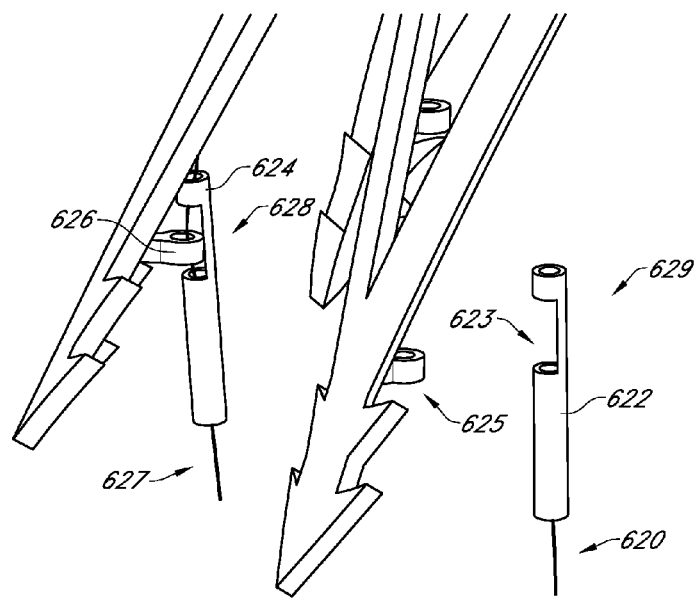

FIG. 6C illustrates a close-up of an example mechanism for connecting and/or separating connection arms from implants. In this embodiment, an implant (e.g., implant 400) has horizontal receiver holes (e.g., receiver holes 626 and 625) on the interior of the implant. A plurality of connection arms may be connected to the receiver holes of the implant during delivery. These connection arms may reversibly or detachably connect the implant to the delivery catheter, and may be used to initially expand the implant to the second diameter previously described.

It may be desirable to disconnect the connection arms from the implant at some time. For example, such a disconnection may be desirable after the implant has been positioned and the anchors of the implant have been embedded in the tissue surrounding and/or including a mitral valve, and the implant has been adjusted. Disconnection at this time would allow the connection arms and delivery catheter to be removed from the body, leaving only the implant. The separation of the connection arms from the implant may be performed independently for each receiver hole, or performed on all receiver holes of the implant simultaneously.

The connection arms may comprise a plurality of tubular members with wires. The tubular members and wires may interact with the receiver holes of the implant while the implant is connected to the connection arms. For example, tubular member 624 is positioned around receiver hole 626 such that wire 627 passes through tubular member 624 and receiver hole 626. Wire 627 may be held in place by a clip, hook, snag, loop, knot, magnet, adhesive, and/or any other mechanism(s) known in the art for holding a wire in place. In such a position, connection arm 628 is connected to the implant. Wire 627 can also be cut, electrolytically detached, or otherwise detached.

Connection arm 629 is disconnected. Tubular member 622 has been removed so that wire 620 no longer passes through receiver hole 625. Accordingly, tubular hole 623 of tubular member 624 is no longer held in position around receiver hole 625.

Figure 6D:
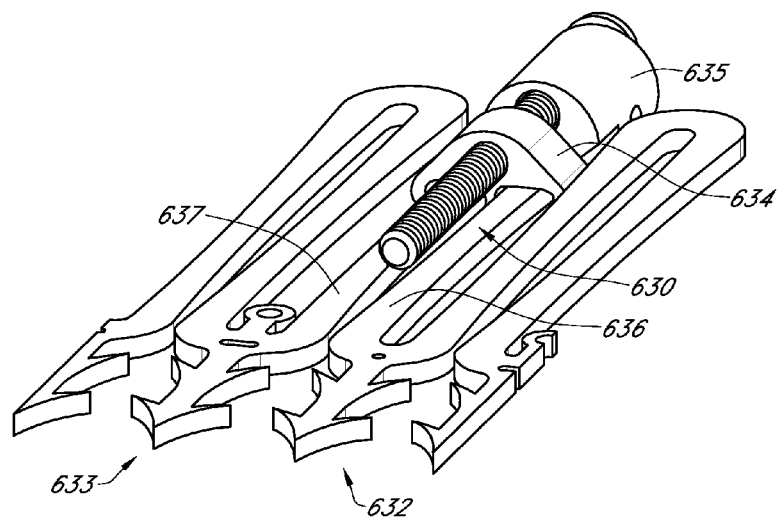

FIG. 6D illustrates an implant embodiment that may be adjusted in size and/or shape using a screw-and-clip mechanism. Clip 634 is placed over a strut having arms 636 and 637. The positioning of clip 634 along arms 636 and 637 may be adjusted by screw 630, which passes through boss 635 (e.g., a screw retainer) and clip 634. Clip 634 is threaded such that the rotation of screw 630 moves clip 634 up and down. For example, clip 634 may have threads that run in the opposite direction as the threads of screw 630.

As clip 634 moves down arms 636 and 637, arms 636 and 637 move closer together, which causes anchors 632 and 633 to gather closer to one another. In this way, clip 634 may be used to adjust the size and/or shape of an implant. A person having ordinary skill in the art should recognize that an implant may have a plurality of screw-and-clip mechanisms, such as the one just described, connected to a plurality of struts. By positioning the clips, independently or simultaneously, the size and/or shape of the implant may be adjusted as desired.

The screw-and-clip mechanism may be attached to the outer diameter or the inner diameter of the implant, and could use a single or a plurality of screws and clips, depending upon the implant crown quantity and/or as desired. The threaded members of the screws and clips may measure from, in some embodiments, about 0.4 millimeters in diameter to about 1.5 millimeters and be constructed from stainless steel, Nickel-Titanium, Cobalt-Chromium, Pyrolytic Carbon, Nitinol, polymer materials (e.g., PEEK), and/or other suitable implant materials. In some cases, a #2-56 thread size may be used.

Figure 6E:
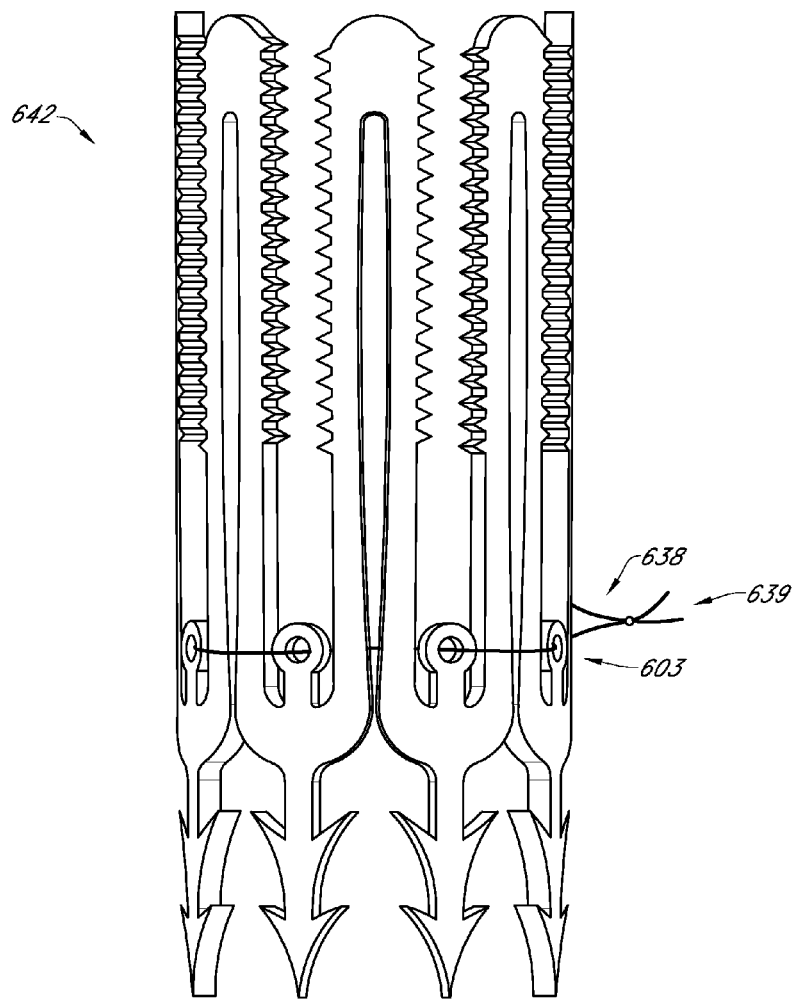

FIG. 6E illustrates a cable mechanism that may be used to adjust the size and/or shape of an implant embodiment. In some embodiments, cable 638 encircles implant 642, e.g., in a direction transverse or oblique to the longitudinal axis of the implant and applies a radially restrictive force on implant 642, which may be used to control the size and/or shape of implant 642. Cable 638 may pass through a plurality of the receiver holes of implant 642 (e.g., receiver hole 603). Cable 638 may be a thread, suture, cable, string, wire, ribbon, and/or any sort of structure that could pass through the receiver holes (e.g., receiver hole 603) of implant 642. Cable 638 may be tied off at knot 639. In some cases, knot 639 may be a moveable knot (e.g., a slip knot) that allows the length of cable 638 to be adjusted. For example, force may be applied to knot 639 to pull or push it (e.g., medially or laterally) such that cable 638 shortens or lengthens. Force may also be applied to one or more points of cable 638, including the ends of cable 638, in order to pull portions of cable 638, thereby shortening or lengthening cable 638. The force may be applied through mechanical drivers and/or actuators, wherein the force is applied through the delivery catheter from the handle of the delivery catheter.

In some embodiments, cable 638 may also be shortened by wrapping portions of the cable around a spool/ream. For example, portions of cable 638 may initially wrap around the spool/ream during delivery, and the spool/ream may be rotated in order to cause more/less of cable 638 to wrap around it. The rotation may be performed by a rotational driver (e.g., the rotational drivers illustrated in FIGS. 13-15). In this way, cable 638 may be shortened or lengthened.

Again, receiver holes or apertures (e.g., receiver hole 603) may be positioned in various places on implant 642, angles, and/or configurations. The receiver holes may also be placed uniformly or non-uniformly across implant 642. For example, receiver holes may be adjacent to every anchor of implant 642 or adjacent to fewer than every anchor of implant 642 in order to achieve the desired shape and/or size of implant 642.

Figure 6F:
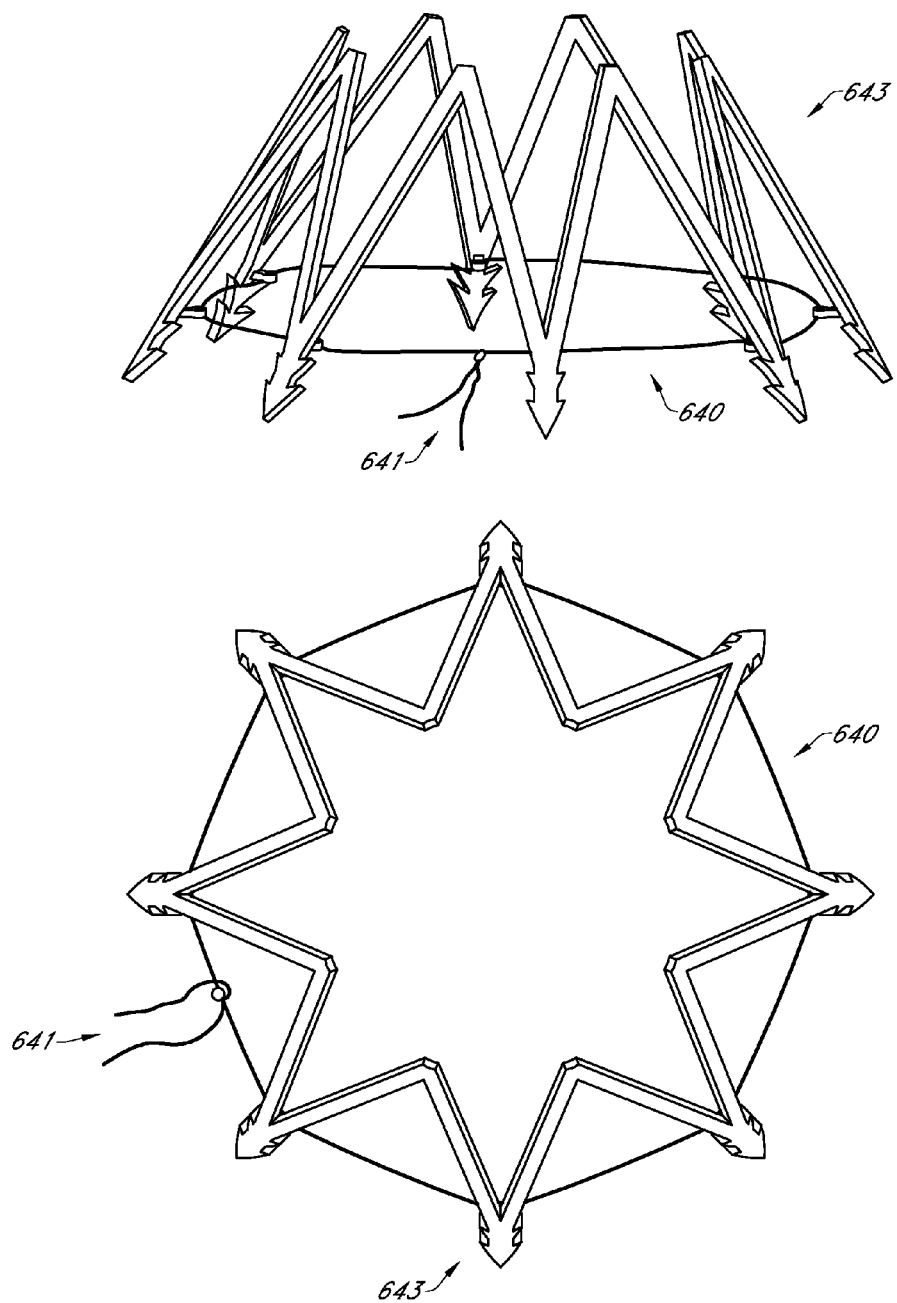

FIG. 6F illustrates a top-view and a side-view of an implant embodiment. In this embodiment, implant 643 has horizontal receiver holes on its interior. As illustrated, cable 640 passes through all the receiver holes of implant 643. However, cable 640 may also pass through a number of receiver holes less than all of the receiver holes of implant 643. The shape and/or size of implant 643 may be adjusted by loosening or tightening cable 640 using any system and/or method of loosening and/or tightening cables described in this disclosure. Typically, cable 640 remains with implant 643 after implant 643 has been implanted in order to maintain the shape and/or size of implant 643. However, cable 640 may also be removed and/or disconnected from implant 643 as desirable.

Figure 6G:
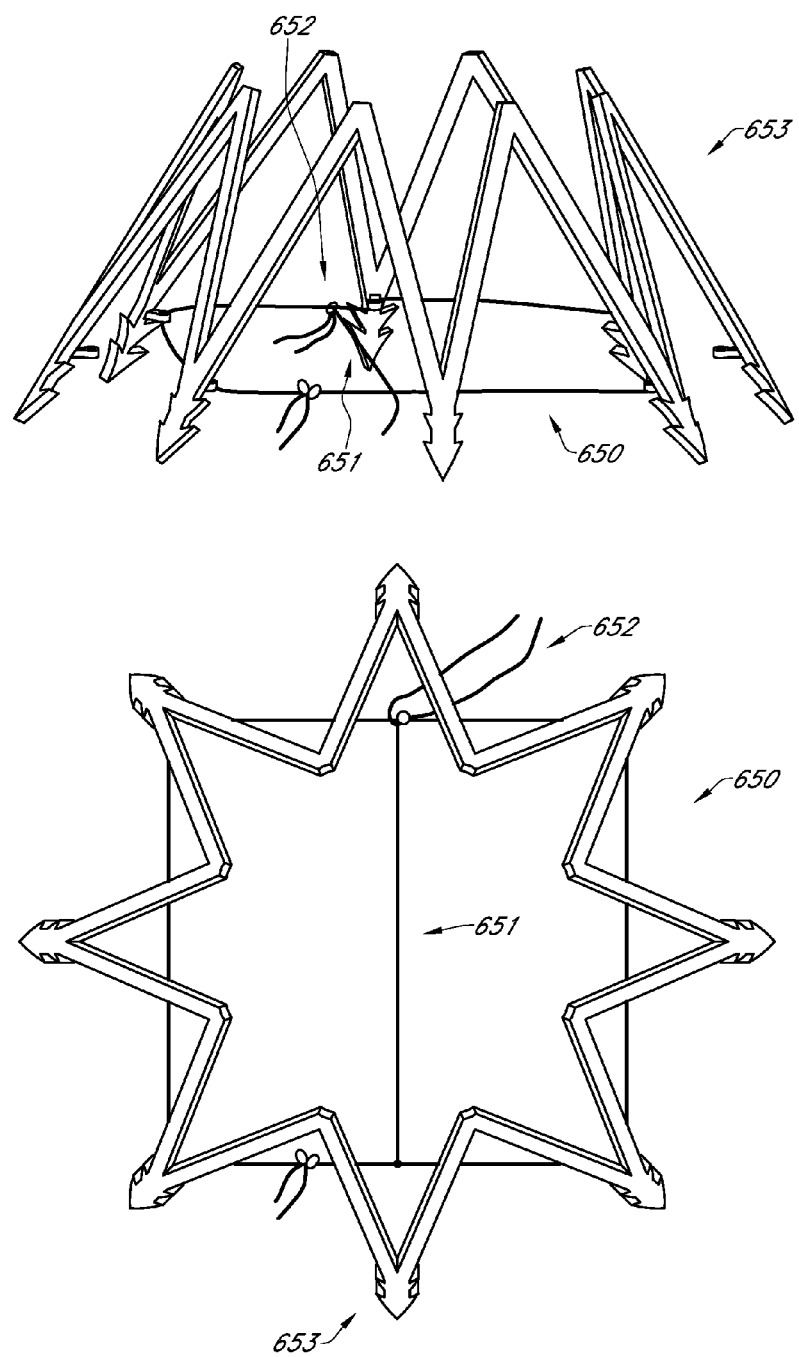

FIG. 6G shows a side-view and a top-view of an implant embodiment using a cable mechanism with a cross-cable oriented in a direction other than around an outer diameter or an inner diameter of an implant, such as traversing the outer diameter or inner diameter of an implant. In this embodiment, cable 650 passes through some, but not all, of the receiver holes of implant 653. Additionally, cross-cable 651 is used to connect segments of cable 650, and may or may not pass through a receiver hole. Cross-cable 651 may be connected to cable 650 by knots, such as knot 652, which may be moveable knots (e.g., a slip knot) that allow the length of cross-cable 651 to be adjusted. For example, force may be applied to knot 652 to pull or push it (e.g., medially or laterally) such that cross-cable 651 shortens or lengthens. Force may also be applied to one or more points of cross-cable 651, including the ends of cross-cable 651, in order to pull cross-cable 651 laterally, thereby shortening or lengthening cross-cable 651. The force may be applied through mechanical drivers and/or actuators, wherein the force is applied through the delivery catheter from the handle of the delivery catheter. Just like cable 640, cross-cable 651 may also be adjusted by using a spool/ream connected to a rotational driver (e.g., the rotational drivers illustrated in FIG. 13-15), wherein the rotation of the spool/ream causes more/less of cross-cable 651 to wrap around it. This may change the length of cross-cable 651.

It should be appreciated by one having ordinary skill in the art that a cable may pass through different receiver holes in order to adjust implant 653 as desirable. Having a plurality of receiver holes allows variability in the shape and/or size of implant 653 using cables. Cross-cables, such as cross-cable 651, may also allow further variability in shape and/or size of implant 653. For example, having a cross-cable may allow a precise adjustment along a particular plane as the cross-cable is shortened and/or lengthened. Cross-cables may be placed anywhere along a cable as desired.

Figure 6H:
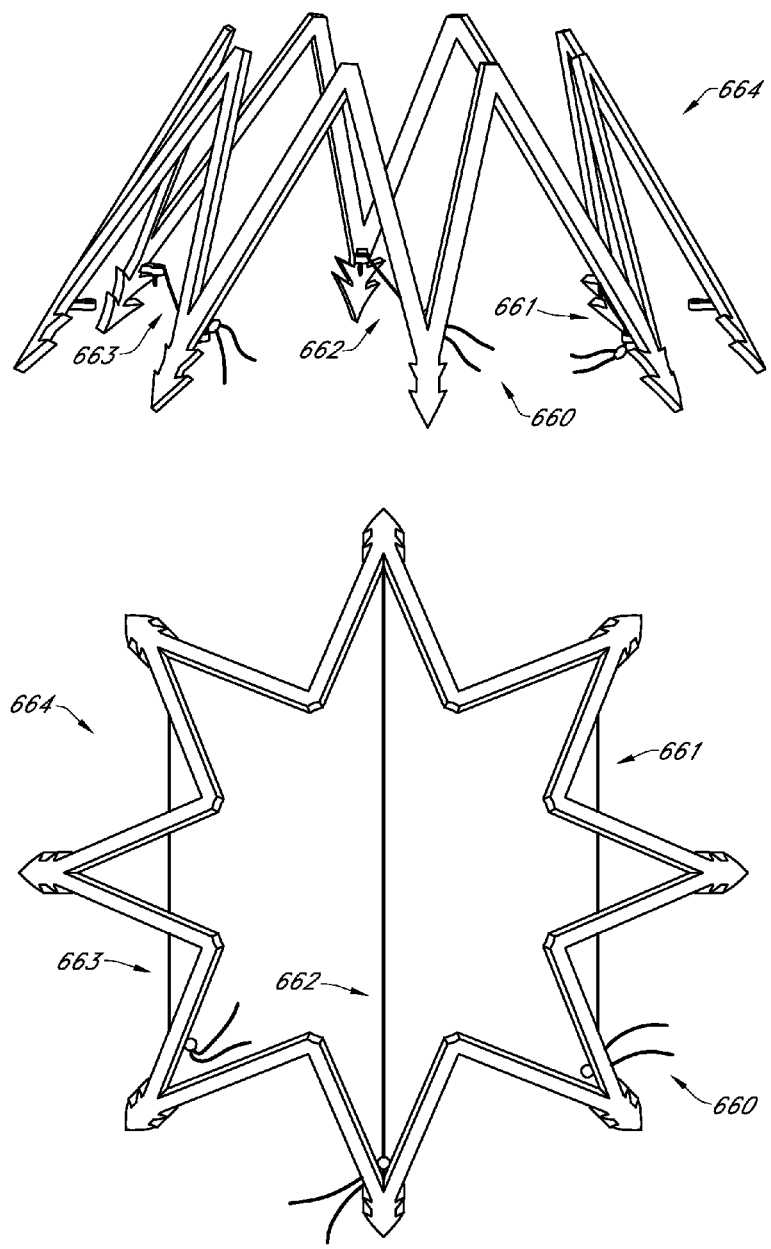

Even more variability in shape and/or size of an implant may be achieved by further variations in cable configurations. For example, a plurality of independent cables may be used to connect various receiver holes of an implant. FIG. 6H illustrates an implant embodiment having a plurality of independent cables. Cables 661, 662, and 663 independently connect various receiver holes of implant 664. They may be connected to the receiver holes by knots, such as knot 660. The shape and/or size of implant 664 may be adjusted by loosening or tightening one or more of cables 661, 662, and 663 using any system or method of loosening and/or tightening cables described in this disclosure. In other embodiments, independent cables may cross each other and/or be configured to connect any receiver hole with another. In some cases, a single receiver hole may be connected to more than one cable. In some embodiments, the cables do not completely follow the outer diameter or inner diameter of the implant.

Figure 6I:
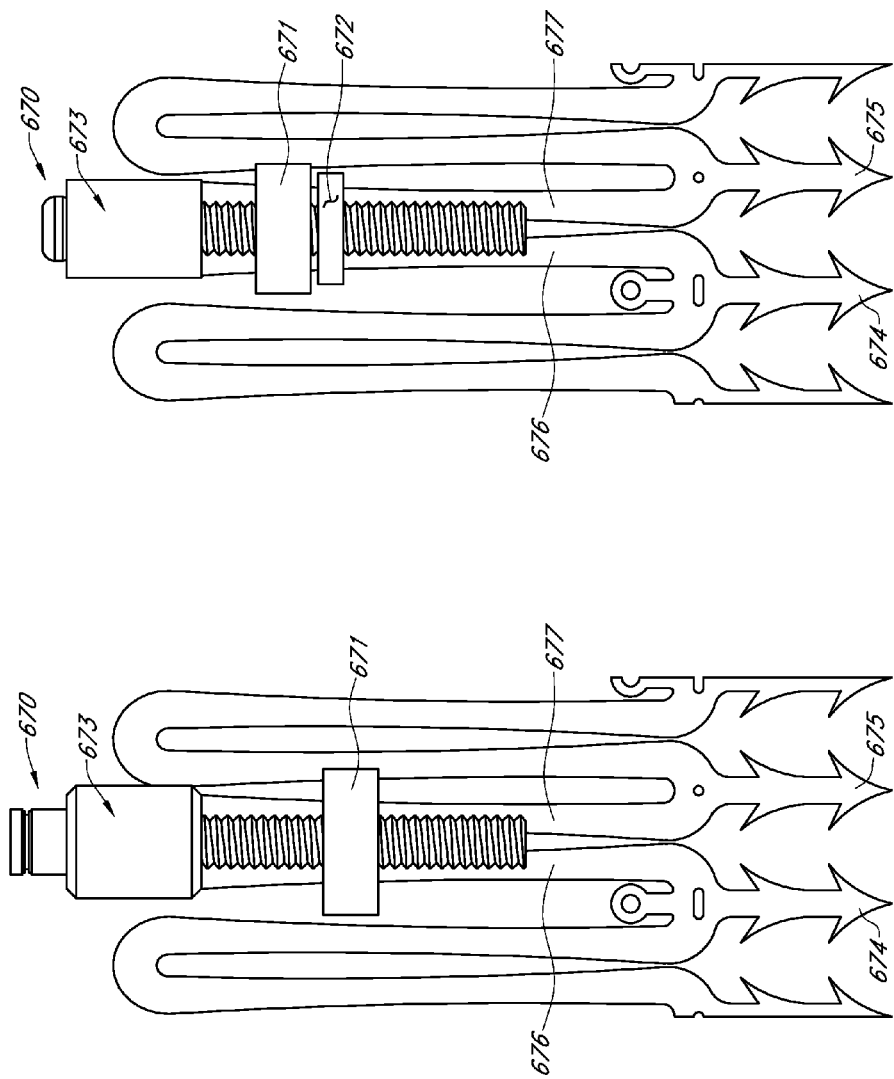

FIG. 6I illustrates an alternative that may use a similar screw-and-clip mechanism as FIG. 6D. The screw-and-clip mechanism uses screw 670, clip 671, and boss 673. The screw may vary in size depending on the size of the implant and/or as desired. In some embodiments, locking ring 672 may be positioned distally to clip 671, where locking ring 672 locks the strut arms 676 and 677 in position, and consequently locks the position of anchors 674 and 675. Locking ring 672 may remain on the implant after screw 670, boss 673, and/or clip 671 have been removed.

There are a number of ways locking ring 672 may be positioned. In some embodiments, locking ring 672 is initially within clip 671. Locking ring 672 may be configured such that it stays in place along arms 676 and 677 once it has been advanced. For example, locking ring 672 may have directional fasteners, cogs, and/or tangs that only allow it to move downward (e.g., advance) arms 676 and 677. As screw 670 is turned in one direction, locking ring 672 advances down arms 676 and 677. Once locking ring 671 is positioned, screw 670 may be turned in the other direction to remove screw 670, clip 671, and/or boss 676, and leave locking ring 671.

In other embodiments, clip 671 and/or locking ring 672 may be positioned by a cable (e.g., thread, suture, cable, string, wire, etc.). For example, clip 671 and/or locking ring 672 may be connected to a cable. The cable may thread through a single or plurality of holes located on arm 676, and then up through holes located on clip 671 and/or locking ring 672. The cable could then connect back down through another hole located on arm 677. When pulled, the cable may force clip 671 and/or locking ring 672 down arms 676 and 677, which in turn positions anchors 674 and 675. The cable could subsequently be removed, leaving clip 671 and/or locking ring 672 behind holding arms 674 and 675 in position.

Figure 6J:
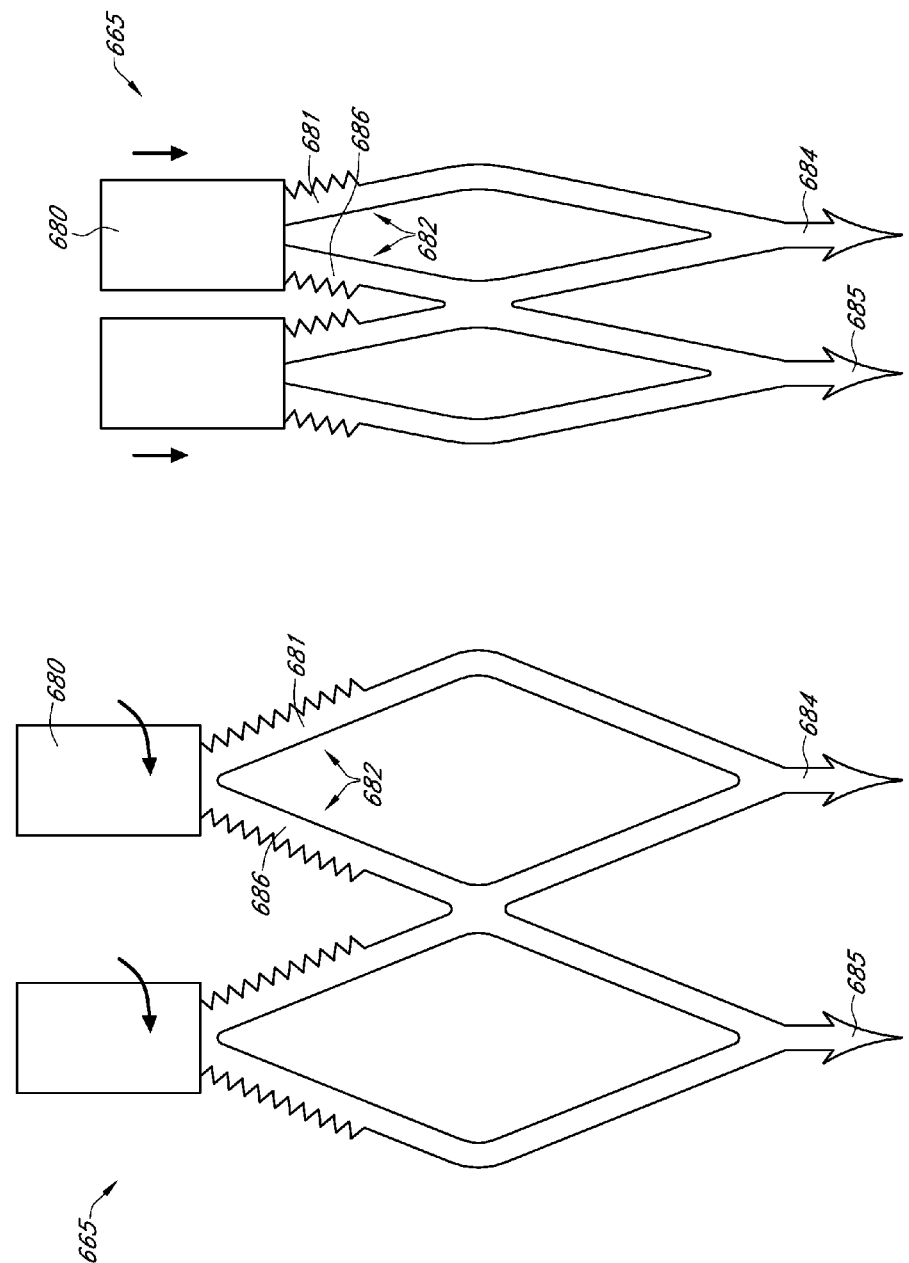

FIG. 6J illustrates an implant embodiment having diamond-shaped struts and sharp, pointed apices. In this embodiment, strut 682 has threaded arms 681 and 686 and anchor 684 at its bottom (base). Nut 680 may be used to position threaded arms 681 and 686 of strut 682, and consequently position anchor 684. For example, nut 680 may be rotatable about the threads of threaded arms 681 and 686, which may be configured such that the rotation of nut 680 moves nut 680 axially up or down strut 682. As nut 682 moves down strut 682, it may tighten strut 682 and/or bring threaded arms 681 and 686 closer together. As a result, anchor 684 moves closer to neighboring anchors, such as anchor 685. Implant 665 may have a plurality of struts and/or nuts. The nuts may be rotated independently or simultaneously in order to adjust the size of implant 665.

Figure 6K:
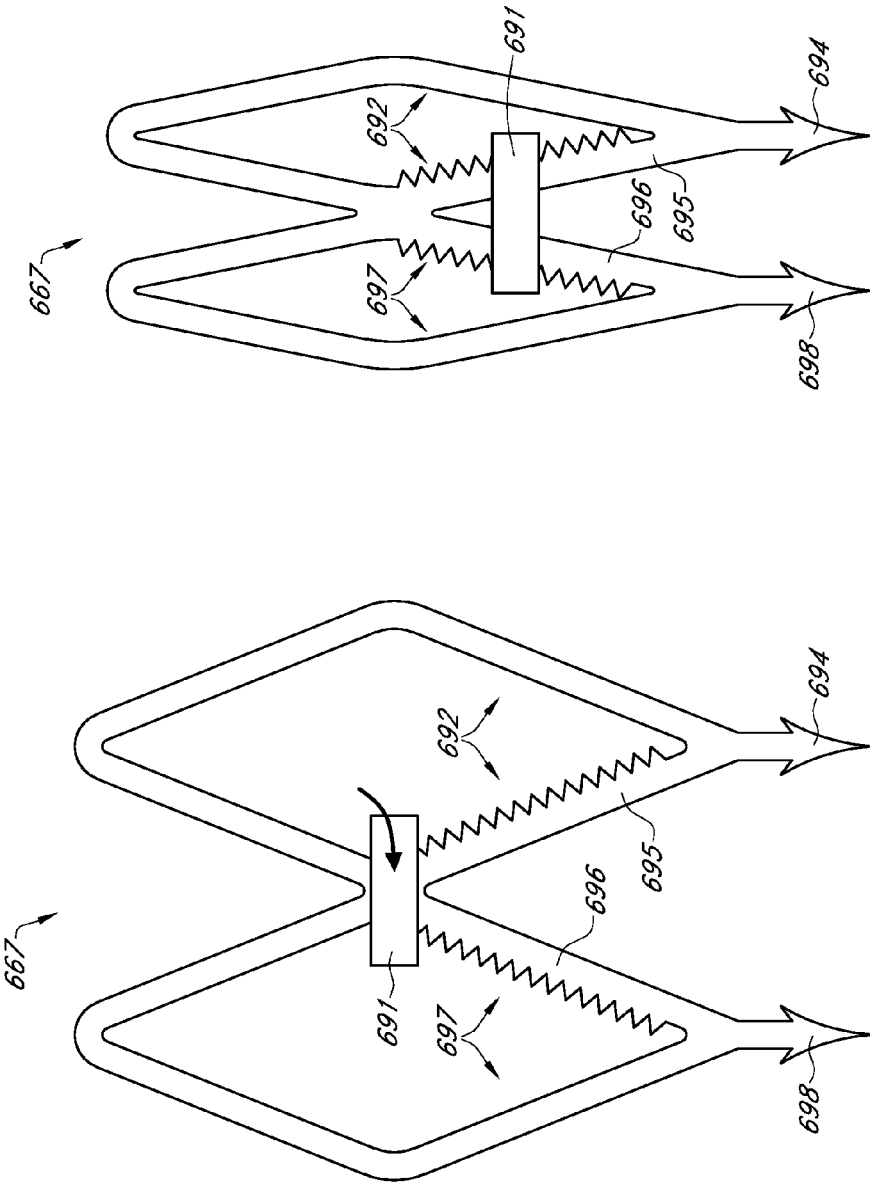

FIG. 6K illustrates a variation of FIG. 6J. In this embodiment, implant 667 has a plurality of diamond-shaped struts, which may be adjusted by clips that are on the lower parts of the struts. The clips may attach to the threaded arms of neighboring diamond-shaped struts. For example, strut 697 has threaded arm 696, and strut 692 has threaded arm 695. Threaded arms 695 and 696 are connected to anchors 694 and 698, respectively. When clip 691 is rotated, it may move up or down threaded arms 695 and 696. When clip 691 moves down towards anchors 694 and 698 along threaded arms 695 and 696, threaded arms 695 and 696 move closer together. Accordingly, anchors 694 and 698 move closer together.

It should be noted that implants may have uniform/symmetrical configurations or non-uniform/non-symmetrical configurations. For example, an implant may have sinusoidal struts all around. In other embodiments, an implant may have diamond-shaped struts all around. In still other embodiments, an implant may have both sinusoidal struts and diamond-shaped struts, such as in an alternating fashion. Each strut of an implant may use the same mechanism(s) (e.g., one or more of the mechanisms and/or adjustable restraints illustrated in FIG. 6A-L) to adjust anchor positions, or any strut may use different mechanism(s) than other struts. In some embodiments, struts could have different shape patterns, such as a flat or plateaued segment in between ascending and descending arms.

Figure 6L:
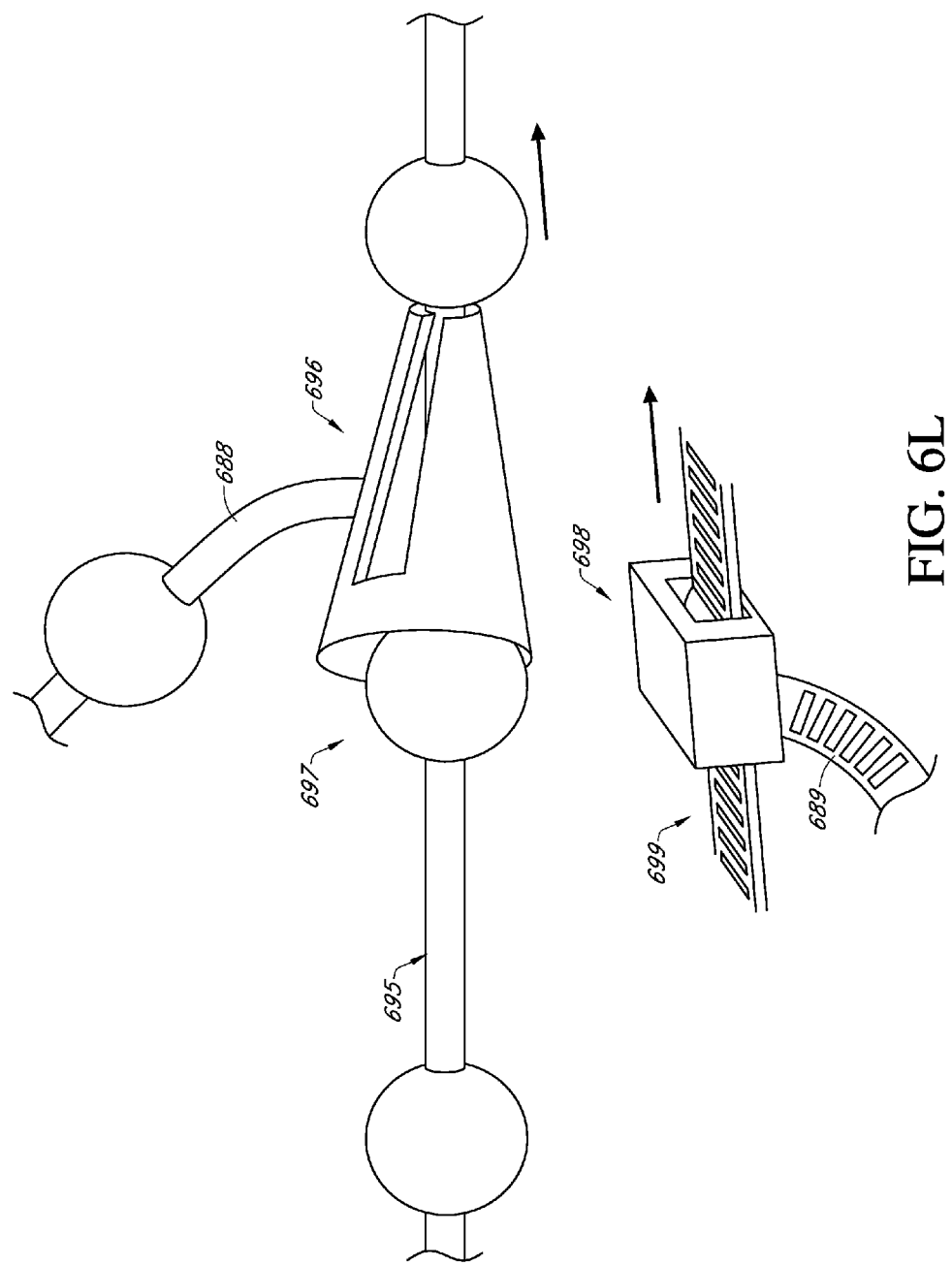

FIG. 6L illustrates various cable lock systems for cables such as cable 638 (FIG. 6E), cable 640 (FIG. 6F), cable 650 and 651 (FIG. 6G), and/or cables 661, 662, and 663 (FIG. 6H). The cable lock systems may be used to lock the cables to a certain length, change the length of the cables (e.g., loosen or tighten, and/or lengthen or shorten), and/or connect cables to each other or to an implant. For example, cable 695 may have a ball-and-cone clasping mechanism. By way of illustration, cable 695 might have end 688 that connects to clasp cone 696. The balls of cable 695 may uni-directionally pass through cone 696 by applying sufficient force. For example, ball 697 of cable 695 may be pulled through the larger end of clasp cone 696 through the smaller end by applying sufficient force. The amount of force required may be changed by the selection of clasp cone 696, which may offer more or less resistance to the passing of ball 697 as desired. As balls are pulled through clasp cone 696, the length of cable 695 shortens. The shape of clasp cone 697 prevents balls from being pulled through the smaller end of clasp cone 696 back through the larger end, thereby preventing cable 695 from being lengthened after it has been shortened. When cable 695 is used with an implant, cable 695 may be used to restrict the implant and hold the implant to a shape and/or size. The ball elements need not necessarily be spherical as shown, and can take the form of beads, cubical, rectangular, pyramidal, or other elements having at least one dimension greater than that of the cable.

Alternatively, a structure similar to a cable-tie may be used, such as a one-way ratchet or zip tie for example. For example, cable 699 may have a plurality of ridges. Clasp 698 may be attached to end 689 of cable 699. Clasp 698 may be configured to interact with the ridges of cable 699 such that cable 699 can pass through clasp 698 when cable 699 is pulled with sufficient force in a certain direction. This mechanism may utilize a directional clip inside clasp 698, where the clip slides into the ridges of cable 699. When ridges are pulled through clasp 698, cable 699 shortens. Because clasp 698 prevents cable 699 from being pulled in the opposite direction, clasp 698 prevents cable 699 from being lengthened. As a result, cable 699 may be used to restrict an implant.

Figure 7:
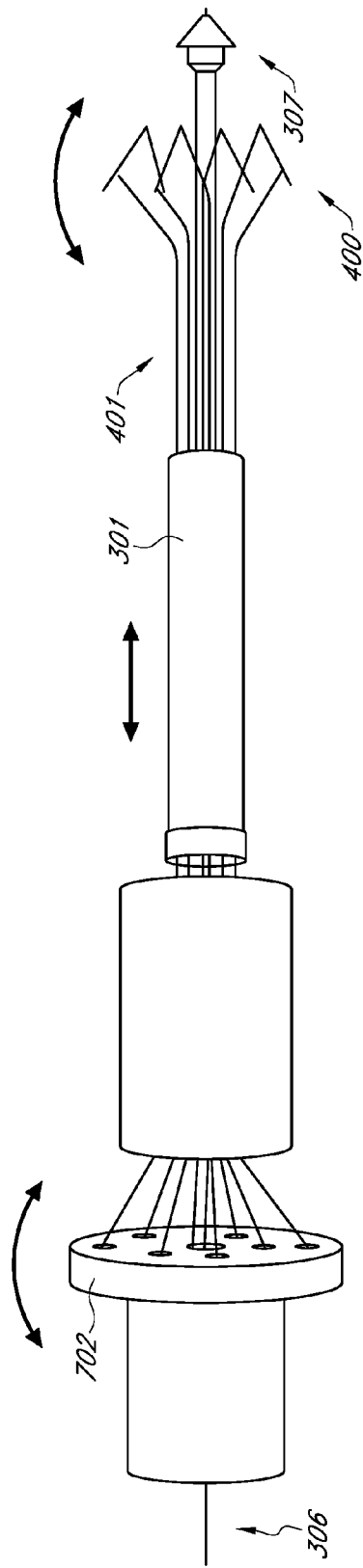
FIG. 7 illustrates an example tilt adjuster that may be used with the delivery catheter illustrated in FIG. 5A.

FIG. 7 illustrates an example tilt adjuster that may be used with the delivery catheter illustrated in FIG. 5A. Delivery catheter 301 may have tilt adjuster 702. Tilt adjuster 702 may connect to connector arms 401, which run through at least part of the length of delivery catheter 301 and connect to implant 400. The sheath of delivery catheter 301 has been withdrawn to expose connector arms 401 and implant 400. By actuating tilt adjuster 702, connector arms 401 may be moved in order to tilt implant 400 as desired. In some cases, the movement of tilt adjuster 702 pulls and pushes the various wires in connector arms 401, which in turn causes implant 400 to tilt and/or move out of plane. Such tilting may be desirable to navigate implant 400 into position in the heart. Typically, tilting can vary from minus 30 degrees to plus 30 degrees at any selected angle. Guidewire 306 may run through delivery catheter 301. In some cases, guidewire 306 may extend through tip 307, as also illustrated in FIG. 5A.

Figure 8:
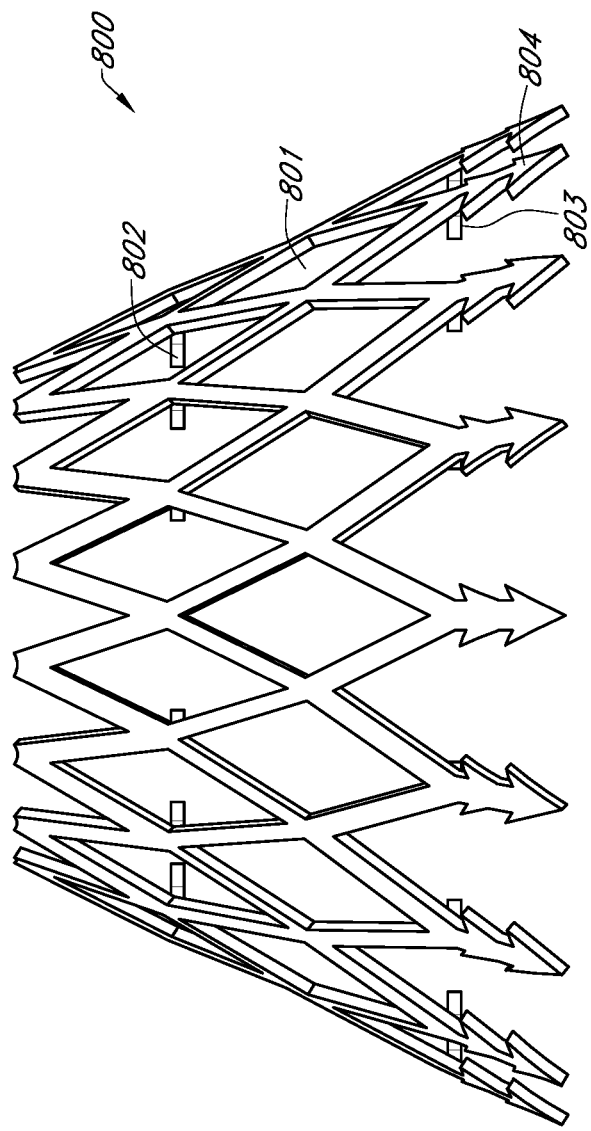
FIG. 8 illustrates an example tapered implant with a diamond pattern.

FIG. 8 illustrates an example tapered implant with a diamond pattern. Implant 800 has a plurality of diamond cuts, such as diamond cut 801. It also has a conical shape, where the top (distal to the anchors) is narrower than the bottom (proximal to the anchors). Implant 800 also has a plurality of receiver holes, such as receiver holes 802 and 803, located at numerous spaced axially and/or radially apart places. Receiver holes may be located anywhere as desired on implant 800. For example, a receiver hole may be located at a point on implant 800 in order to allow adjustment of sections of implant 800 adjacent to that point using cables and/or connection arms as previously described in this disclosure. By way of illustration, receiver hole 803 may be positioned near anchor 804 in order to allow a cable to connect to receiver hole 803 and adjust the position of anchor 804. Receiver hole 803 may interact with cables in order to adjust the size and/or shape of implant 800 in any way(s) described in this disclosure.

In some embodiments, implant 800 may be initially configured such that the upper-end is smaller or larger in diameter than the lower-end, as pictured in FIG. 8, such as about or at least about 5%, 10%, 15%, 20%, 25%, 30%, 40%, 50%, or more greater than the other respective end. The lower-end may have anchors that are positioned to allow for an angular implantation of the anchors into the tissue surrounding and/or including the mitral valve. Once the anchors have been fixed to the tissue, the tapered implant could switch orientation so that the lower-end becomes smaller in size and the upper-end becomes larger. Such switching could be initiated by the downward force of embedding the anchors into the tissue, where the struts of the implant are configured to flip orientation due to the downward force. In some cases, the implant may have an equilibrium shape where the upper-end is larger than the lower-end. The downward force of embedding the implant while it is not in its equilibrium shape (e.g., while the lower-end is larger than the upper-end) may cause the implant to flip back to its equilibrium shape, thereby causing the lower-end to contract—which would cause the tissue connected to the lower-end to contract as well.

In other embodiments, the orientation switching may also occur due to radial forces, supplied from the handle of the delivery catheter, applied to the upper-end and/or lower-end of implant 800. For example, connection arms connected to receiver holes of the upper-end of implant 800 may force the upper-end to expand. In some cases, a balloon may also be used to push the upper-end wider. In some cases, cables mechanisms, as in any cable mechanism described in this disclosure, may be used to pull the upper-end diameter larger and/or pull the lower-end diameter smaller. Tapered implants such as implant 800 may be diamond-patterned and/or sinusoidal.

Figure 9:
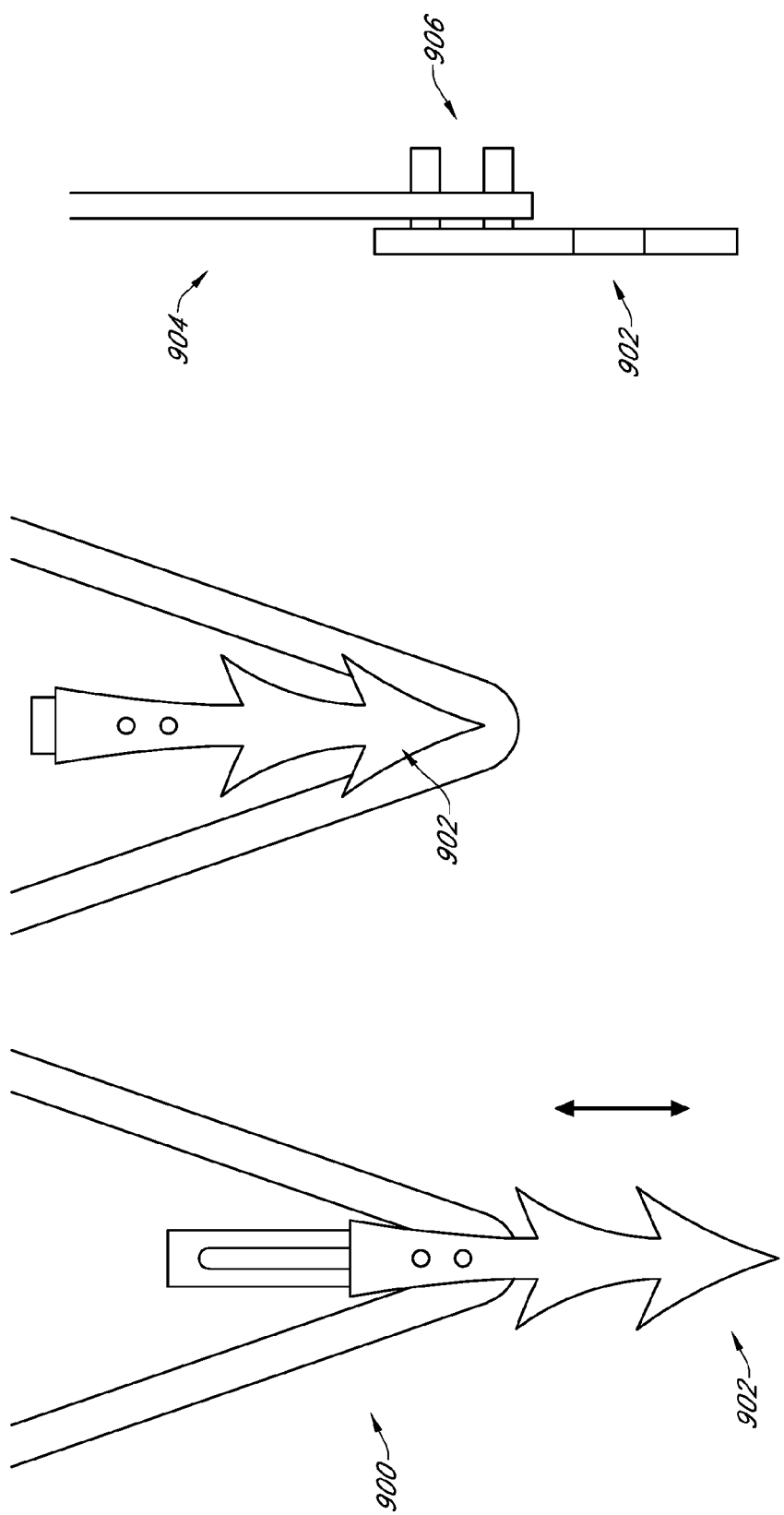
FIG. 9 illustrates an example retractable anchor mechanism that may be used in some implants.

FIG. 9 illustrates an example retractable anchor mechanism that may be used in some implants. Structure 900 may comprise retractable anchor 902, which may be exposed and/or manipulated to interact with heart tissue. In some embodiments, anchor 902 may be lowered (e.g., moved distally) to be exposed, such as along a track or guide rail. In the exposed state, it may be embedded into tissue surrounding and/or including a mitral valve. In contrast, when anchor 902 is retracted (e.g., raised up, e.g., proximally), anchor 902 may not be exposed. The retracted state may be desirable to prevent interaction between anchors and tissue as the implant is positioned in the heart, and before the implant is embedded into the tissue surrounding and/or including a mitral valve. States between retracted and exposed may be used to control the depth anchor 902 embeds in tissue. Anchor 902 may be positioned using slide 904, which may be coupled to spokes 906 of anchor 902. Slide 904 may use lockable rails and/or clips that interact with spokes 906 to lock anchor 902 in place.

Figure 10:
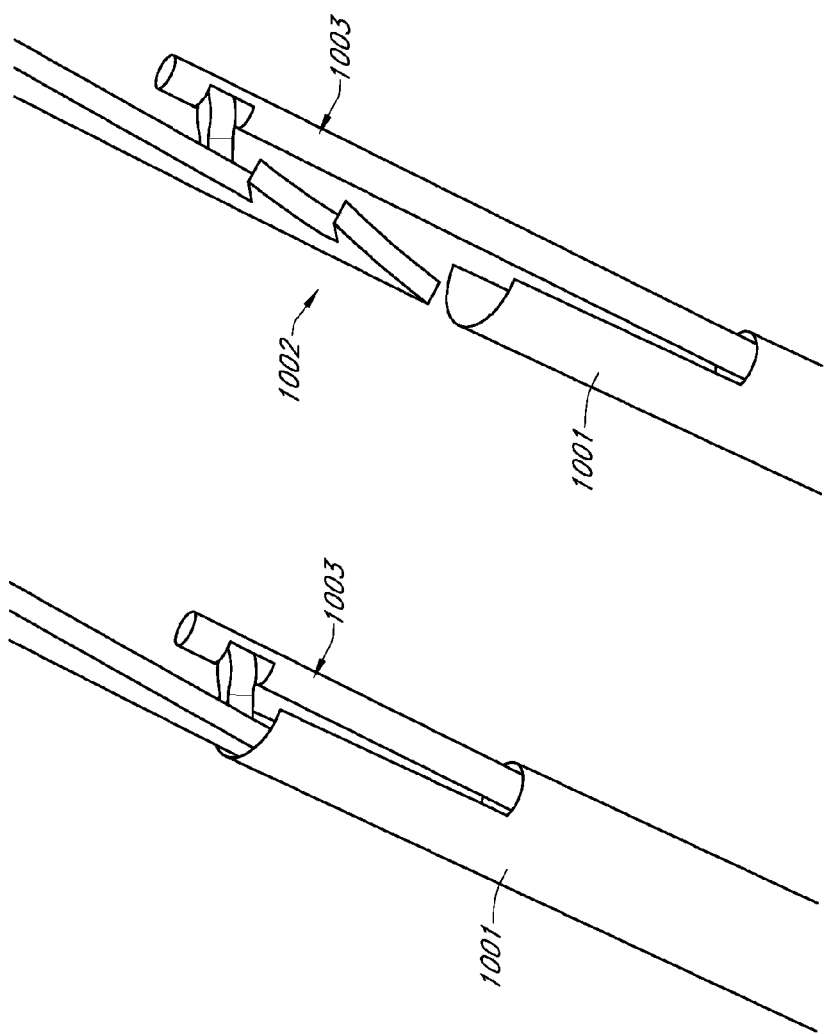
FIG. 10 illustrates an example anchor being removed from an anchor cover or sheath.

FIG. 10 illustrates an example anchor being removed from an anchor cover or sheath. For example, anchor 1002 may be covered by anchor cover 1001 to prevent interaction of anchor 1002 and tissue until anchor 1002 is exposed. Control rods, such as tubular member 1003, which may be structured like tubular member 624 (FIG. 6C) and/or part of a connection arm, may be connected to anchor 1002 and pull it from anchor cover 1001. In this way, anchor 1002 may be exposed in order to embed anchor 1002 into the tissue surrounding and/or including a mitral valve, and/or when desired.

In some embodiments, the actuation or exposure of anchor 1002 may be simultaneous with device expansion or secondarily initiated through the delivery catheter using a proximal control such as a push or pull member to advance anchor 1002 out of anchor cover 1001 using tubular member 1003. An alternative may be a rotational or screw mechanism to advance anchor 1002 distally out of anchor cover 1001.

Figure 11:
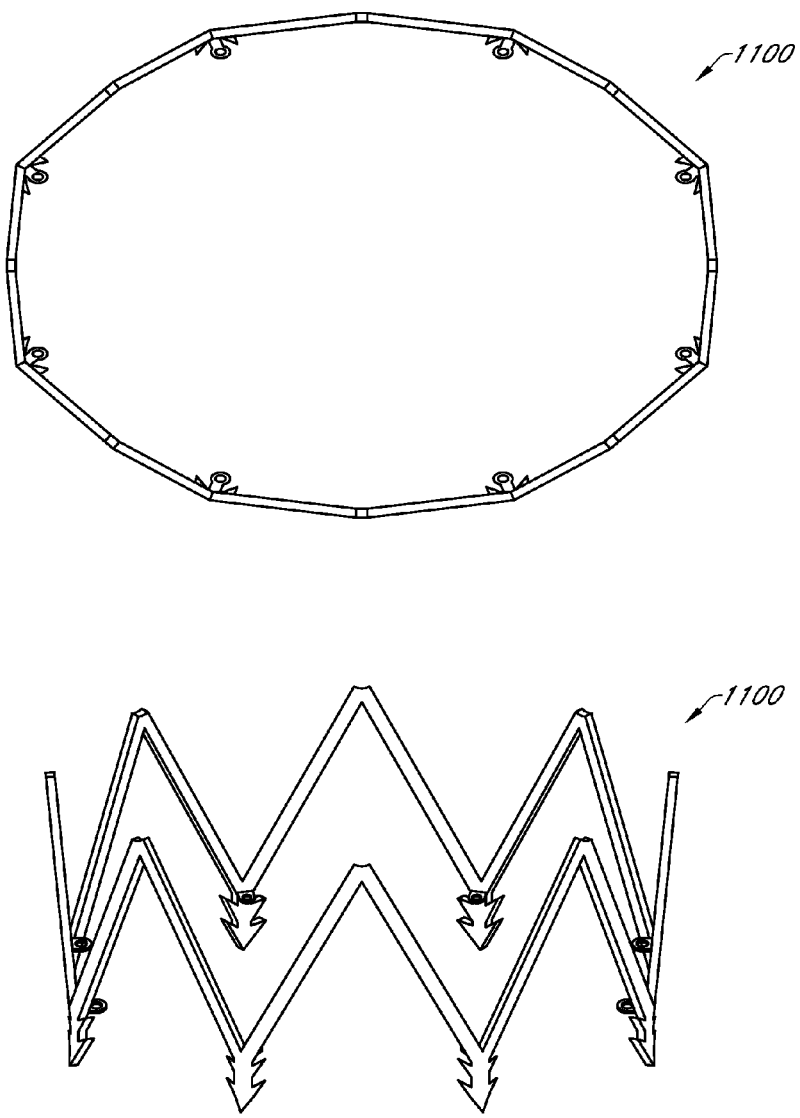
FIG. 11 illustrates the expanded shape of an example implant from a top and side view.

FIG. 11 illustrates the expanded shape of an example implant from a top and side view. Implant 1100 may be an oval or substantially shape where the long axis measures about 30 to 40 millimeters and the short axis measures about 15 to 25 millimeters. Such a shape may be desirable in some circumstances in order to better match a desired mitral valve shape of a patient. In some embodiments, implant 1100 may be adjusted using mechanisms described in this disclosure in order to better match the desired shape of the mitral valve of a patient.

Figure 12:
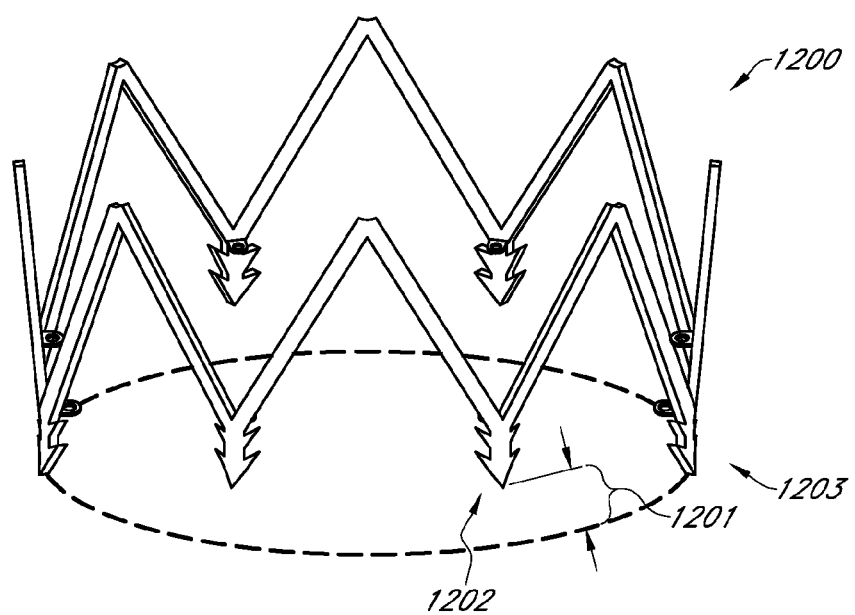
FIG. 12 illustrates an example implant where the amplitude is nonsymmetrical about the implant's diameter.

FIG. 12 illustrates an example implant where the amplitude is nonsymmetrical about the implant's diameter. Implant 1200 has a higher phase along the ends of its minor axis and a lower phase along the ends of its major axis. For example, anchor 1202 is positioned with an amplitude change 1201 higher than anchor 1203. The clinical benefit of having such amplitude variation in the implant is that it allows the implant to be rotated into position where the lower phase, or longer struts, would reach out farther to the commissures of a mitral valve. This may be desirable in some cases because the mitral valve (and/or annulus) can be non-planar and more saddle-shaped, and also varies patient-to-patient and/or with the progression of a disease state.

In some embodiments, implant 1200 could feature a three-dimensional saddle shape similar to a GEOFORM ring from Edwards Lifesciences (Irvine, Calif.), which may better match the mitral valve's three-dimensional anatomy in some cases. This three-dimensional saddle shape may reflect a mitral valve's reduced anterior-posterior distance and an elevated P2 segment. In some cases, the saddle shape has a top (distal to the anchors) linear segment, with a bottom (proximal to the anchors) bi-curved segment. In some embodiments, a plurality of anchors at opposing sides of the implant have a lower phase than the other anchors.

In some embodiments, the wall thickness of implant 1200 could measure about 0.010 to about 0.030 inches and could vary from top to bottom or on individual radial segments to change the stiffness of implant 1200 at locations about implant 1200. Prior to implantation, diameter grinding and/or lateral grinding of implant 1200 could be used to selectively remove material around implant 1200 as needed. The grinders could be set with rotary fixtures to adjust implant 1200 accordingly for selective removal of material.

Adjusting the size and/or shape of an implant described in this disclosure may require mechanical drivers and/or actuators to adjust the position of adjustable restraints (e.g., screws, nuts, and/or cables) and/or other structures of the implant (see, e.g., FIGS. 6A-L). Such mechanical drivers and/or actuators may include a variety of mechanisms that may rotate, slide, push, pull, and/or actuate structures of the implant. In some embodiments, rotational drivers may be connected to the implant through the handle of the delivery catheter.

Figure 13:
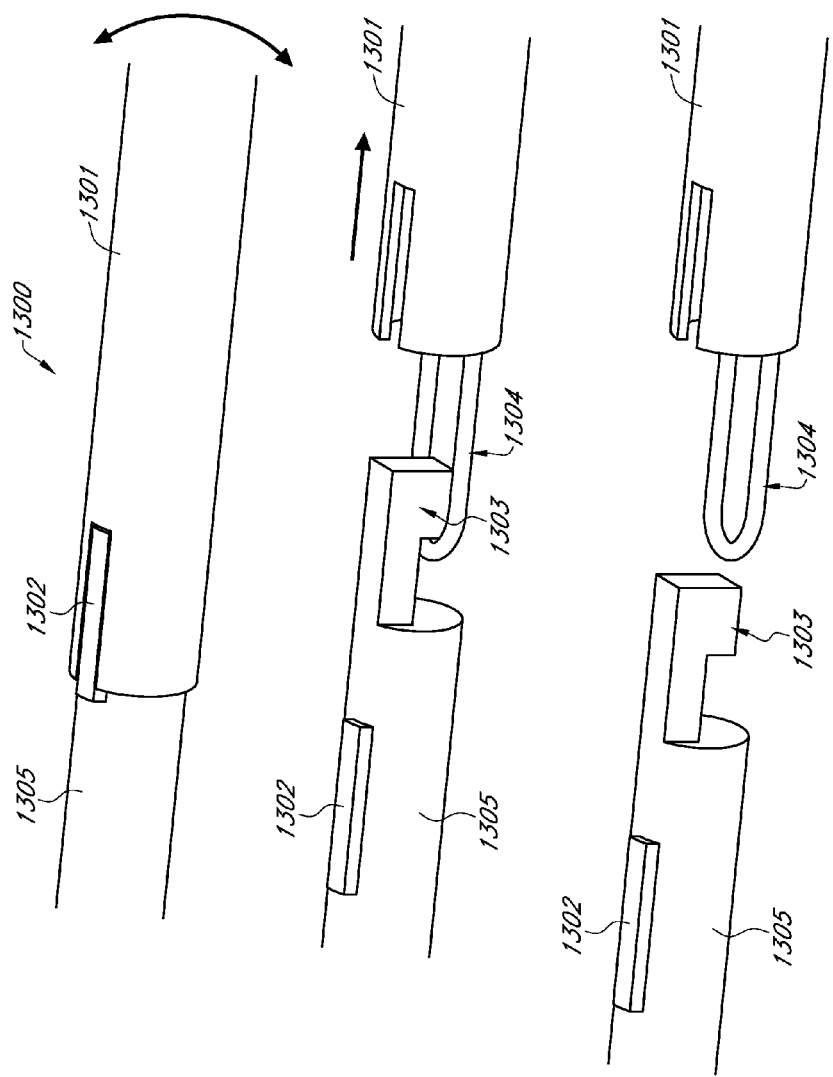
FIG. 13 illustrates an example hook-and-wire rotational driver that can be used to manipulate an implant.

FIG. 13 illustrates an example of a hook-and-wire rotational driver that can be used to manipulate an implant. Member 1300 may connect to a screw, nut, and/or other rotatable structure of an implant (see, e.g., FIGS. 6A-L). Member 1300 may comprise tubular cover 1301 and loop 1304. Rotational driver 1305 may comprise hook 1303 and stopper 1302. Rotational driver 1305 may be connected to an external handle of the delivery catheter used to position the implant, where force is supplied to rotational driver 1305 at the handle. Rotational force may be applied through rotational driver 1305 to rotate member 1300.

During delivery of the implant, rotational driver 1305 may be connected to member 1300. In the connected position, hook 1303 is positioned in loop 1304. Rotational driver 1305 and member 1300 may be pushed together such that hook 1303 and loop 1304 are positioned inside tubular cover 1301. Stopper 1302 may be positioned in a ridge in tubular cover 1301 to further stabilize the connection between rotational driver 1305 and member 1300, and to facilitate the transfer of rotational force from rotational driver 1305 to member 1300. This transfer of rotational force may turn a nut (e.g., nut 602 of FIG. 6A), a screw (e.g., screw 630 of FIG. 6D), a spool/ream (e.g., to control the length of cable 640 of FIG. 6F), rotate the implant, and/or rotate any part/component of the implant. After the implant is positioned and/or sized/shaped as desired, rotational driver 1305 and member 1300 may be disengaged by pulling them apart and unhooking hook 1303 from loop 1304. Rotational driver 1305 and member 1300 may also be re-engaged by placing hook 1303 in loop 1304, and pushing rotational driver 1305 into tubular cover 1301.

Figure 14:
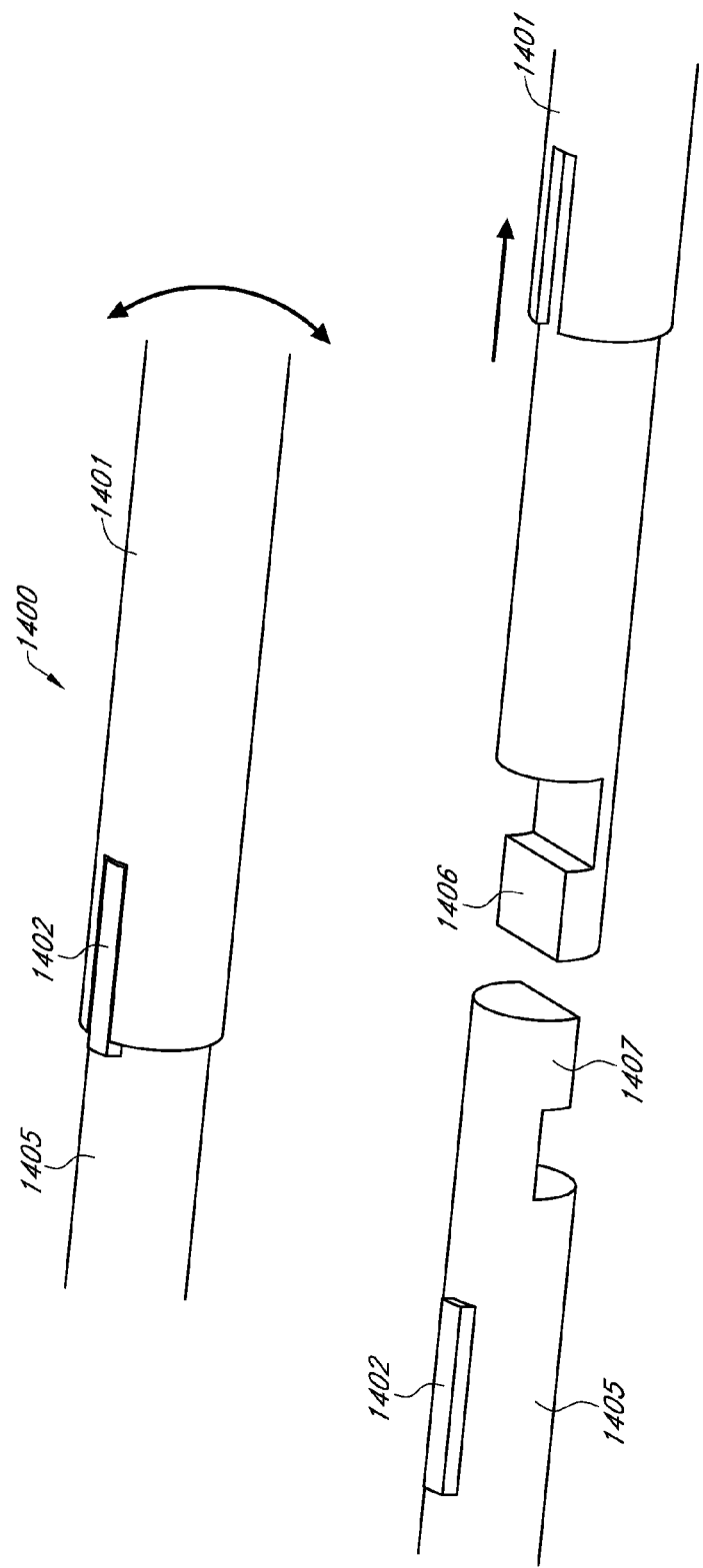
FIG. 14 illustrates an example two-arm rotational driver that is similar to the rotational driver of FIG. 13.

FIG. 14 illustrates an example two-arm rotational driver that is similar to the rotational driver of FIG. 13. Member 1400 may be fitted with hook 1406. Rotational driver 1405 may be fitted with hook 1407 that is configured to connect with hook 1406.

During delivery of the implant, rotational driver 1405 may be connected to member 1400. In the connected position, hook 1407 is clasped to hook 1406. Rotational driver 1405 and member 1400 may be pushed together such that hook 1407 and 1406 are positioned inside tubular cover 1401. Stopper 1402 may be positioned in a ridge in tubular cover 1401 to further stabilize the connection between rotational driver 1405 and member 1400, and facilitate the transfer of rotational force from rotational driver 1405 to member 1400. This transfer of rotational force may turn a nut (e.g., nut 602 of FIG. 6A), a screw (e.g., screw 630 of FIG. 6D), a spool/ream (e.g., to control the length of cable 640 of FIG. 6F), rotate the implant, and/or rotate any part/component of the implant. After the implant is positioned and/or sized/shaped as desired, rotational driver 1405 and member 1400 may be disengaged by pulling them apart and unhooking hooks 1407 and 1406 from each other. Rotational driver 1405 and member 1400 may also be re-engaged by clasping hooks 1407 and 1406 together, and pushing rotational driver 1405 into tubular cover 1401.

Figure 15:
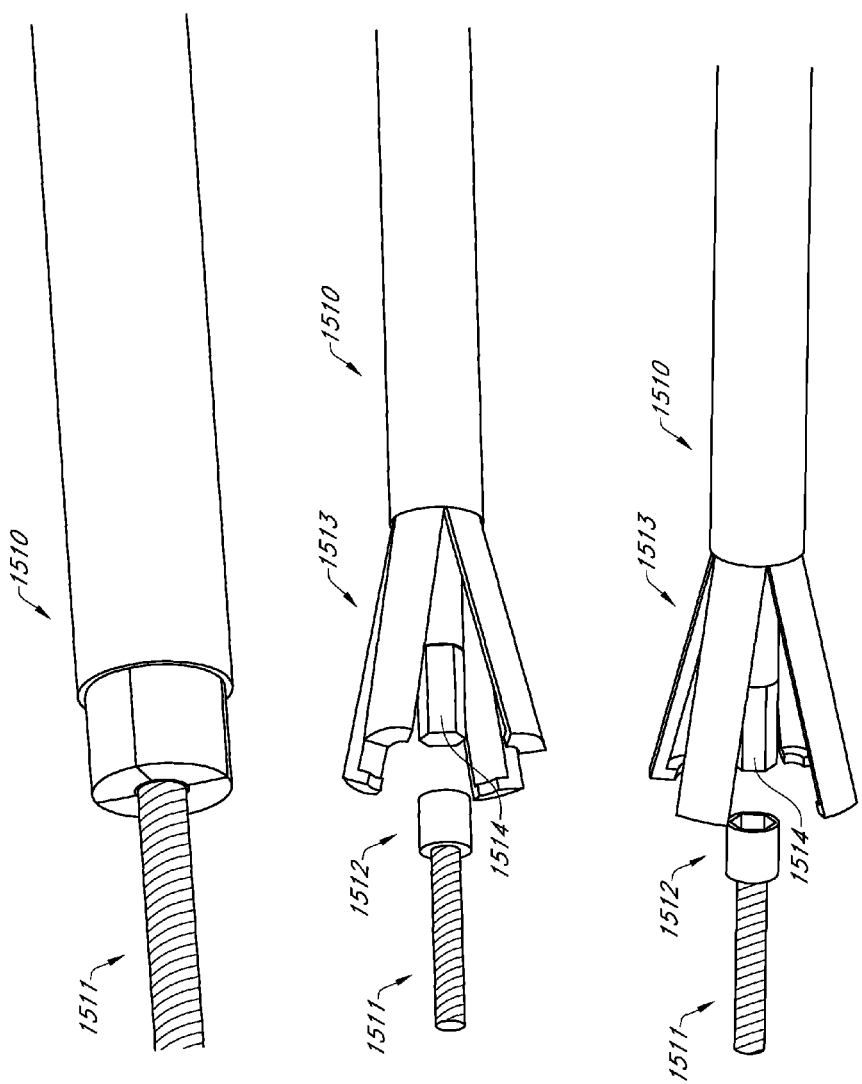
FIG. 15 illustrates an example hex rotational driver that can be used to manipulate an implant.

FIG. 15 illustrates an example hex rotational driver that can be used to manipulate an implant. Rotational driver 1510 has clasp 1513 and screwdriver head 1514. During delivery, screwdriver head 1514 and screw head 1512 may be engaged with clasp 1513 closed around them. While engaged, rotational force may be transferred from rotational driver 1510 to screw 1511. The rotational force may be supplied to screw 1511 by rotating screw driver head 1514 and/or rotating rotational driver 1510. The rotation of screw driver head 1514 and/or rotational driver 1510 may be controlled and/or supplied from the external handle of the delivery catheter.

Screw 1511 may be, for example, any screw described in this disclosure (e.g., screw 630 of FIG. 6D). Screw 1511 may also be coupled to any rotatable part/component of an implant in order to transfer rotational force. For example, screw 1511 may be coupled to adjustable restrains, such as a nut (e.g., nut 602 of FIG. 6A), a spool/ream (e.g., to control the length of cable 640 of FIG. 6F), an implant (e.g., to rotate the implant), and/or rotate any part/component of the implant.

In some embodiments, rotational driver 1510 and screw 1511 may be disengaged by opening clasp 1513 and pulling rotational driver 1510 away from screw 1511. The arms of clasp 1513 may be opened by a desired control such as a switch (e.g., a switch on the handle of the delivery catheter), pulley system, clasp system, and/or any other method known in the art for mechanically driving the opening of the arms of a clasp. Rotational driver 1510 and screw 1511 may be re-engaged by opening clasp 1513 and pushing rotational driver 1510 into screw 1511 again.

FIGS. 16A-B illustrate a side-view and top-view of a rotational driver that can be used to rotate a nut over a strut in an appropriate direction. FIG. 16A illustrates a side-view of rotational driver 1608 engaged and disengaged from strut 1605. FIG. 16B illustrates a top-view of rotational driver 1608 disengaged from strut 1605. Strut 1605 has threads cut along it. Strut 1605 may be, for example, any of the struts described in this disclosure (see, e.g., FIGS. 6A-L). The threads are configured such that the rotation of nut 1601 moves nut 1601 along (e.g., axially) strut 1605. Rotational driver 1608 comprises cog 1607 that is configured to engage nut 1601. Small bent wire 1602 or a similar mechanism may be used as a counter force to keep nut 1601 and rotational driver 1608 engaged by hooking into space 1609 of strut 1605.

During delivery, small bent wire 1602 is hooked into space 1609 and nut 1601 and rotational driver 1608 are engaged. Rotational driver 1608 and nut 1601 are pushed together so that they are locked together, and space 1609 and cog 1607 are positioned in tubular cover 1610. In this state, rotational force may be applied through rotational driver 1608 to rotate nut 1601, thereby moving it along (e.g., axially) strut 1605. The rotation of rotational driver 1608 may be controlled and/or supplied from the external handle of the delivery catheter. Nut 1601 and cog 1607 may be disengaged by pulling them apart and disconnecting small bent wire 1602 from space 1609. Rotational driver 1608 and strut 1605 may also be re-engaged by hooking small bent wire 1602 and space 1609 together, and pushing rotational driver 1608 and strut 1605 together.

Figure 17A:
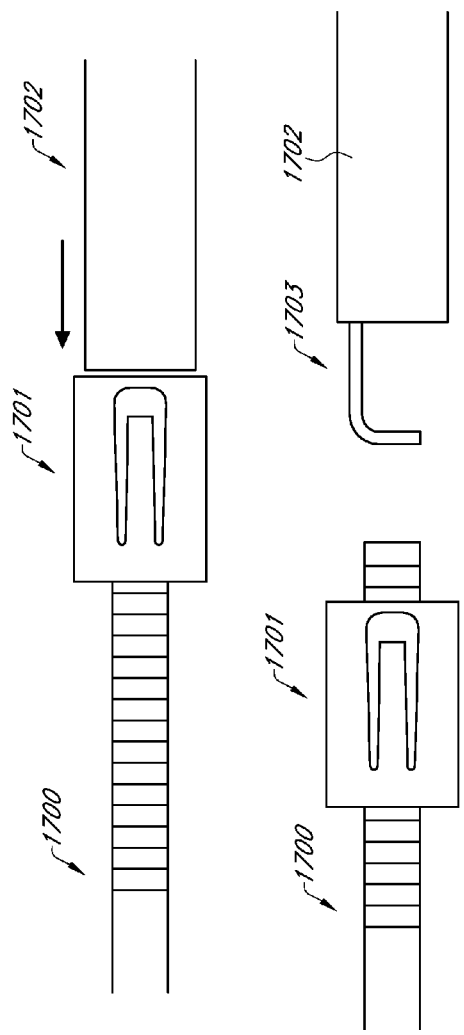
FIGS. 17A-B illustrate an example push-slider mechanism that may be used to manipulate an implant.
Figure 17B:
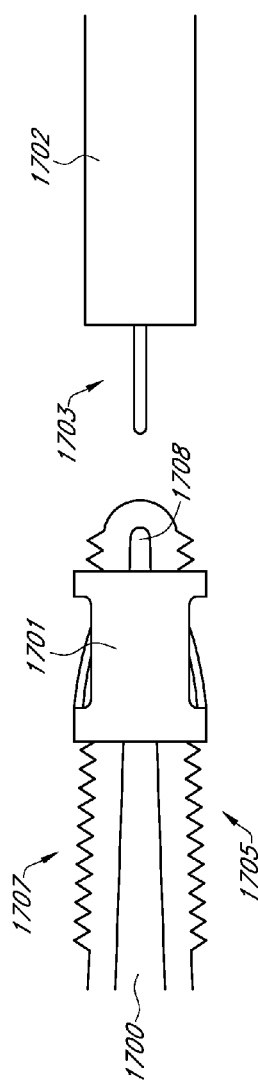

FIGS. 17A-B illustrate an example push-slider mechanism that may be used to manipulate an implant. FIG. 17A illustrates a side-view of push tube 1702 engaged and disengaged from strut 1700 respectively. FIG. 17B illustrates a top-view of push tube 1702 disengaged from strut 1700.

Push tube 1702 may be used to push clip 1701 or other adjustable restraints down strut 1700. The movement (e.g., axial movement) of push clip 1701 may draw the arms 1705 and 1707 of strut 1700 closer to one another, which in turn may pull the anchors attached to arms 1705 and 1707 of strut 1700 together. Where the anchors are attached to the tissue surrounding and/or including a mitral valve, the tissue is similarly pulled together. Push clip 1701 may have an outer diameter and an inner diameter with a single or a plurality of fingers protruding inward creating a cog that interacts with the ridges of arms 1705 and 1707 to limit motion in one direction. The shape of push clip 1701 may be non-circular and/or an oval to better conform to the shape of strut 1700. Push clip 1701 may be constructed from stainless steel, Nickel-Titanium, Cobalt-Chromium, Pyrolytic Carbon, Nitinol, polymer materials (e.g., PEEK), and/or other suitable implant materials. A counter force may be supplied from wire 1703, which hooks into space 1708 of strut 1700 and holds push tube 1702 to strut 1700, thereby connecting them. During delivery, wire 1703 may be placed in space 1708, and push tube 1702 and clip 1701 may be pushed together. Push tube 1702 and clip 1701 may be disengaged by unhooking wire 1703 from space 1708 and pulling push tube 1702 away from clip 1701 and strut 1700. They may be re-engaged by hooking wire 1703 into space 1708 and pushing push tube 1702 into clip 1701.

Figure 18A:
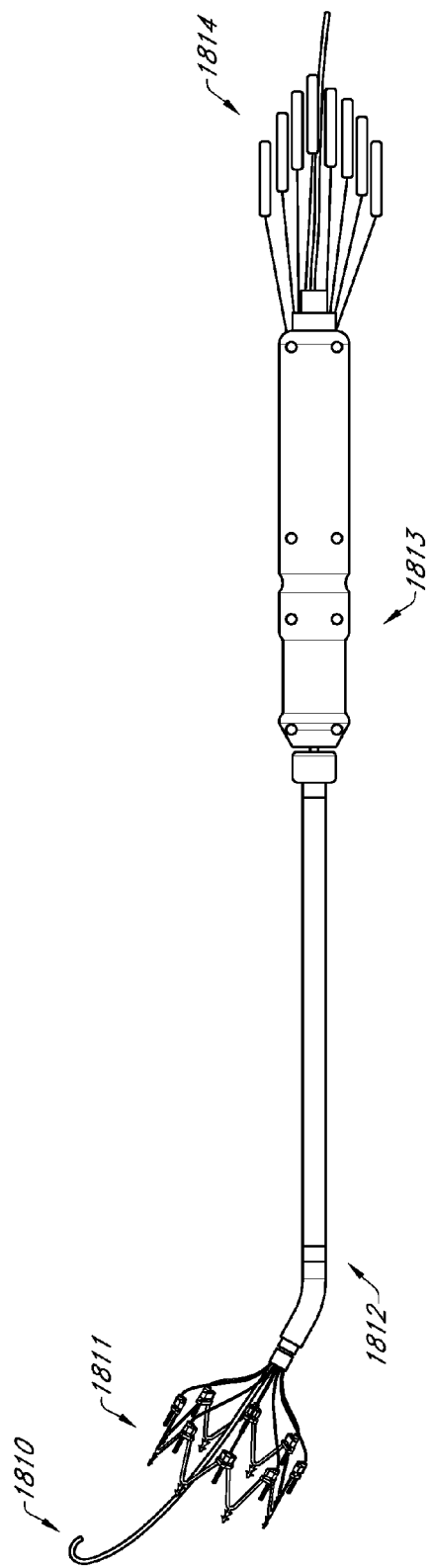
FIG. 18A illustrates an example delivery system for an implant having forward (distal) facing anchors for entry from the left atrium, or for entry from a femoral vein and a transseptal puncture.

FIG. 18A illustrates an example delivery system for an implant having forward (distal) facing anchors for entry from the left atrium, or for entry from a femoral vein and a transseptal puncture. The force for engaging implant 1811 into the heart tissue would be, in some cases, a forward or pushing mechanism to engage the anchors of implant 1811. Included in the delivery system is guidewire 1810. Sheath 1812 may cover implant 1811 before it is expanded for delivery and positioning. The distal end of sheath 1812 may include a pre-shaped curve to match the anatomical needs of the patient. The distal end may also have an active ability to steer, curve, and/or rotate for delivery and/or positioning. Handle 1813 may allow for accurate positioning of implant 1811 and transmission of forces to implant 1811. Additionally, handle 1813 may allow for adjustments of implant 1811 through driver mechanisms, including any driver mechanism described in this disclosure. For example, in some embodiments, handle 1813 may have rotational drivers 1814, which may be any rotational driver described in this disclosure. Implant 1811 may also be, for example, any implant described in this disclosure, including ones that have sinusoidal, diamond-patterned, and/or tapered struts.

Figure 18B:
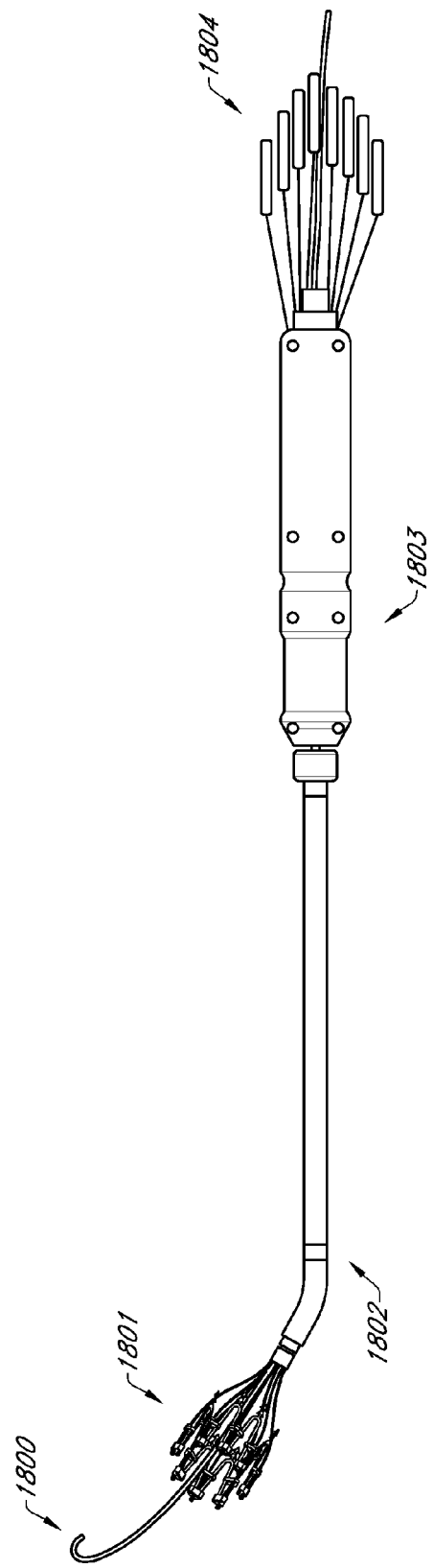
FIG. 18B illustrates an example delivery system for an implant having proximal facing anchors for entry from a left ventricle (e.g., a transapical entry).

FIG. 18B illustrates an example delivery system for an implant having proximal facing anchors for entry from a left ventricle (e.g., a transapical entry). Implant 1801 may pass through a left ventricle into the left atrium, and be exposed by a removal of sheath 1802 at the distal end. The removal of sheath 1802 may allow implant 1801 to expand or to be forcefully expanded by connection arms or other expansion mechanisms such as a balloon and/or any mechanism described in this disclosure for example. For example, implant 1801 may be connected to connection arms that shape implant 1801 to a diameter and/or shape to match the patient's mitral valve anatomy. As another example, a plurality of nuts (e.g., nut 602 (FIG. 6A), nut 680 (FIG. 6J), nut 691 (FIG. 6K)), clips (e.g., clip 634 (FIG. 6D) and clip 671 (FIG. 6I)), rings (e.g., locking ring 672 (FIG. 6I)), and/or cables (e.g., cable 640 (FIG. 6F)) may be positioned as to compress the size and/or shape of implant 1801, or any implant of this disclosure, while it is being delivered. The nuts, clips, and/or cables may be repositioned after implant 1801 has been delivered in order to expand implant 1801.

Handle 1803 may allow for adjustments of implant 1801 through driver mechanisms, including any driver mechanism described in this disclosure. Because of the proximal facing anchors of implant 1801, a screw-and-clip mechanism, similar to the mechanisms illustrated in FIG. 6D and/or FIG. 6I, may be suited to gather the struts of implant 1801 together. The screw-and-clip mechanism may be actuated by rotational drivers 1804 located at the proximal end of handle 1803. Rotational drivers 1804 may also implement any of the other actuating mechanisms described in this disclosure.

Figure 19:
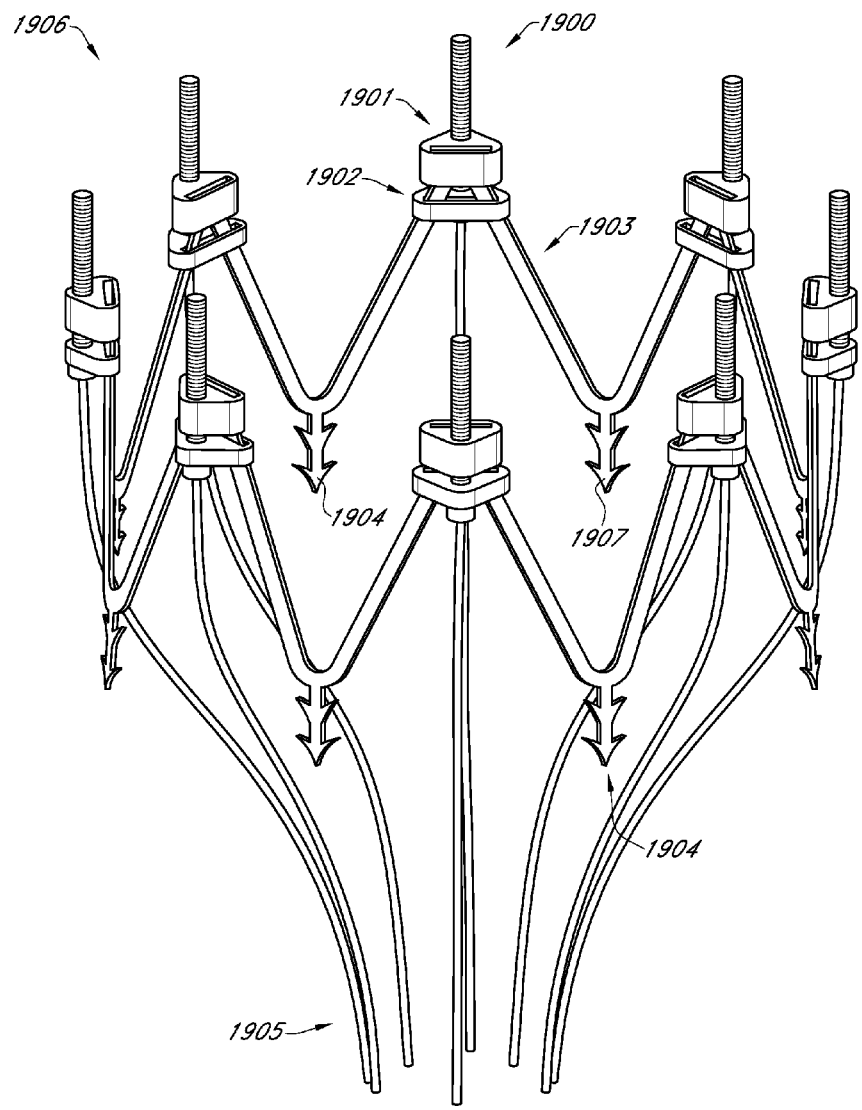
FIG. 19 illustrates a close-up of an example implant with proximal facing anchors with screw-and-clip mechanisms to adjust the shape and/or size of the implant.

FIG. 19 illustrates a close-up of an example implant with proximal facing anchors with screw-and-clip mechanisms to adjust the shape and/or size of the implant. For example, implant 1906 has strut 1903 that is connected to anchors 1904 and 1907. Strut 1903 has clip 1902, which is configured to gather the arms of strut 1903 closer together as clip 1902 advances along strut 1903. As the arms of strut 1903 gather together, so do anchors 1904 and 1907, and any tissue to which anchors 1904 and 1907 may be embedded. Attached to strut 1903 is threaded boss 1901 (which may be a screw retainer) to drive screw 1900 and clip 1902 up and down strut 1903. For example, loosening screw 1900 relative to boss 1901 moves clip 1902 downward, pulling the arms of strut 1903 together. Other struts of implant 1906 may have similar configurations and may be adjusted in coordination or independently.

Figure 20:
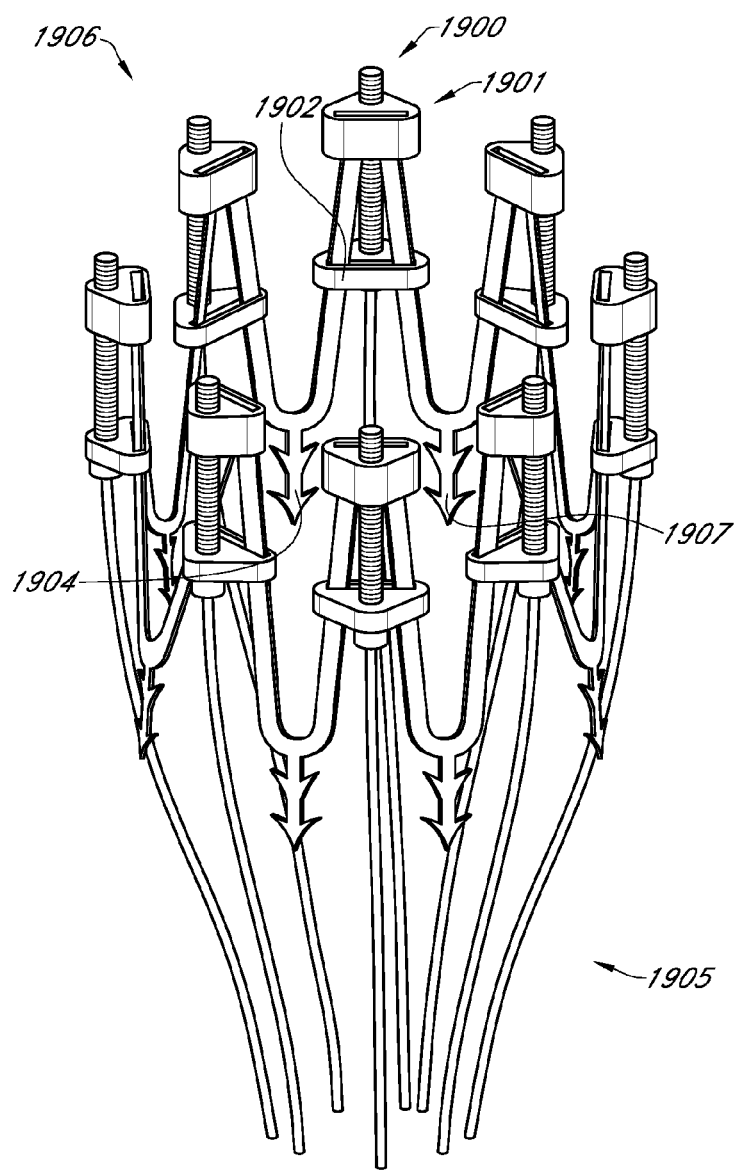
FIG. 20 illustrates a close-up of the implant of FIG. 19 where the screw-and clip mechanisms reduce the diameter of the implant.

FIG. 20 illustrates a close-up of the implant of FIG. 19 where the screw-and-clip mechanisms reduce the diameter of the implant. The actuation of the clips (e.g., clip 1902) may occur after anchors (e.g., anchors 1904 and 1907) are engaged into the tissue surrounding and/or including a mitral valve. The clips may also be in a downward position while implant 1906 is being delivered to a left atrium. The actuation of the clips may be driven by rotational drivers 1905, which may be controlled outside the body at the proximal end of the delivery system (see, e.g., rotational drivers 1814 (FIG. 18A) and rotational drivers 1804 (FIG. 18B)). Rotational drivers 1905 may connect to the screws (e.g., screw 1900) of implant 1906. In some embodiments, rotational drivers 1905 may also serve as connection arms that connect implant 1906 to a delivery catheter. The adjustment of the rotational drivers 1905 could also be reversed if the regurgitant flow of the mitral valve was altered negatively or added to the regurgitant flow volume.

Figure 21:
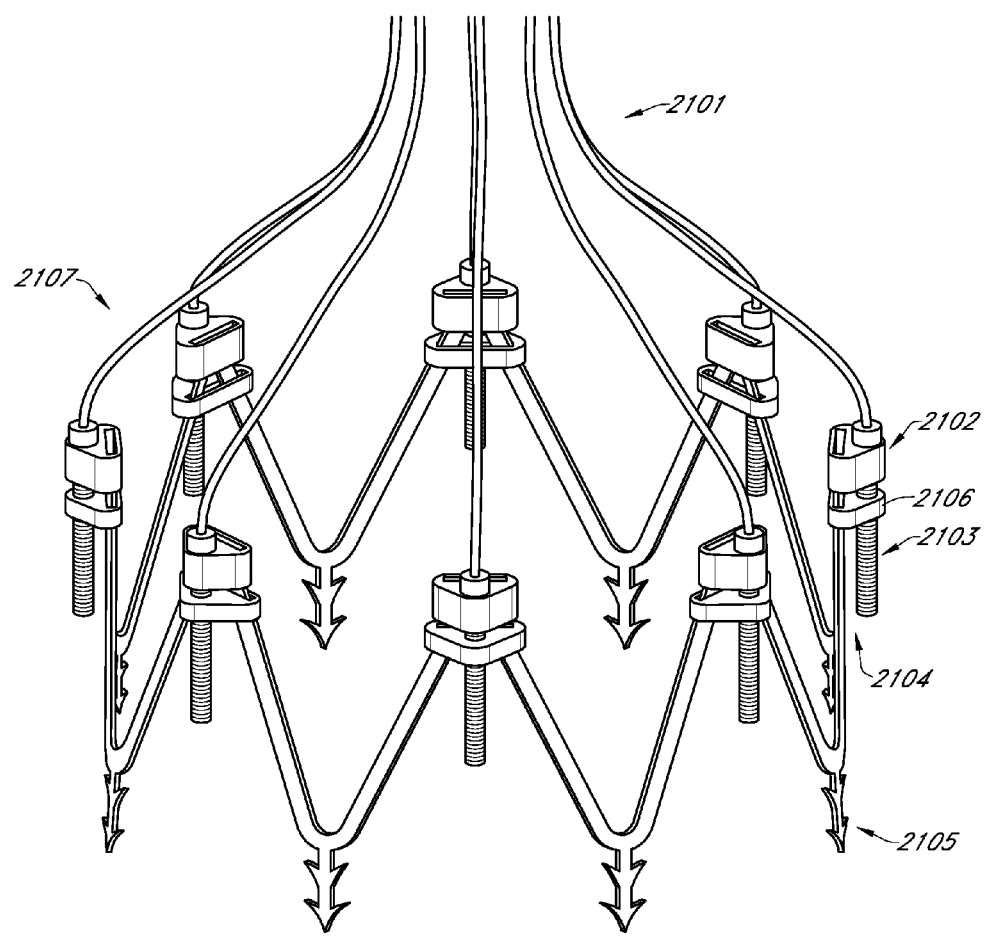
FIG. 21 illustrates a close-up of an example implant with distal facing anchors and screw-and-clip mechanisms to adjust the shape and/or size of the implant.

FIG. 21 illustrates a close-up of an example implant with distal facing anchors and screw-and-clip mechanisms to adjust the shape and/or size of the implant. Implant 2107 has a plurality of distal facing anchors, such as anchors 2105. The size and/or shape of implant 2107 may be adjusted in a similar way as implant 1906 illustrated in FIGS. 19 and 20 and use a screw-and-clip mechanism similar to those depicted in FIG. 6D and FIG. 6I. For example, rotational drivers 2101 connect to and deliver rotational force to the screws of implant 2107, including screw 2103. In this way, clip 2106 may be moved along strut 2104 by a rotational force from rotational drivers 2101. The rotational force may be translated to screw 2103 through boss 2102 (which may be a screw retainer). Similar to the implant illustrated in FIG. 20, the actuation may be controlled outside the body at the proximal end of the delivery system (see, e.g., rotational drivers 1814 (FIG. 18A) and rotational drivers 1804 (FIG. 18B)). The movement of the clips may be used to increase or decrease the size of implant 2107. In some embodiments, rotational drivers 2101 may also serve as connection arms that connect implant 2107 to a delivery catheter.

Figure 22A:
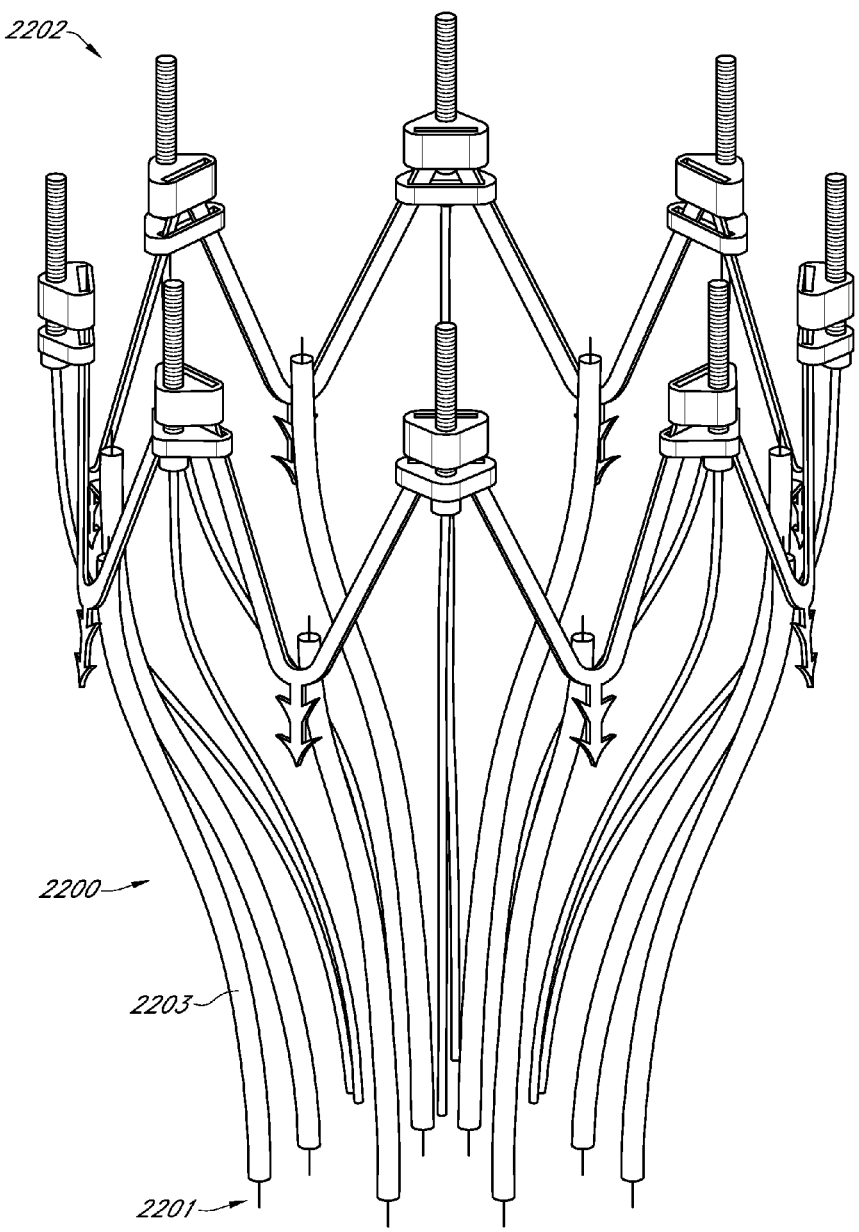
FIG. 22A illustrates a close-up of an example implant with proximal facing anchors and connection arms connected to the implant.

FIG. 22A illustrates a close-up of an example implant with proximal facing anchors and connection arms connected to the implant. Implant 2202 has similar screw-and-clip mechanisms as FIG. 19. Additionally, connection arms 2200 are connected to implant 2202 to allow for device expansion during delivery. Connection arms 2200 can be pre-shaped to make implant 2202 into a circular, oval, and/or elliptical shape to match the patient's mitral valve anatomy. Connection arms 2200 are designed to connect a handle and delivery system to implant 2202 for precise implant placement.

Connection arms 2200 may connect to implant 2202 by rotational screws that engage implant 2202. Connection arms 2200 may also connect to implant 2202 by tubular elements with wires passing through them. For example, tubular element 2203 has connection wire 2201 passing through it. Wire 2201 may then additionally pass through a receiver hole in implant 2202 to secure tubular element 2203 and the receiver hole together (see, e.g., FIG. 6C).

Once wire 2201 is retracted, tubular element 2203 becomes free to disengage from implant 2202. Similarly, some or all of the tubular members of connection arms 2200 may be disengaged from implant 2202. Tubular element 2203 can be constructed from materials including stainless steel, Nickel-Titanium, Cobalt-Chromium, Pyrolytic Carbon, Nitinol, polymer materials (e.g., PEEK), and/or other suitable implant materials. In some cases, where connection arms 2200 are pre-shaped, they provide a passive force expanding implant 2202 outward and controlling the shape of implant 2202.

Figure 22B:
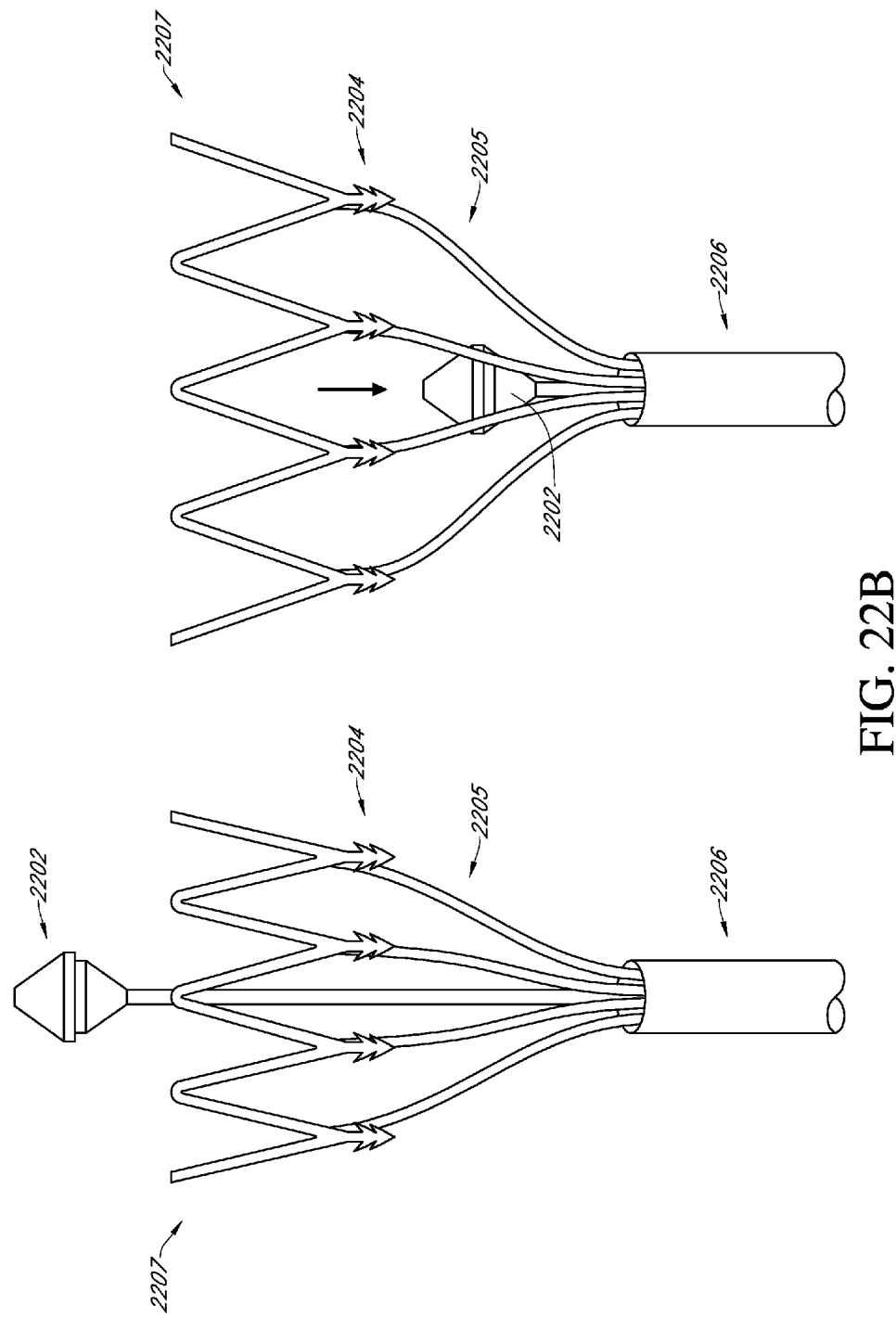
FIG. 22B illustrates an example implant with proximal facing anchors and connection arms attaching the implant to a delivery system.

FIG. 22B illustrates an example implant with proximal facing anchors and connection arms attaching the implant to a delivery system. Tip 2202 of delivery system 2206 is shown in the left image in a distal position. If pulled proximally (as in the right figure), tip 2202 may push connection arms 2205 apart from each other as tip 2202 is disposed between connection arms 2205. This action may expand implant 2207 to a larger diameter and/or shape for embedding into the tissue surrounding and/or including a mitral valve. Additionally, it should be appreciated that the expanded shape of implant 2207 may reflect the shape of tip 2202. Accordingly, tip 2202 may have a round, oval, elliptical and/or amorphous shape in order to shape connection arms 2205 and implant 2207 to better reflect the desired shape of the mitral valve when tip 2202 is pulled proximally. The disengagement of connection arms 2205 and tip 2202 from implant 2207 may allow implant 2207 to reduce in diameter through passive or active forces, as described in this disclosure.

Figure 23:
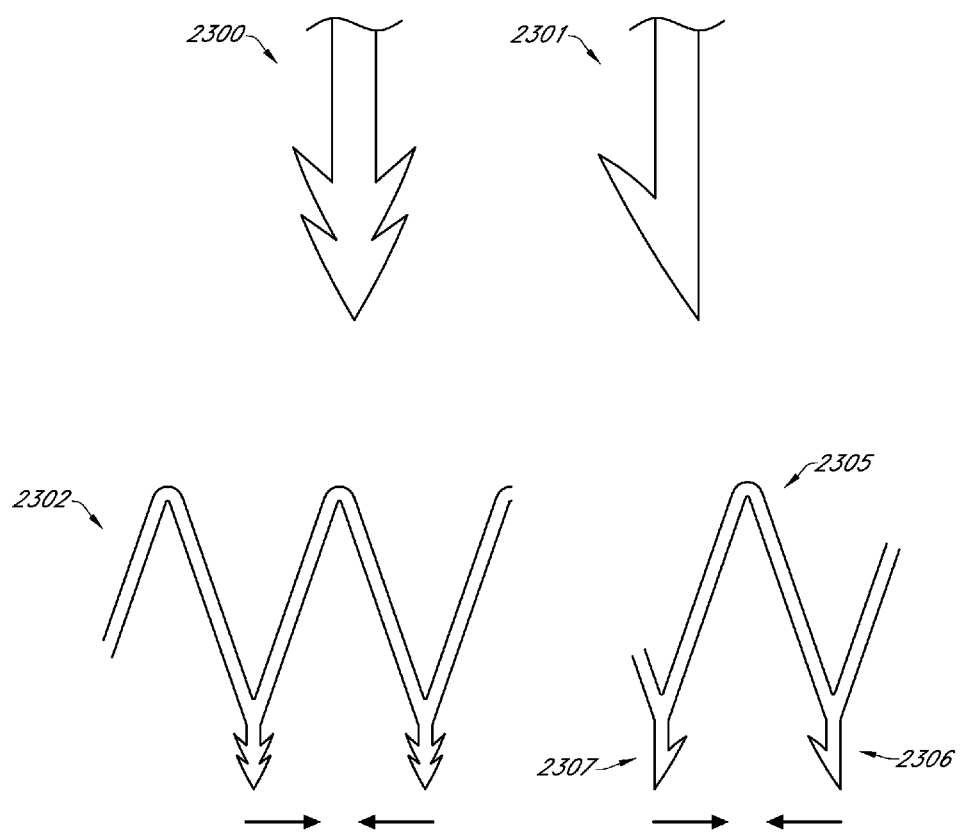
FIG. 23 illustrates example anchor configurations of various shapes.

FIG. 23 illustrates example anchor configurations of various shapes. Anchor 2300 has symmetrical barbs on either side of it. Anchor 2301 is asymmetrical, and has a barb on only one side, but also has approximately equal width to anchor 2300. The more prominent extension of the single barb may increase tissue engagement depth. Because anchor 2301 has approximately the same width as anchor 2300, in some cases it may provide a lower insertion force and have a bias to one side for lateral movement when a plurality of anchors such as anchor 2301 are moved towards one another.

Additionally, the order in which anchors are embedded and/or the sequencing of the various anchors of an implant may also vary as desired. For example, formation 2305 has anchors 2307 and 2306 that have opposing barbs that face each other. The implant may further sequence its anchors such that each anchor of the implant has an anchor with a barb facing it in a similar formation as formation 2305.

In some embodiments, an implant may also not embed all anchors into the tissue surrounding and/or including a mitral valve simultaneously. For example, every other anchor may be embedded first and/or only anchors with barbs facing in one direction may be embedded first (e.g., only anchors having barbs facing the same direction as anchor 2306 may be embedded first). The embedded anchors could first be adjusted by initial adjustments of the implant. The anchors that were not first embedded could then be embedded to finish the adjustment of the implant. Synchronizing the embedding of the anchors in this way may provide better securement of the implant to the tissue surrounding and/or including a mitral valve. The anchors may also later by cinched to push facing anchors (e.g., anchors 2306 and 2307) closer together for a better hold.

Similar synchronizing may be applied to implants with other anchor formations (e.g., implant 2302) and/or implants having any size and/or shape including those as described in this disclosure. The degree of synchronizing and/or sequencing could be selected and varied depending upon the operator's intent and the patient's need and/or disease state.

Figure 24:
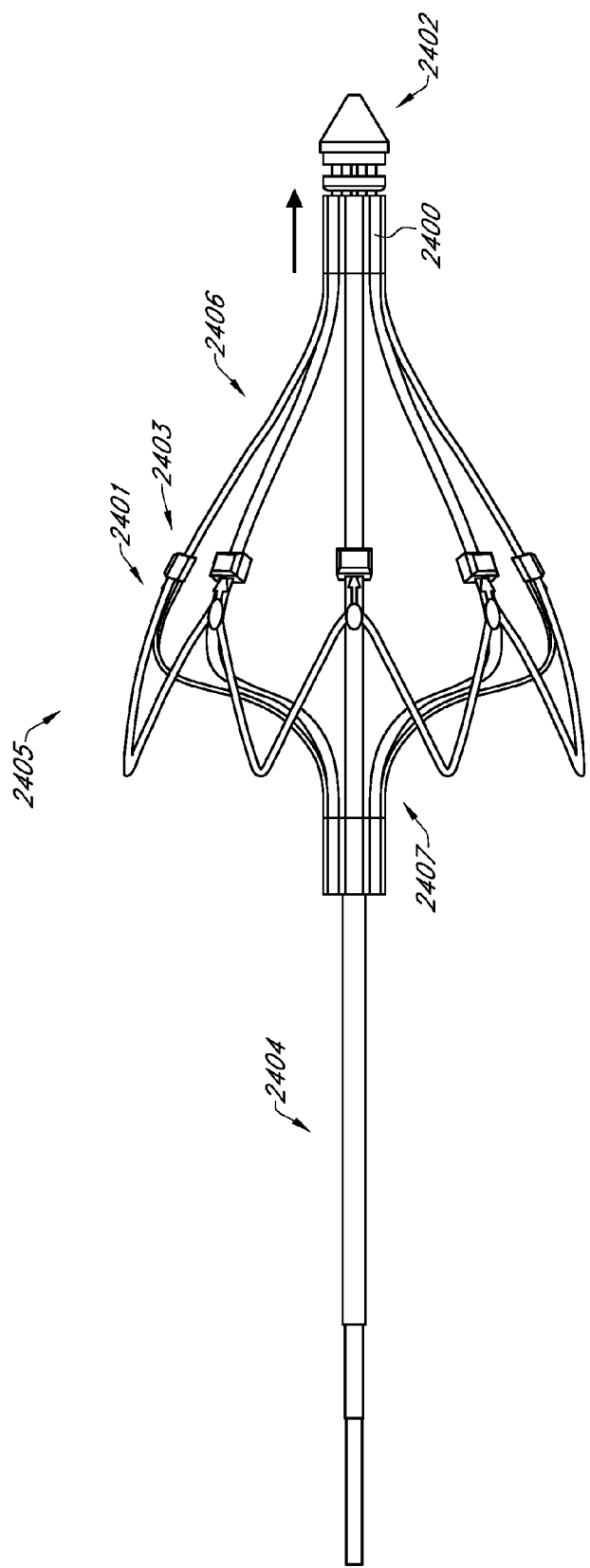
FIG. 24 illustrates an example implant with anchors covered with slideable elements.

FIG. 24 illustrates an example implant with anchors covered with slideable elements. Independent activation or exposure of the anchors of an implant may occur by using multiple ribbons configured to push or pull slideable elements (e.g., anchor covers) that cover the anchors. For example, ribbons 2406 may extend from collar 2400 to connect to slideable elements of implant 2405 in order to control the slideable elements. The slideable elements may cover the anchors of the implant. For example, slideable element 2403 covers anchor 2401. Ribbons 2406 may also aid in maintaining lateral rigidity and increasing inward flexibility of implant 2405 in conjunction with connection arms 2407. Delivery catheter 2404 may be used to guide implant 2405 into position.

Figure 25:
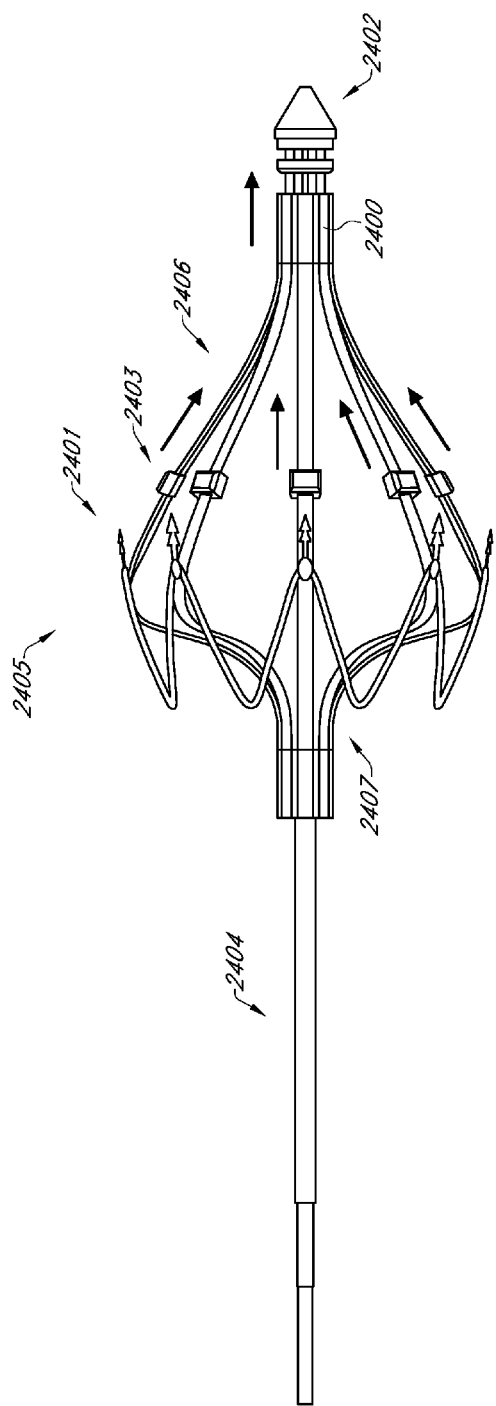
FIG. 25 illustrates the example implant from FIG. 24 with anchors exposed and ready for implantation.

In some cases, wires may pass through implant 2405 and ribbons 2406 in order to connect them together. The wires may be withdrawn in order to separate ribbons 2406 from implant 2405 in manners similar to others described in this disclosure (see, e.g., FIG. 6C). Ribbons 2406 could be constructed of material(s) including stainless steel, Nickel-Titanium, Cobalt-Chromium, Pyrolytic Carbon, Nitinol, polymer materials (e.g., PEEK), and/or other suitable implant materials. Ribbons 2406 may have a pre-shaped form or a simple flat shape that can be forced open and closed radially. FIG. 25 illustrates the example implant from FIG. 24 with anchors exposed and ready for implantation.

Figure 26A:
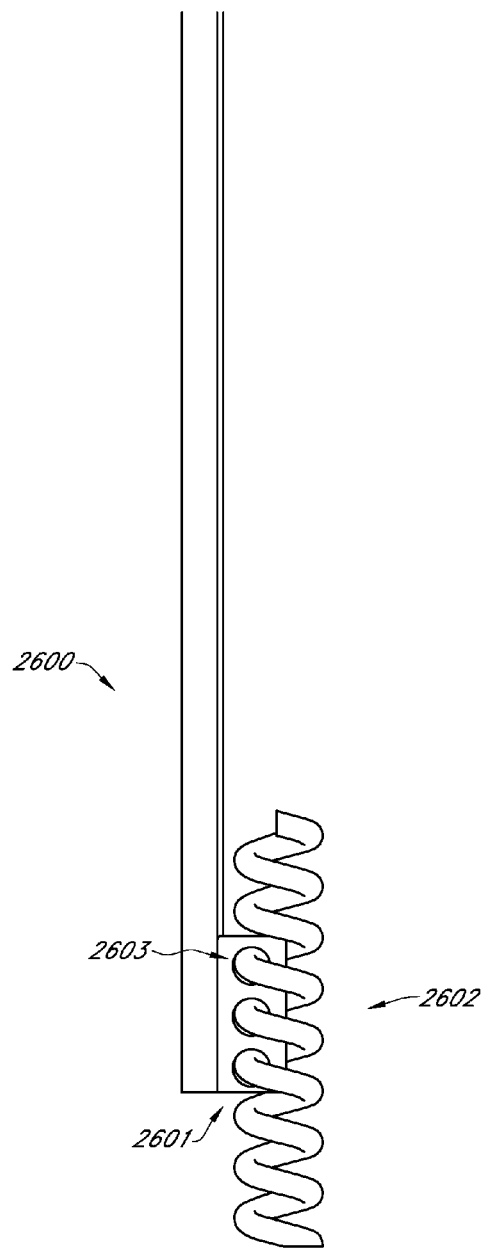
FIGS. 26A-C illustrate an example anchor that has a helical shape that can be rotated through an extension of an implant strut to engage the tissue surrounding and/or including a mitral valve.
Figure 26B:
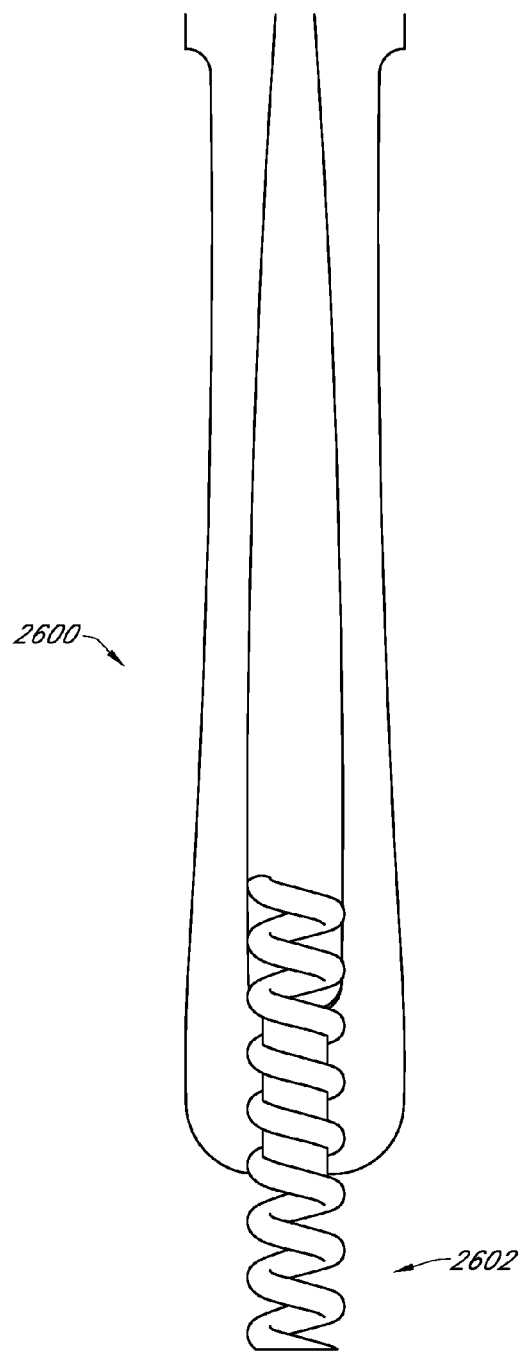
Figure 26C:
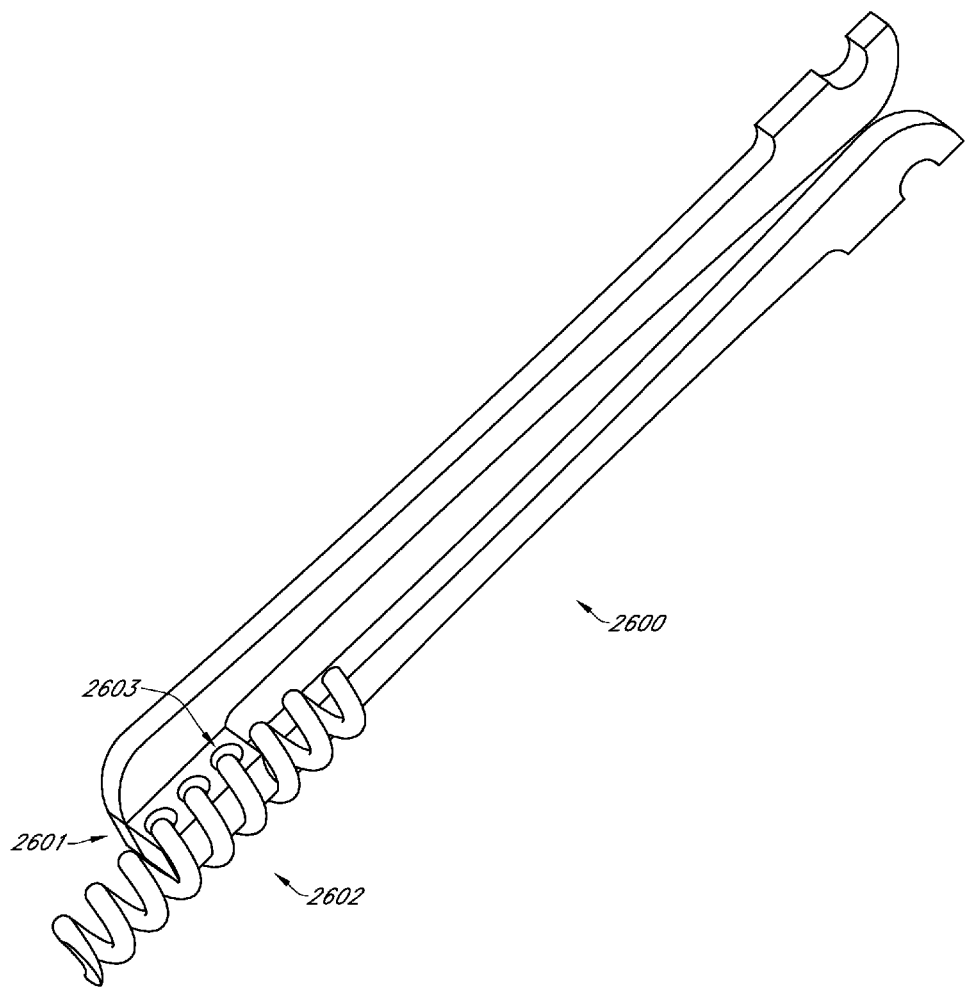

FIGS. 26A-C illustrate an example anchor that has a helical shape and a sharp distal end that can be rotated through an extension of an implant strut to engage the tissue surrounding and/or including a mitral valve. FIG. 26A illustrates a side-view of example anchor 2602, which has a helical shape. FIG. 26B illustrates a front-view, and FIG. 26C illustrates an angled view of the same anchor 2602.

Strut 2600 may have extension 2601, which comprises of holes. The holes (e.g., hole 2603) of extension 2601 may be configured such that anchor 2602 may pass through the holes with its helical shape. The helical shape of anchor 2602 may spiral through the holes, adjustably connecting to the tissue surrounding and/or including a mitral valve. One having ordinary skill the art should appreciate that anchor 2602 may be extended downward or retracted upward by rotating it such that the coils of anchor 2602 pass through the holes of extension 2601.

Anchor 2602 may be a screw-form constructed of material(s) including stainless steel, Nickel-Titanium, Cobalt-Chromium, Pyrolytic Carbon, Nitinol, polymer materials (e.g., PEEK), and/or other suitable implant materials. The cross-sectional diameter of anchor 2602 may measure in some embodiments between 0.010 and 0.025 inches and be coiled at a pitch of between 20 and 60 coils per inch, measuring about 0.03 to 0.08 inches in outer diameter. The overall length of anchor 2602 may measure, for example, about 0.2 to 0.5 inches.

Figure 27:
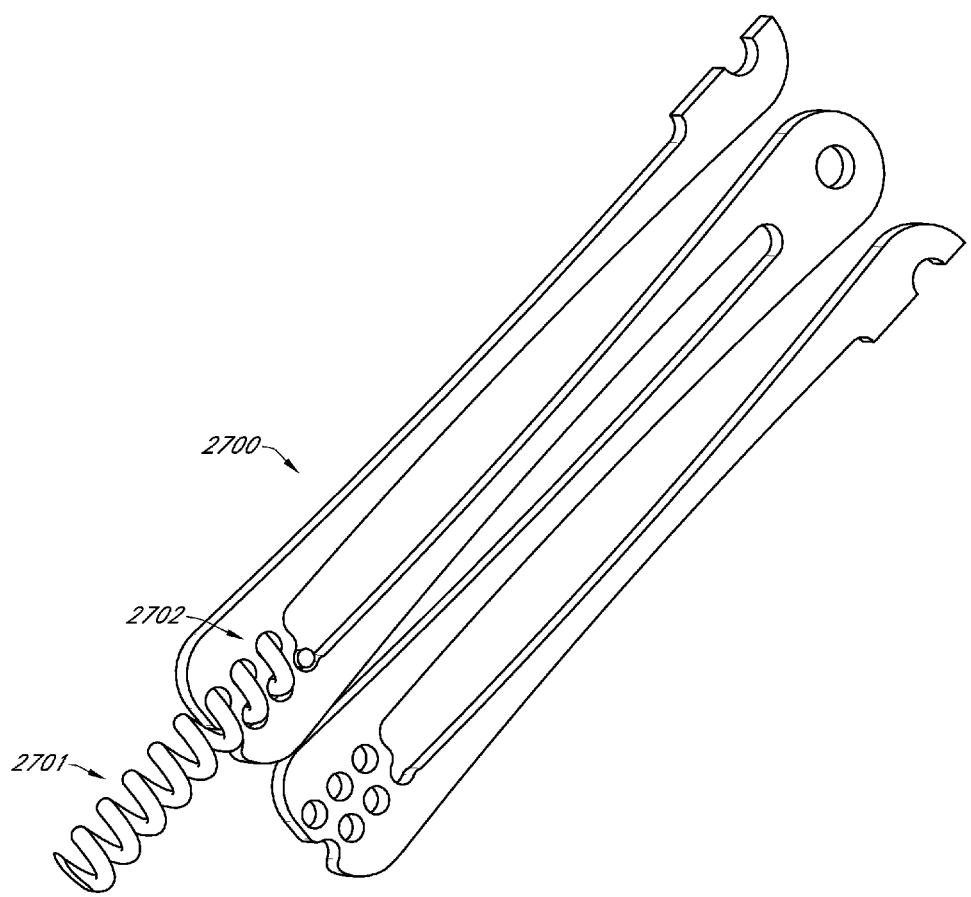
FIG. 27 illustrates an example anchor that has a helical shape that can be rotated through an implant strut to engage the tissue surrounding and/or including a mitral valve.

FIG. 27 illustrates an example anchor that has a helical shape that can be rotated through an implant strut to engage the tissue surrounding and/or including a mitral valve. Anchor 2701 is similarly constructed to anchor 2602 of FIG. 26A-C. Strut 2700 may have holes 2702, which may be patterned in diagonal and/or oblique positions such that anchor 2701 may pass through them. Again, anchor 2701 may be extended downward or retracted upward by rotating it such that the coils of anchor 2701 pass through holes 2702.

Figure 28:
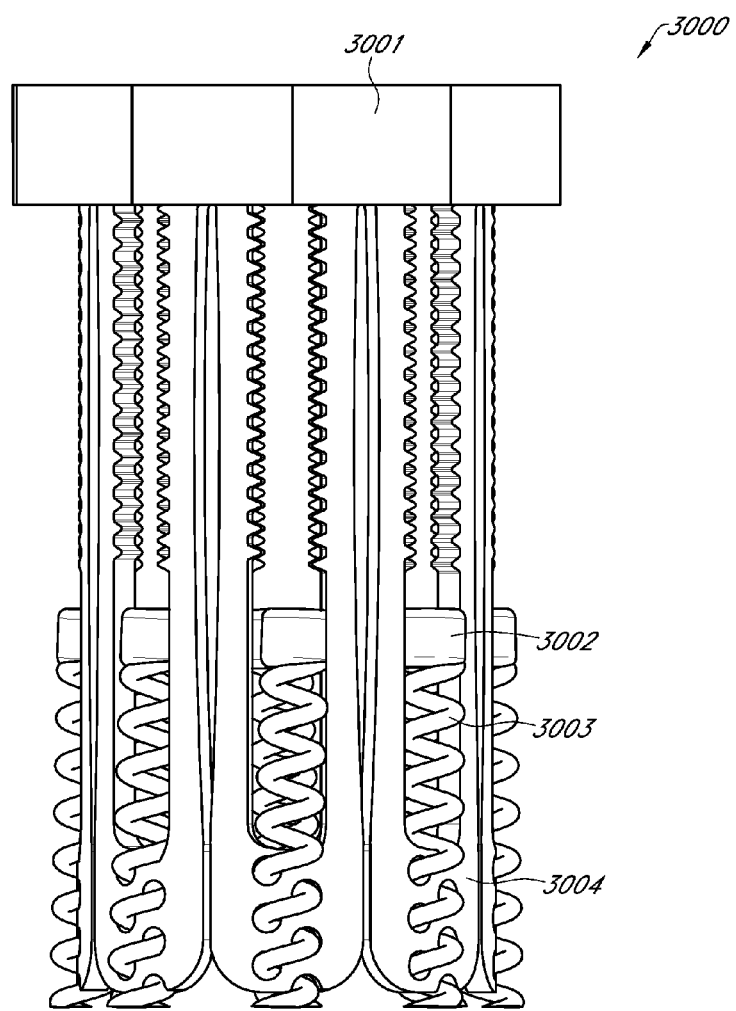
FIG. 28 illustrates an example implant with anchors that have a helical shape.

FIG. 28 illustrates an example implant with anchors that have a helical shape. Implant 3000 is in a delivery state that is smaller in diameter than its normal unconstrained state, allowing for its advancement into a left atrium via a delivery catheter. In some embodiments, implant 3000 may be still attached to a delivery catheter and the helical-shaped anchors of implant 3000 may be still in their retracted positions. For example, anchor 3003 is helical-shaped and passes through holes 3004, which may be similar to holes 2702 (FIG. 27). As illustrated, anchor 3003 is in a retracted position such that it does not extend far beyond holes 3004. Anchor 3003 has cap 3002, which may be connected to a rotational driver. The rotational driver may comprise the rotational drivers illustrated in FIGS. 13, 14, 15, and/or 16A-B, and/or any rotational driver described in this disclosure for example. Implant 3000 also has nuts, such as nut 3001, which are located on the struts of implant 3000 to adjust the size and/or shape of implant 3000. Nut 3001 may be similar to nut 602 illustrated in FIGS. 6A-B and may be rotated by any rotational drivers of this disclosure, including the rotational drivers illustrated in FIGS. 13, 14, 15, and/or 16A-B. Upon delivery to a left atrium and/or after implant 3000 has been expanded, anchor 3003 may be rotated such that it extends downward to engage the tissue surrounding and/or including a mitral valve.

Figure 29:
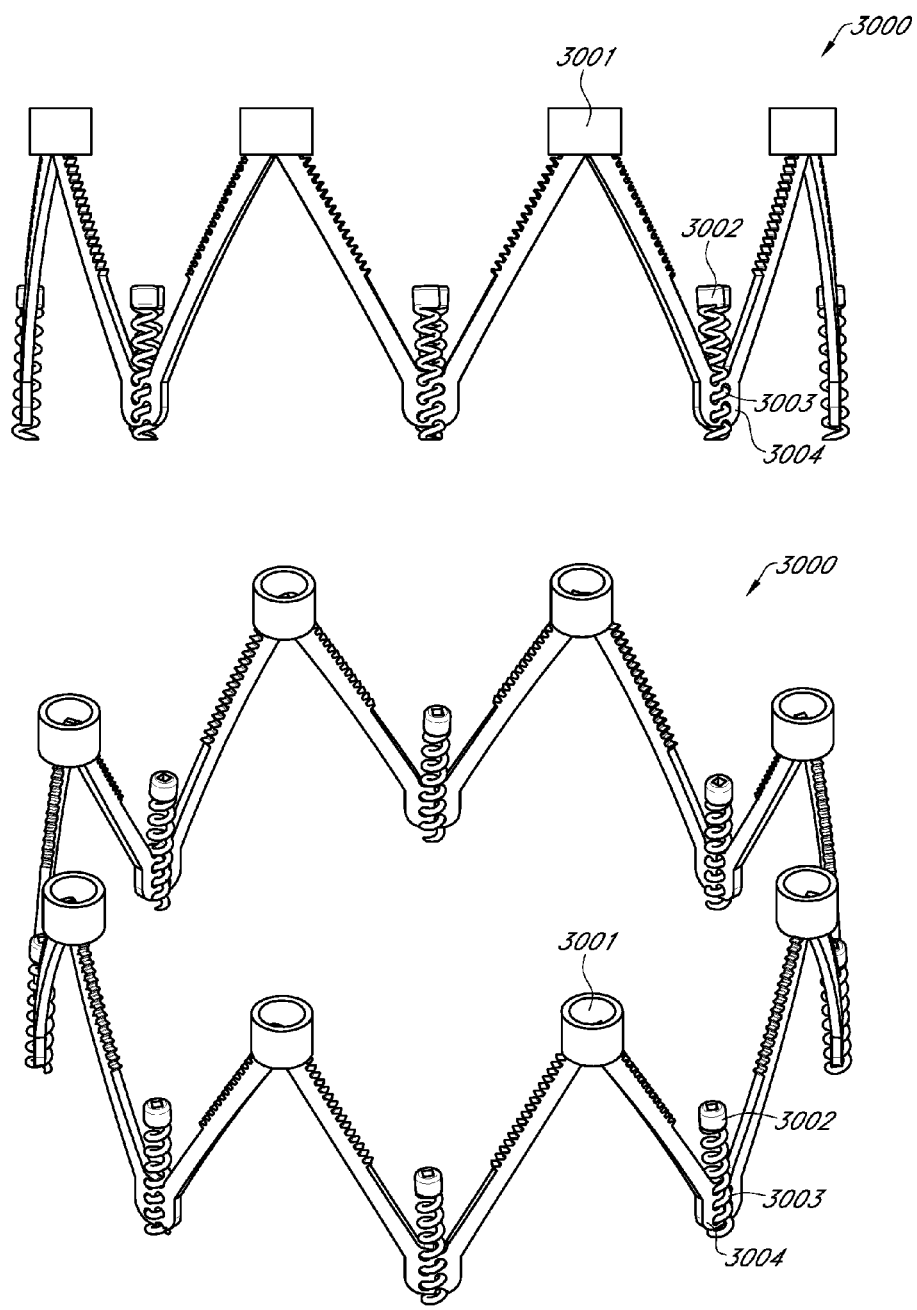
FIG. 29 illustrates the example implant of FIG. 28 in an expanded state.

FIG. 29 illustrates the example implant of FIG. 28 in a radially expanded state. Implant 3000 has been expanded to engage the tissue surrounding and/or including a mitral valve. Anchors, such as anchor 3003, are still positioned in the retracted position.

Figure 30:
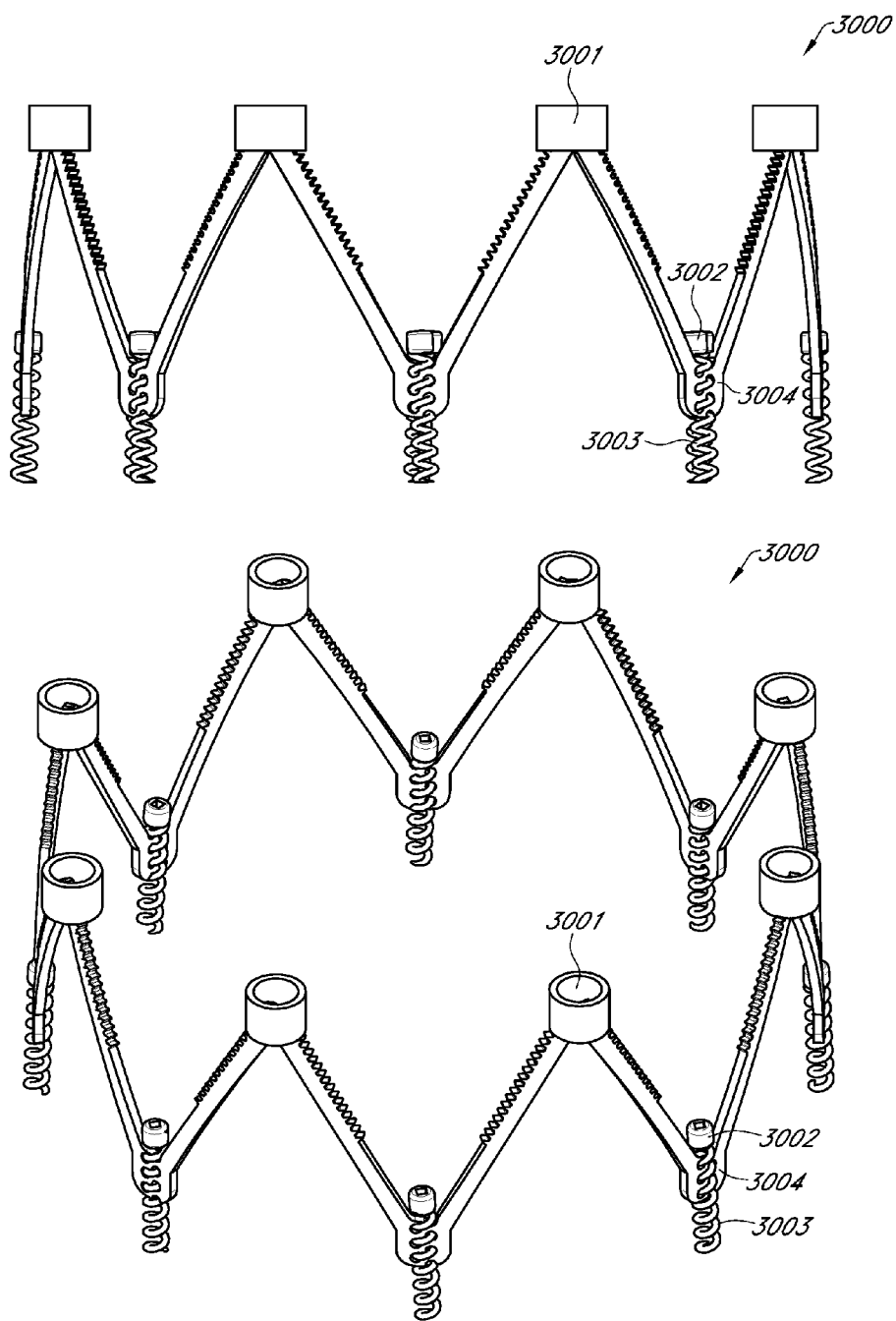
FIG. 30 illustrates the example implant of FIG. 29 where the anchors have been extended.

FIG. 30 illustrates the example implant of FIG. 29 where the anchors have been extended. For example, anchor 3003 has been rotated such that it has extended downward. In this way, it may extend into the tissue surrounding and/or including a mitral valve. Each anchor may be rotated individually or connected to one another for simultaneous extension.

Figure 31:
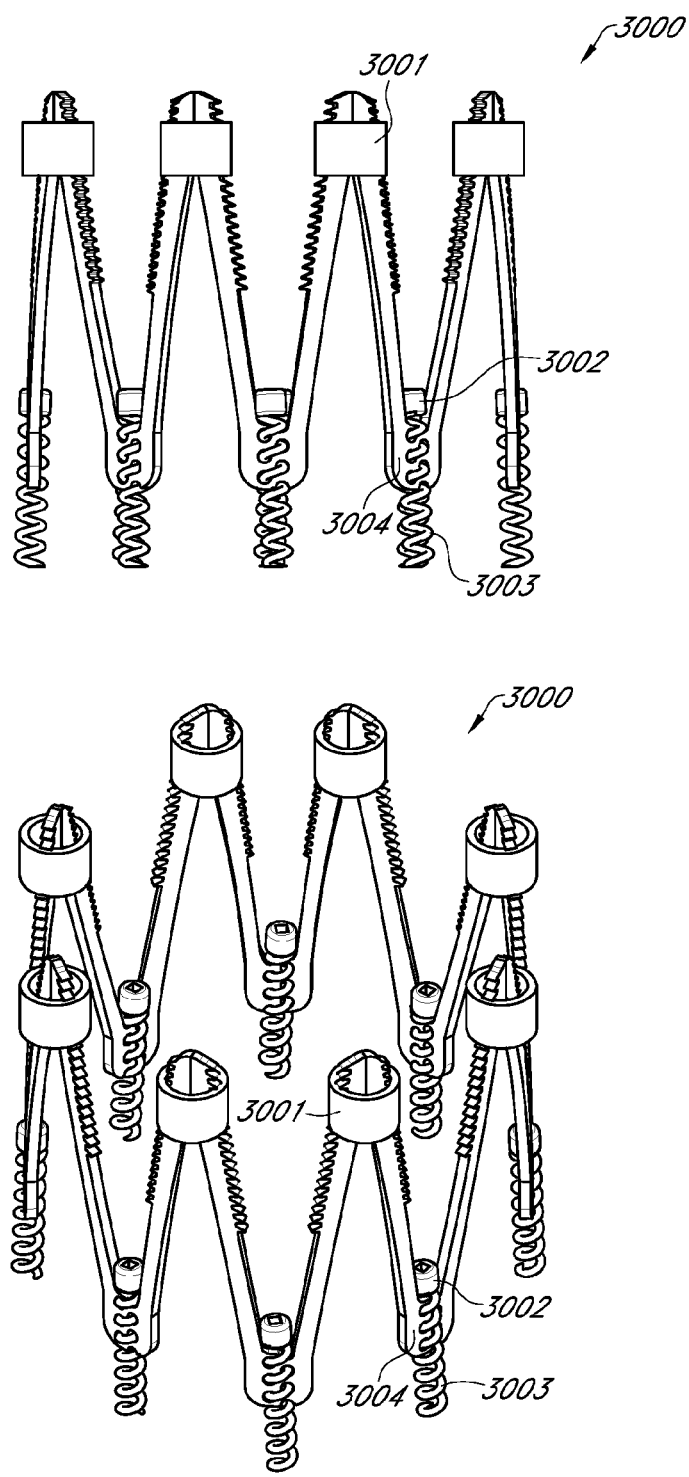
FIG. 31 illustrates the example implant of FIG. 30 where the example implant has been contracted.

FIG. 31 illustrates the example implant of FIG. 30 where the example implant has been contracted. Nuts, such as nut 3001, have been advanced along their respective struts in order to reshape implant 3000. Because anchors, such as anchor 3003, have been extended to engage the tissue surrounding and/or including a mitral valve, the reshaping of implant 3000 further reshapes that mitral valve.

One having ordinary skill in the art should appreciate that anchors having helical shapes may be adapted to any of the implants and/or mechanisms described in this disclosure. It should also be appreciated that implant 3000 may be adapted to use any of the mechanisms for adjusting size and/or shape described in this disclosure. For example, implant 3000 may use a plurality of adjustable restraints, including nuts (e.g., nut 602 (FIG. 6A), nut 680 (FIG. 6J), nut 691 (FIG. 6K)), clips (e.g., clip 634 (FIG. 6D) and clip 671 (FIG. 6I)), rings (e.g., locking ring 672 (FIG. 6I)), and/or cables (e.g., cable 640 (FIG. 6F)). These adjustable restraints may be used to adjust the size and/or shape of implant 3000 within a working range. In some embodiments, cables may also be adapted to connect to caps, such as cap 2002. In this way, the cables may provide further adjustment of the size and/or shape of implant 3000.

In some embodiments, a replacement prosthetic heart valve may be operatively coupled to any implant described in this disclosure. The valve may be positioned within the mitral, aortic, or other valve annulus and disposed axially within the central lumen of the implant body, and in some cases in a minimally-invasive procedure such as a transcatheter mitral or aortic valve replacement procedure. In some embodiments, the valve may include a stent frame operably attached to prosthetic leaflet(s) configured to coapt the valve. For example, the replacement prosthetic valve may comprise a nitinol support frame having diamond-patterned or other cells, wherein the frame is configured to support the leaflets of the mitral valve. In some embodiments, the replacement prosthetic valve may comprise a bioprosthetic valve leaflets, such as those derived from bovine, equine, or porcine tissue, such as pericardial tissue for example, or any tissue derived from or obtained from an animal. In other embodiments, the valve may be any valve replacement known in the art. In some embodiments, the implants as described herein can be utilized as a "docking station" or scaffold to temporarily or permanently be operably connected to, for example, a variety of physiological sensors measuring pressure, hemoglobin, oxygen, carbon dioxide, and the like across the valve, and other diagnostic and therapeutic devices, including drug delivery/infusion devices.

The implant may comprise connectors that allow it to connect to the valve. For example, the implant may comprise hooks, clasps, tangs, clips, fasteners, and/or cogs positioned radially inward in order to clasp, hold, clip, and/or otherwise interact with the replacement prosthetic valve. In some cases, the hooks, claps, tangs, clips, fasteners, and/or cogs may be positioned radially inward at an angle (e.g., +/−0, 10, 20, 30, 40, 50, 60, 70, 80, and/or 90 degrees, and/or any angle between any two of the aforementioned angles). The hooks, clasps, tangs, clips, fasteners, and/or cogs may also be positioned distally, proximally, and/or at an angle between distally and proximally (e.g., +/−0, 10, 20, 30, 40, 50, 60, 70, 80, and/or 90 degrees, and/or any angle between any two of the aforementioned angles) in order to clasp, hold, clip, and/or otherwise interact with the replacement prosthetic valve. In some embodiments, the implant may also comprise cable(s), wherein the cable(s) are configured to hold the implant and the replacement prosthetic valve in place. For example, one end of an adjustable cable (e.g., a cable that may be lengthened and/or shortened using any mechanism described in this disclosure) may be tied to the implant (e.g., in a receiver hole and/or strut of the implant) using a knot. The other end of the cable may be tied to the replacement prosthetic valve (e.g., to a diamond-patterned cell and/or receiver hole) using a knot. In other cases, a cable may pass through the replacement prosthetic valve and the implant, and the ends of the cable may be tied together to hold the valve and the implant together. For example, a cable may pass axially through the frame of a diamond-patterned cell and/or a receiver hole of the replacement prosthetic valve, and pass axially through a strut and/or receiver hole of the implant. The ends of the cable may be tied together to secure the implant and the replacement prosthetic valve together. In any of the aforementioned ways, the implant may hold the valve in place and secure its placement. As such, the implant may act as a docking station for the replacement prosthetic valve. In some cases, the replacement prosthetic valve and the implant may behave functionally as a replacement prosthetic valve with anchors for securement.

The valve may be delivered to the mitral valve before, after, or at the same time as any implant described in this disclosure. For example, the replacement prosthetic valve may be delivered independently of the implant through one of several methods, including transfemoral, transapical, subclavian, and direct aortic implantation. The replacement prosthetic valve may then be placed within the implant, or the implant may be place around the replacement prosthetic valve. For example, in some cases where the replacement prosthetic valve is positioned in the valve region before the implant, the implant may expand so that the replacement prosthetic valve may be medially positioned within the implant's frame. Once the replacement prosthetic valve is medially positioned within the frame of the implant, the implant may contract around the replacement prosthetic valve, causing the hooks, clasps, tangs, clips, fasteners, and/or cogs positioned on the implant to clasp, hold, clip, and/or otherwise interact with the replacement prosthetic valve. As another example, the implant may already be positioned in an expanded configuration in the heart before the valve is positioned in the same or a different procedure, on the same day or a later date. The valve may then pass axially through the central lumen of the implant, and be positioned in the mitral, aortic, or other valve via a percutaneous, transapical, transseptal, or other approach, some of which are described in the present specification. The implant may then contract around the valve, causing the hooks, clasps, tangs, clips, fasteners, and/or cogs positioned on the implant to clasp, hold, clip, and/or otherwise interact with the prosthetic replacement valve. Non-limiting examples of valves that can be delivered or modified for delivery and anchored with the implants described herein include the FORTIS or SAPIEN valves from Edwards Lifesciences, the TIARA valve from Neovasc, and the COREVALVE and ENGAGER valves from Medtronic, Inc.

In some embodiments, the prosthetic replacement valve may also be delivered at the same time as the implant. For example, the valve may be coupled to the same delivery catheter (e.g., delivery catheter 301 (FIG. 3)) and/or delivery system as the implant. In some cases, the valve may be placed coaxially within the implant such that implant and valve may be deployed at the same time. In other cases, the valve may be placed off-axis, but still disposed within the implant's frame during deployment.

Figure 32:
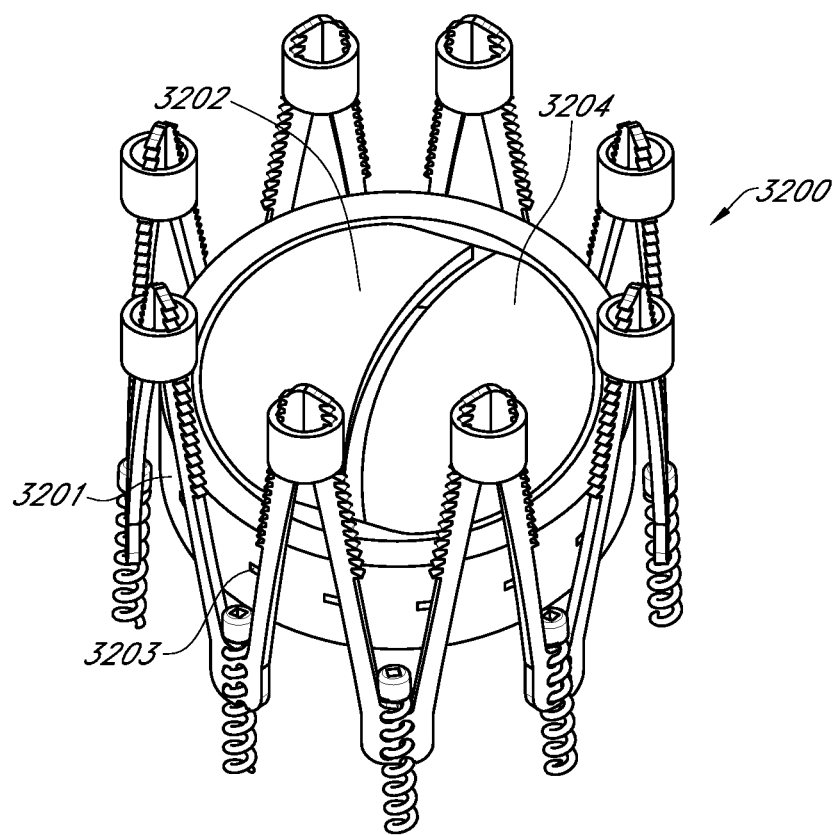
FIG. 32 illustrates an example replacement prosthetic heart valve operably coupled to an example implant.

FIG. 32 illustrates an example replacement prosthetic heart valve operably coupled to an example implant. Implant 3200 has been collapsed around valve 3201. Valve 3201 is a prosthetic valve comprising anterior leaflet 3202 and posterior leaflet 3204. Implant 3200 has a plurality of connectors (e.g., connector 3203) that connects implant 3200 to valve 3201. Connector 3203 may be a hook, clasp, tang, clip, fastener, and/or cog positioned on implant 3200 to clasp, hold, clip, and/or otherwise interact with valve 3201.

Various other modifications, adaptations, and alternative designs are of course possible in light of the above teachings. For example, while generally described in conjunction with resizing and/or reshaping of a mitral valve annulus, in some embodiments, aortic, tricuspid, pulmonic, or venous valves can also be altered using devices and methods as disclosed herein. Other vascular and non-vascular body lumens such as, for example, the esophagus, stomach, intestines, ureters, fallopian tubes, and other lumens can also be altered using devices and methods as disclosed herein. Therefore, it should be understood at this time that within the scope of the appended claims the invention may be practiced otherwise than as specifically described herein. It is contemplated that various combinations or subcombinations of the specific features and aspects of the embodiments disclosed above may be made and still fall within one or more of the inventions. Further, the disclosure herein of any particular feature, aspect, method, property, characteristic, quality, attribute, element, or the like in connection with an embodiment can be used in all other embodiments set forth herein. Accordingly, it should be understood that various features and aspects of the disclosed embodiments can be combined with or substituted for one another in order to form varying modes of the disclosed inventions. Thus, it is intended that the scope of the present inventions herein disclosed should not be limited by the particular disclosed embodiments described above. Moreover, while the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents, and alternatives falling within the spirit and scope of the various embodiments described and the appended claims. Any methods disclosed herein need not be performed in the order recited. The methods disclosed herein include certain actions taken by a practitioner; however, they can also include any third-party instruction of those actions, either expressly or by implication. For example, actions such as "inserting an adjustable valvular ring proximate an annulus" includes "instructing the inserting of an adjustable valvular ring proximate an annulus." The ranges disclosed herein also encompass any and all overlap, sub-ranges, and combinations thereof. Language such as "up to," "at least," "greater than," "less than," "between," and the like includes the number recited. Numbers preceded by a term such as "approximately", "about", and "substantially" as used herein include the recited numbers (e.g., about 10%=10%), and also represent an amount close to the stated amount that still performs a desired function or achieves a desired result. For example, the terms "approximately", "about", and "substantially" may refer to an amount that is within less than 10% of, within less than 5% of, within less than 1% of, within less than 0.1% of, and within less than 0.01% of the stated amount.

What is claimed is:

1. An implant for reshaping a heart valve annulus, comprising:
    a tubular body having a proximal end, a distal end, a central lumen and a longitudinal axis extending therethrough, the tubular body dimensioned for positioning within an atrium and attachment to tissue surrounding the heart valve;
    the tubular body comprising at least a first pair of adjacent struts joined at a proximally facing apex, and at least a second pair of adjacent struts joined at a distally facing apex;
    a plurality of distally facing anchors on the distal end of the tubular body, the anchors configured to embed into tissue surrounding the heart valve;
    a moveable restraint carried by the tubular body and configured to at least partially surround the first pair of adjacent struts, wherein the moveable restraint is axially movable relative to the proximally facing apex along the first pair of adjacent struts toward the distal end to decrease an angle between the first pair of adjacent struts; and
    a rotatable threaded member secured with the proximally facing apex, the rotatable threaded member extending through the moveable restraint, wherein rotation of the rotatable threaded member causes the moveable restraint to move axially along the first pair of adjacent struts.

2. The implant of claim 1, wherein the moveable restraint is moved along the pair of adjacent struts by sliding of the moveable restraint in response to rotation of the rotatable threaded member.

3. The implant of claim 1, wherein the plurality of anchors are helical-shaped anchors rotatably carried by the implant body, and wherein rotation of the anchors causes the anchors to extend distally relative to the tubular body to embed into the tissue surrounding the heart valve.

4. The implant of claim 1, further comprising a delivery mechanism comprising a rotational driver having a hook at a distal end and configured to transmit rotational motion to the rotatable threaded member to cause the moveable restraint to move axially along the first pair of adjacent struts.

5. The implant of claim 1, wherein the moveable restraint comprises an internally threaded member.

6. The implant of claim 1, wherein the rotatable threaded member is secured with the proximally facing apex via a retainer.

7. The implant of claim 1, wherein the moveable restraint further comprises a locking ring.

8. The implant of claim 1, wherein the moveable restraint comprises a nut.

9. The implant of claim 1, wherein the moveable restraint comprises a clip.

10. The implant of claim 1, wherein the moveable restraint is configured to reversibly adjust the tubular body radially within a working range.

11. The implant of claim 1, wherein the plurality of anchors comprises eight anchors.

12. The implant of claim 1, wherein the plurality of anchors each have a helical shape that engages the tissue by rotation of each anchor.

13. The implant of claim 1, wherein the plurality of anchors are configured to embed into tissue surrounding the heart valve by extending the anchors distally relative to the implant body.

14. The implant of claim 1, wherein the anchors are retractable.

15. The implant of claim 1, further comprising:
a plurality of pairs of adjacent struts with each pair having an angle therebetween; and
a plurality of the moveable restraints, with each moveable restraint at least partially surrounding a respective pair of the plurality of pairs of adjacent struts, wherein each moveable restraint can be moved along the respective pair of adjacent struts to change the angle between the respective pair of adjacent struts, thereby causing the tubular body to change in diameter.

16. The implant of claim 1, wherein the tubular body is further configured to operably couple to a replacement prosthetic heart valve.

* * * * *

UNITED STATES PATENT AND TRADEMARK OFFICE
CERTIFICATE OF CORRECTION

PATENT NO. : 9,913,706 B2
APPLICATION NO. : 15/689467
DATED : March 13, 2018
INVENTOR(S) : Randall Lashinski et al.

It is certified that error appears in the above-identified patent and that said Letters Patent is hereby corrected as shown below:

In the Specification

In Column 3 at Line 5, Change "FIG." to --FIGS.--.

In Column 6 at Line 38, Change "biocompatility" to --biocompatibility--.

In Column 11 at Line 19, Change "aperatures)," to --apertures),--.

In Column 13 at Line 49, Change "FIG." to --FIGS.--.

In Column 15 at Line 19, Change "FIG." to --FIGS.--.

In Column 24 at Line 25, Change "FIG." to --FIGS.--.

Signed and Sealed this
Seventeenth Day of July, 2018

Andrei Iancu
*Director of the United States Patent and Trademark Office*